US006365390B1

(12) United States Patent
Blum et al.

(10) Patent No.: US 6,365,390 B1
(45) Date of Patent: Apr. 2, 2002

(54) PHENOLIC ACID ESTERASES, CODING SEQUENCES AND METHODS

(75) Inventors: David L. Blum, San Diego, CA (US); Irina Kataeva, Athens, GA (US); Xin-Liang Li, Athens, GA (US); Lars G. Ljungdahl, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/390,234

(22) Filed: Sep. 3, 1999

Related U.S. Application Data
(60) Provisional application No. 60/099,136, filed on Sep. 4, 1998.

(51) Int. Cl.$^7$ .............................. C12N 9/18; C07H 21/04
(52) U.S. Cl. ..................... 435/197; 435/183; 435/320.1; 435/252.3; 536/23.1; 536/23.2; 530/350
(58) Field of Search ................................ 435/197, 183, 435/320.1, 252.3; 536/23.1, 23.2; 530/350

(56) References Cited

U.S. PATENT DOCUMENTS 5,882,905 A    3/1999   Saha et al. ................... 435/105

FOREIGN PATENT DOCUMENTS

| EP | 0513140 B1 | 9/1995 | ............ D21C/9/10 |
| GB | 2301103 | 11/1996 | ............ C12N/9/18 |
| WO | 98/46768 | 10/1998 | ........... C12N/15/55 |

OTHER PUBLICATIONS

Blum et al. (1999) "Characterization of a Feruloyl Esterase from the Anaerobic Fungus Orpinomyces sp. Strain PC–2" Abstracts. 99$^{th}$ General Meeting of the American Society for Microbiology. Chicago, IL. May 30–Jun. 3, 1999. vol. 99, pp. 430–431.
Borneman and Akin (1990) "Lignocellulose Degradation by Rumen Fungi and Bacteria: Ultrastructure and Cell Wall Degrading Enzymes" In: *Microbial and Plan Opportunities to Improve Lignocellulose Utilization by Ruminants.* D.E. Akin; L.G. Ljungdahl; J.R. Wilson; and P.J. Harris (Eds.) Elsevier Science Publishing Co. New York, NY. pp. 325–339.*
Borneman et al. (1992) "Purification and Partial Characterization of Two Feruloyl Esterases from the Anaerobic Fungus Neocallimastix Strain MC–2" *Applied and Environmental Microbiology* 58:3762–3766.*
Borneman et al. (1990) "Assay for trans–p–Coumaroyl Esterase Using a Specific Substrate from Plant Cell Walls" *Analytical Biochemistry* 190:129–133.*
Castanares and Wood (1992) "Purification and Characterization of a Feruloyl/p–Coumaroyl Esterase from Solid-State Cultures of the Aerobic Fungus Penicillium pinophilum" *Biochemical Society Transactions* 20:275S.*

Chen et al. (1995) "A Cyclophilin from the Polycentric Anaerobic Rumen Fungus Orpinomyces sp. Strain PC–2 is Highly Homologous to Vertebrate Cyclophilin B" *Proc. Natl. Acad. Sci. USA* 92:2587–2591.*
Chritov and Prior (1993) "Esterases of Xylan–Degrading Microorganisms: Production, Properties, and Significance" *Enzyme Microb. Technol.* 15:460–475.*
Dalrymple and Swadling (1997) "Expression of a *Butyrivibrio fibrisolvens* E14 Gene (cinB) Encoding an Enzyme with Cinnamoyl Ester Hydrolase Activity is Negatively Regulated by the Product of an Adjacent Gene (cinR)" *Microbiology* 143:1203–1210.
Dalrymple et al. (1996) "Cloning of a Gene Encoding Cinnamoyl Ester Hydrolase from the Ruminal Bacterium *Butyrivibrio fibrisolvens* E14 by a Novel Method" *FEMS Microbiology Letters* 143:115–120.
De Vries et al. (1997) "The faeA Genes from *Aspergillus niger* and *Aspergillus tubingensis* Encode Ferulic Acid Esterases Involved in Degradation of Complex Cell Wall Polysaccharides" *Applied and Environmental Microbiology* 63:4638–4644.
Faulds and Williamson (1991) "The Purification and Characterization of 4–Hydroxy–3–Methoxycinnamic (Ferulic) Acid Esterase from *Streptomyces olivochromogenes*" *Journal of General Microbiology* 137:2339–2345.
Felix and Ljungdahl (1993) "The Cellulosome: The Exocellular Organelle of Clostridium" *Annu. Rev. Microbiol.* 47:791–819.
Ferreira et al. (1993) "A Modular Esterase from *Pseudomonas fluorescens* subsp. *cellulosa* Contains a Non–Catalytic Cellulose–Binding Domain" *Biochemical Journal* 294:349–355.
Flint et al. (193) "A Bifunctional Enzyme, with Separate Xylanase and β(1,3–1,4)–Glucanase Domains, Encoded by the xnyD Gene of *Ruminococcus flavefaciens*" *Journal of Bacteriology* 175:2943–2951.
Fontes et al. (1995) "Evidence for a General Role for Non–Catalytic Thermostabilizing Domains in Xylanases from Thermophilic Bacteria" *Biochem. J.* 307:151–158.
Genbank Accession No. AF047761, *Clostridium thermocellum* xylanase V and U.
Genbank Accession No. L48074, *Aspergillus fumigatus* dipeptidyl peptidase.

(List continued on next page.)

*Primary Examiner*—Rebecca E. Prouty
*Assistant Examiner*—Richard Hudson
(74) *Attorney, Agent, or Firm*—Greenlee Winner and Sullivan PC

(57) ABSTRACT

Described herein are four phenolic acid esterases, three of which correspond to domains of previously unknown function within bacterial xylanases, from XynY and XynZ of *Clostridium thermocellum* and from a xylanase of Ruminococcus. The fourth specifically exemplified xylanase is a protein encoded within the genome of Orpinomyces PC-2. The amino acids of these polypeptides and nucleotide sequences encoding them are provided. Recombinant host cells, expression vectors and methods for the recombinant production of phenolic acid esterases are also provided.

26 Claims, 11 Drawing Sheets

OTHER PUBLICATIONS

Genbank Accession No. M22624, *Clostridium thermocellum* xylanase Z.

Genbank Accession No. P31471, *Escherichia coli* 44.1 kD protein.

Genbank Accession No. P51584, *Clostridium thermocellum* xylanase Y.

Genbank Accession No. S58235, Ruminococcus sp. xylanase.

Genbank Accession No. X83269, *Clostridium thermocellum* xylanase Y.

Grépinet et al. (1988) "Nucleotide Sequence and Deletion Analysis of the Xylanase Gene (xynZ) of *Clostridium thermocellum*" *Journal of Bacteriology* 170:4582–4588.

Kirby et al. (1998) "Plant Cell Wall Degrading Enzyme Complexes from the Cellulolytic Rumen Bacterium *Ruminococcus flavefaciens*" *Biochemical Society Transactions* 26:S169.

MacKenzie and Bilous (1988) "Ferulic Acid Esterase Activity from *Schizophyllum commune*" *Applied and Environmental Microbiology* 54:1170–1173.

McDermid et al. (1990) "Esterase Activities of *Fibrobacter succinogenes* subsp. *succinogenes* S85" *Applied and Environmental Microbiology* 56:127–132.

McSweeney et al. (1998) "Butyrivibrio spp. and Other Xylanolytic Microorganisms from the Rumen have Cinnamoyl Esterase Activity" *Anaerobe* 4:57–65.

Ralph et al. (1995) "Lignin–Ferulate Cross–Links in Grasses: Active Incorporation of Ferulate Polysaccharide Esters Into Ryegrass Lignins" *Carbohydrate Research* 275:167–178.

Sakka et al. (1996) "Identification and Characterization of Cellulose–Binding Domains in Xylanase A of *Clostridium stercorarium*" *Ann. NY Acad. Sci.* 782:241–251.

Sakka et al. (1993) "Nucleotide Sequence of the *Clostridium stercorarium* xynA Gene Encoding Xylanase A: Identification of Catalytic and Cellulose Binding Domains" *Biosci. Biotech. Biochem.* 57:273–277.

Arakaki et al. Xylanase 1 from Ruminococcus sp. with a new pattern of domain shuffling, Genbank Accession No.: Z49970, Aug. 1995.

* cited by examiner

FIG. 1

```
XynV_Clotm  241  PTPEPTPRSAFSKIEAEEYNSLKSSTIQTIGT.SDGGSGIGYIESGDYLVFNKINFGNGA
XynU_Clotm  241  PTPEPTPRSAFSKIESEEYNSLKSSTIQTIGT.SDGGSGIGYIESGDYLVFNKINFGNGA
XynZ_Clotm  289  -VPTPSEKPANTRIEAEDYDGINSSSIEIGVPPEGGRGIGYITSGDYLVYKSIDFGNGA
XynA_Closr  240  PEQSFIRRDAFSIEAEEYNSTNSSTEQVIGTP.NNGRGIGYIENGNTVTYSNIDFGSGA XynV_Clotm  300  NSFKARVASGADTPTNIQLRLGSPTGTLIGTLTVASTGGWNNYEEKSCSITNTTG
XynU_Clotm  300  NSFKARVASGADTPTNIQLRLGSPTGTLIGTLTVASTGGWNNYEEKSCSITNTTG
XynZ_Clotm  348  TSFKAKVANA..NTSNIELRENGPNGTLIGTISVKSTGDWNTYEEQICSISKVTG
XynA_Closr  299  TGFSATVAE..EVNTSIQIRSDSPTGTLEGTLYVSSTGSWNTYQTVSTNISKITG
```

 Signal peptide
 FAE domain
 Unknown domain
FIG. 10

US 6,365,390 B1

PHENOLIC ACID ESTERASES, CODING SEQUENCES AND METHODS

CROSS REFERENCE TO RELATED APPLICATIONS

This application claims priority from United States Provisional Application No. 60/099,136, filed Sep. 4, 1998.

ACKNOWLEDGEMENT OF FEDERAL RESEARCH SUPPORT

This invention was made, at least in part, with finding from the United States Department of Energy (Grant No. DE-FG05 93ER 20127). Accordingly, the United States Government has certain rights in this invention.

BACKGROUND OF THE INVENTION

The field of the present invention is the area of enzymes which degrade plant cell walls, and certain other substrates, in particular, the phenolic acid esterases, feruloyl esterases and/or coumaroyl esterase, nucleotide sequences encoding them and recombinant host cells and methods for producing them.

Plant cell wall material is one of the largest sources of renewable energy on earth. Plant cell walls are composed mainly of cellulose, hemicelluloses, lignin and pectin. Arabinoxylan is one of the main constituents of hemicelluloses. It is composed of a chain of β(1→4) linked xylose units that are substituted by arabinose, acetate, and glucuronic acid. The arabinose has ester linked ferulic and p-coumaric acids [Borneman et al. (1993) In: Hemicellulose and Hemicellulases, Coughlan and Hazlewood, Eds., pp. 85–102]. Ferulic acid has been shown to link hemicellulose and lignin [Ralph et al. (1995) *Carbohydrate Research* 275:167–178]. Feruloyl esterases are involved in breaking the bond between the arabinose and ferulic acid, thus releasing the covalently bound lignin from hemicelluloses. Feruloyl esterases have been found in many bacteria as well as fungi, but have not been extensively studied nor is there much sequence data available [Christov and Prior (1993) *Enzyme. Microb. Technol.* 15(6):460–75].

*Clostridium thermocellum* is a gram-positive bacterium that produces a multienzymatic structure termed the cellulosome. The cellulosome is one of the most active cellulose degrading complexes described to date. The cellulosome has a multi-polypeptide structure, including a scaffolding subunit which has nine cohesins binding to nine catalytic subunits, a dockerin domain for attachment to the cell wall, and a cellulose binding domain [Felix and Ljungdahl (1993) *Annu. Rev. Microbiol.* 47:791–819]. The catalytic subunits include endoglucanase, cellobiohydrolase, lichenase, and xylanase, many of which have been cloned and sequenced. They all have multidomain structures that include at least a dockerin domain for binding to the scaffolding domain, a linker, and a catalytic domain. They may also contain cellulose binding domains and fibronectin-like domains. There are reports that some enzymatic components may have more than one catalytic domain. Two of these are xylanase Y [XynY, Fontes et al. (1995) *Biochem. J.* 307: 151–158] and xylanase Z [XynZ, Grépinet et al. (1988) *J. Bacteriol.* 170(10):4582–8]. XynY has a C-terminal domain whereas XynZ N-terminal domain without any functions determined. Although enzymes with dual catalytic domains (xylanase and β-glucanase) have been found in other bacteria [Flint et al. (1993) *J. Bacteriol.* 175:2943–2951] neither phenolic acid esterase nor bifunctional enzymes have been found in *C thermocellum*.

There is a need in the art for phenolic acid esterases, feruloyl esterases and/or coumaroyl esterases in pure form which degrade plant cell wall materials, and certain other substrates, and for DNA encoding these enzymes to enable methods of producing ferulic acid and/or coumaric acid as well as facilitating degradation of plant cell wall materials.

SUMMARY OF THE INVENTION

The present invention provides novel phenolic acid esterases, having feruloyl esterase and coumaroyl esterase activities, and coding sequences for same.

One phenolic acid esterase of the present invention corresponds to a domain of previously unknown function from xylanase Y of *Clostridium thermocellum*. The recombinantly expressed domain polypeptide is active and has an amino acid sequence as given in FIG. 1 as "XynY_Clotm." The nucleotide sequence encoding the esterase polypeptide is given in Table 5, nucleotides 2383–3219, exclusive of translation start and stop signals. See also SEQ ID NOs:11 and 12.

A second phenolic acid esterase of the present invention corresponds to a domain of previously unknown function of xylanase Z from C. thermocellum. The amino acid sequence of the esterase domain, which also is active when expressed as a recombinant polypeptide, is given in FIG. 1 as "XynZ_Clotm." The nucleotide sequence encoding this polypeptide is given in Table 6, nucleotides 58–858. The present invention further provides a phenolic acid esterase polypeptide further comprising a cellulose binding domain. A specifically identified cellulose binding domain has an amino acid sequence as given in Table 6, 289–400, with a corresponding coding sequence as given in Table 6, nucleotides 867–1200. See also SEQ ID NOs:13 and 14.

An additional object of the present invention is a phenolic acid esterase (i.e., a feruloyl esterase) derived from a previously uncharacterized portion of a Ruminococcus xylanase (See FIG. 1). The coding (nucleotides 2164–2895, exclusive of translation start and stop signals) and deduced amino acid sequences (amino acids 546–789) are given in Table 10. See also SEQ ID NOs: 15 and 16.

The present invention further provides a feruloyl (phenolic acid) esterase from the anaerobic fungus Orpinomyces PC-2. The coding sequence and deduced amino acid sequences of the mature esterase protein are given in Table 9, and the purification of the Orpinomyces enzyme is described herein below. See also SEQ ID NOs: 17 and 18.

A further aspect of the present invention methods for the recombinant production of the phenolic (especially ferulic) acid esterases of the present invention. *Escherichia coli, Bacillus subtilis,* Streptomyces sp., *Saccharomyces cerevisiae, Aureobasidium pullulans, Pichia pastoris,* Trichoderma, *Aspergillus nidulans* or any other host cell suitable for the production of a heterologous protein can be transfected or transformed with an expression vector appropriate for the chosen host. Compatible combinations of vectors and host cells are well known in the art as are appropriate promoters to be used to direct the expression of a particular coding sequence of interest. The recombinant host cells are cultured under conditions suitable for growth and expression of the phenolic acid esterase and the recombinant esterase is then collected or the recombinant host cells in which the esterase has been produced are collected. The coding sequence of the esterase can be operably linked to a nucleotide sequence encoding a signal peptide which is known in the art and functional in the desired host cell if secretion of the esterase into the culture medium is desired.

In that case, the culture medium serves as the source of esterase after growth of the host cells.

It is recognized by those skilled in the art that the DNA sequences may vary due to the degeneracy of the genetic code and codon usage. All DNA sequences which encode a phenolic acid esterase polypeptide having a specifically exemplified amino acid sequence are included in this invention, including DNA sequences encoding them having an ATG preceding the coding region for the mature protein and a translation termination codon (TAA, TGA or TAG) after the coding sequence.

Additionally, it will be recognized by those skilled in the art that allelic variations may occur in the phenolic acid esterase polypeptide coding sequences which will not significantly change activity of the amino acid sequences of the polypeptides which the DNA sequences encode. All such equivalent DNA sequences are included within the scope of this invention and the definition of a phenolic acid esterase. The skilled artisan will understand that the amino acid sequence of an exemplified phenolic acid esterase polypeptide and signal peptide(s) can be used to identify and isolate additional, nonexemplified nucleotide sequences which will encode functional equivalents to the polypeptides defined by the amino acid sequences given herein or an amino acid sequence of greater than 40% identity thereto and having equivalent biological activity. All integer percents between 40 and 100 are encompassed by the present invention. DNA sequences having at least about 75% homology to any of the ferulic acid esterases coding sequences presented herein and encoding polypeptides with the same function are considered equivalent to thereto and are included in the definition of "DNA encoding a phenolic acid esterase." Following the teachings herein, the skilled worker will be able to make a large number of operative embodiments having equivalent DNA sequences to those listed herein.

The present invention encompasses feruloyl esterase proteins which are characteristic by at least a portion having from at least about 40% amino acid sequence identity with an amino acid sequence as given in SEQ ID NO:18, amino acids 227 to 440 (within the feruloyl esterase protein of Orpinomyces PC-2 of the present invention. All integer percent identities between 40 and 100% are also within the scope of the present invention. Similarly, the present invention encompasses feruloyl esterase proteins having from about 40% to about 100% identity with an amino acid sequence from the group comprising amino acids 581 to 789 of SEQ ID NO:16, amino acids 845 to 1075 of SEQ ID NO:12, amino acids 69 to 286 of SEQ ID NO:14, amino acids 69 to 307 of SEQ ID NO 14, and amino acids 69 to 421 of SEQ ID NO:14. Specifically exemplified feruloyl esterases of the present invention are characterized by amino acid sequences from the group comprising amino acids 227 to 440 of SEQ ID NO:18, amino acids 581 to 789 of SEQ ID NO:16, amino acids 845 to 1075 of SEQ ID NO:12, amino acids 69 to 286 of SEQ ID NO:14, amino acids 69 to 307 of SEQ ID NO:14, and amino acids 69 to 421 of SEQ ID NO:14. Feruloyl esterase proteins of the present invention include those having the following amino acid sequences: SEQ ID NO:18, amino acids 1 to 530; SEQ ID NO:12, amino acids 795 to 1077; SEQ ID NO:16, amino acids 546 to 789; SEQ ID NO:14, amino acids 20 to 286; SEQ ID NO:14, amino acids 20 to 307; and SEQ ID NO:14, amino acids 20 to 421.

Specifically exemplified nucleotide sequences encoding the feruloyl esterase proteins of the present invention include the following: SEQ ID NO:17, nucleotides 1 to 1590; SEQ ID NO:11, nucleotides 2582-3430; SEQ ID NO:15, nucleotides 2164 to 2895; SEQ ID NO:13, nucleotides 158 to 958; SEQ ID NO:13, nucleotides 158 to 1021; SEQ ID NO:13, nucleotides 158 to 1363.

The phenolic acid esterase coding sequences, including or excluding that encoding a signal peptide of this invention, can be used to express a phenolic acid esterase of the present invention in recombinant fungal host cells as well as in bacteria, including without limitation, Bacillus spp., Streptomyces sp. and *Escherichia coli*. Any host cell in which the signal sequence is expressed and processed may be used. Preferred host cells are Aureobasidium species, Aspergillus species, Trichoderma species and *Saccharomyces cerevisiae*, as well as other yeasts known to the art for fermentation, including *Pichia pastoris* [See, e.g., Sreekrishna, K. (1993) In; *Industrial Microorganisms: Basic and Applied Molecular Genetics*, Baltz, R. H., et al. (Eds.) ASM Press, Washington, D.C. 119–126). Filamentous fungi such as Aspergillus, Trichoderma, Penicillium, etc. are also useful host organisms for expression of the DNA of this invention. [Van den Handel, C. et al. (1991) In: Bennett, J. W. and Lasure, L. L. (eds.), *More Gene Manipulations in Fungi*, Academic Press, Inc., New York, 397–428].

BRIEF DESCRIPTION OF THE DRAWINGS

FIG. 1 shows amino acid sequence alignment of the exemplified phenolic acid esterases. Sequences are xylanase Z [XynZ_Clotm, Grépinet et al. (1988) supra], xylanase Y [XynY_Clotm, Fontes et al. (1995) supra] of *C. thermocellum*, xylanase A (XynA_Rumin) of a Ruminococcus sp, and a hypothetical 44-kDa protein of *E. coli* (Genbank Accession Number P31471) (SEQ ID NO:19). Amino acid numbering was the same as in the databases. Dots represent gaps introduced to optimize alignment, and are treated as mismatched in calculations of sequence relatedness (similarity or identity). The partial amino acids are derived from SEQ ID NO:20, SEQ ID NO:12, SEQ ID NO:16, SEQ ID NO 19 and SEQ ID NO:18.

FIG. 4 presents amino acid sequence alignment of family VI cellulose binding domains. Sequences are xylanase U (XynU_Clotm), xylanase V (XynV_Clotm) (Fernandes et al., 1998, Genbank Accession Number AF047761), and xylanase Z [XynZ_Clotm, Grépinet et al. (1988) supra] of *C. thermocellum* and xylanase A [XynA_Closr, Sakka et al. (1993) *Biosci. Biotech. Biochem.* 57:273–277; Sakka et al. (1996) *Ann. NY Acad. Sci.* 782:741–751 ] of *C. stercorarium*. The sequences presented are portions of those sequences presented in SEQ ID NO:12, SEQ ID NO:14 and SEQ ID NO:24.

FIG. 9 shows alignment of protein sequences exhibiting homology to the Orpinomyces feruloyl esterase. Sequences are: faea_orpin, Orpinomyces sp. strain PC-2 FaeA; xyna_rumin, xylanase from Ruminococcus sp. (Genbank Accession Number S58235); yiel_ecoli hypothetical 44kDa protein from *E. coli* (Genbank Accession Number P31471); xyny_clotm, xylanase Y from *C. thermocellum* (Genbank Accession Number P51584); xynz_clotm, xylanase Z from *C. thermocellum* (Genbank Accession Number M22624); dppv_asprf, dipeptidyl peptidase from *A. fumigatus* (Genbank Accession Number L48074) (SEQ ID NO:20). The partial sequences are taken from SEQ ID NO:18, SEQ ID NO:16, SEQ ID NO:22, SEQ ID NO:12, SEQ ID NO:14 and SEQ ID NO:20.

FIG. 10 is a schematic diagram of the faeA gene from Orpinomyces PC-2.

DETAILED DESCRIPTION OF THE INVENTION

Figure 2:
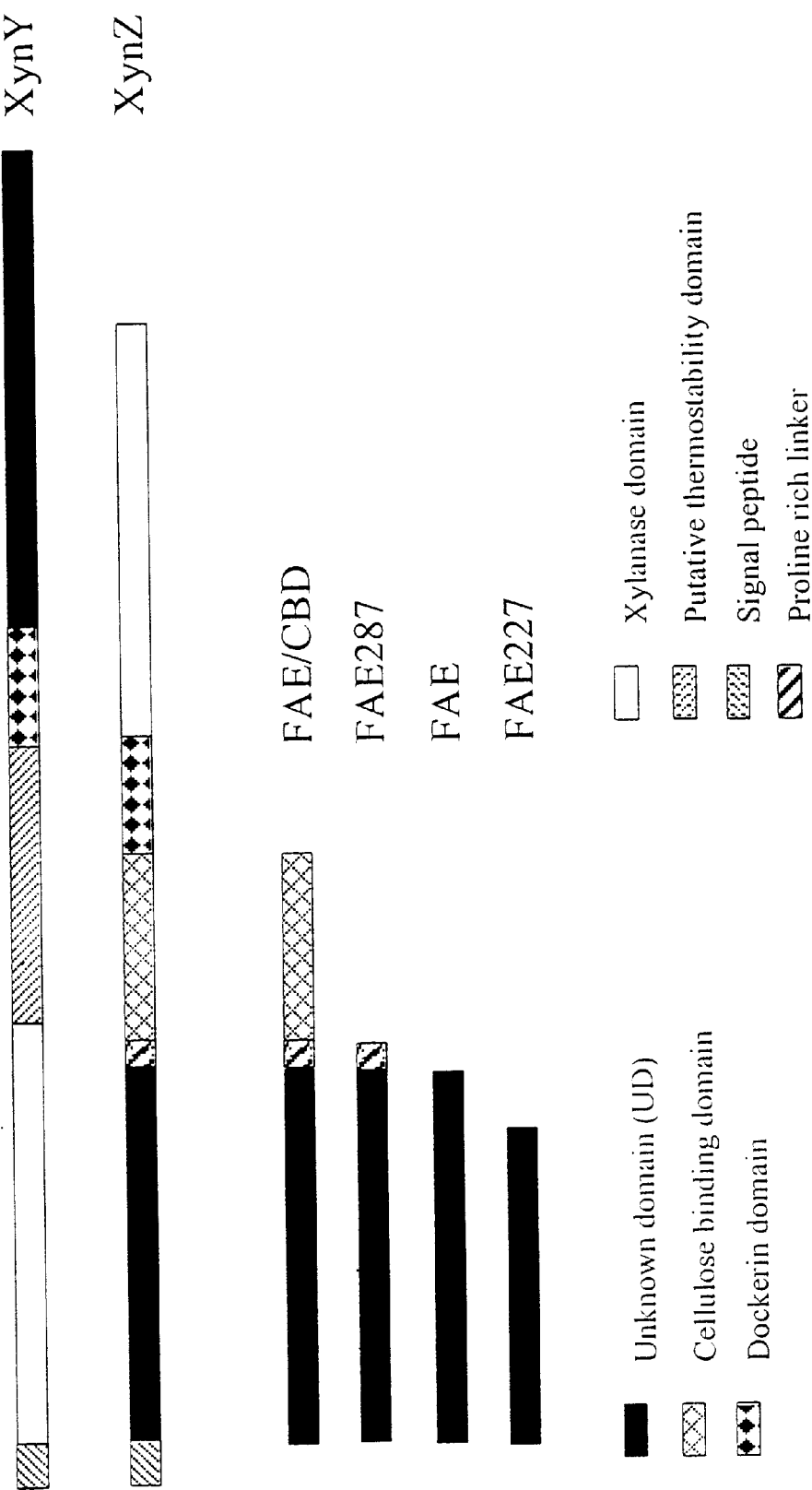
FIG. 2 shows the domain organizations of two cellulosomal components, xylanase Y and xylanase Z of *C. thermocellum*.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Trp, Tryptophan; and Y, Tyr, Tyrosine.

Additional abbreviations used in the present specification include the following: aa, amino acid(s); bp, base pair(s); CD, catalytic domain(s); GCG, Genetics Computer Group, Madison, Wis.; CMC, carboxymethyl cellulose; FPase, filter paper-ase; HMWC, high-molecular weight complex(es); IPTG, isopropyl-β-D-thiogalactoside; OSX, oat spelt xylan; ORF, open reading frame; RBB, remazol brilliant blue; pfu, plaque forming units, FAXX, (0-{5-0-[(E)-feruloyl]-α-L-arabinofuranosyl}(1→3)-0-β-D-xylopyranosyl-(1→4)-D-xylopyranose.

Genes encoding feruloyl esterase (faeA) have been cloned from *Aspergillus niger* and *Aspergillus tubingensis* and the deduced amino acid sequences bear close similarity to lipases [de Vries et al. (1997) *Appl. Environ. Microbiol.* 63:4638–4644]. Expression of these gene products is regulated by the xlnR gene product [van Peij et al. (1998) *Appl. Environ. Microbiol.* 64:3615–3619]. Other genes include the xylD gene from *Pseudomonas fluorescens* subsp. *cellulosa*, the gene product of which has a higher specificity for acetyl groups than feruloyl groups [Ferreira et al. (1 993) *Biochemical J.* 294:349–355] and two genes from *Butyrivibrio fibrisolvens* termed cinA and cinB [Dalrymple and Swadling (1997) *Microbiology* 143:1203–1210; Dalrymple et al. (1996) *FEMS Microbiol. Lett.* 143:115–120]. These genes are believed to be regulated by the cinR gene product which may itself be regulated by FAXX [Dalrymple and Swadling (1997) supra]. Esterase activity has also been studied in *Streptomyces olivochromogenes* [Faulds and Williamson (1991) *J. Gen. Microbiol.* 137:2339–2345], *Schizophyllum commune* [MacKenzie and Bilous (1988) *Appl. Environ. Microbiol.* 54:1170–1173], *Penicillium pinophillum* [Castanares and Wood (1992) *Biochem. Soc. Trans.* 20:275S], and *Fibrobacter succinogenes* [McDermid et al. (1990) *Appl. Environ. Microbiol.* 56:127–132].

As described herein, feruloyl esterases are found as part of xylanases from the *Clostridium thermocellum* cellulosome or as an individual enzyme, for example, from Orpinomyces sp. PC-2. Xylanases Y and Z from *C. thermocellum* are composed of a xylanase domain, a linker domain, and other domains as well as a domain to which no function has been assigned. We found partial sequence homology between these enzyme and the feruloyl esterase of Orpinomyces in the region of the previously unknown domains and demonstrated that these domains indeed encode feruloyl esterases. Herein, we also report the purification, cloning, and partial characterization of the feruloyl esterase from Orpinomyces sp. strain PC-2.

Figure 1:
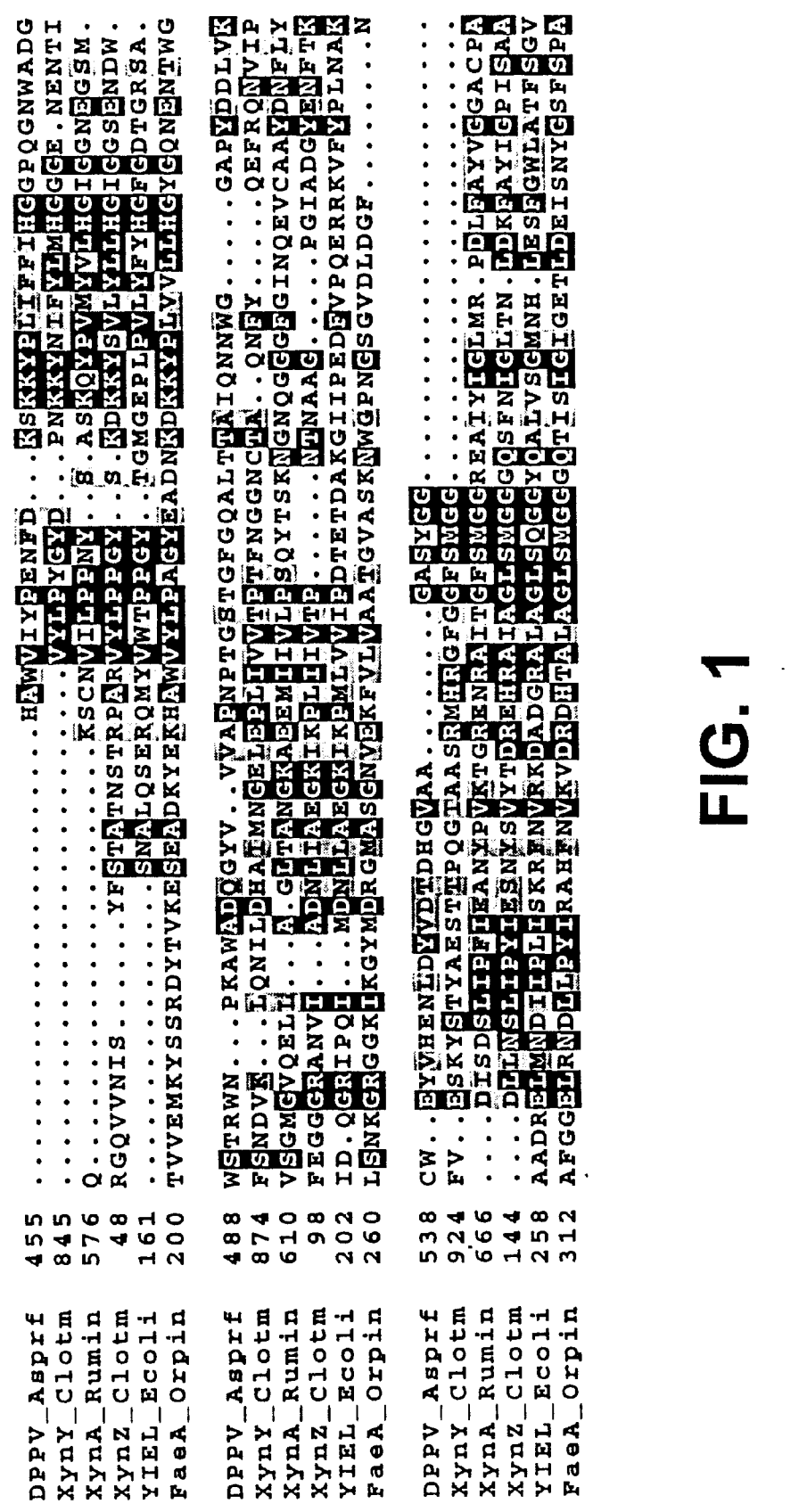

Anaerobic fungi produce high levels of phenolic esterases [Borneman and Akin (1990) In: *Microbial and Plant Opportunities to Improve Lignocellulose Utilization by Ruminants*. D. E. Akin, L. G. Ljungdahl, J. R. Wilson, and P. J. Harris (Eds.). Elsevier Science Publishing Co. New York, pp. 325–340] and two feruloyl esterases of the anaerobic fungus Neocallimastix MC-2 were purified and characterized [Borneman et al. (1992) *Appl. Environ. Microbiol.* 58:3762–3766]. A cDNA coding for a feruloyl esterase (FaeA) of the anaerobic fungus Orpinomyces PC-2 was cloned and sequenced by the present inventors. FASTA and BLAST searches showed that the catalytic domain of the Orpinomyces FaeA was over 30% identical to sequences coding for unknown domains (UD) in the databases including the carboxy terminal region of XynY Fontes et al. (1995) supra], the amino terminal region of XynZ [Grépinet et al. (1988) supra], a hypothetical polypeptide of *E. coli* (Genbank Accession Number P31471), and the carboxy terminal region of a Ruminococcus xylanase [Genbank Accession No. S58235] (FIG. 1). No function had been previously assigned to the sequences homologous to the Orpinomyces FaeA. XynY consists of multiple domains including a family F xylanase domain, followed by a putative thermostability domain, a dockerin, and the UD [Fontes et al. (1995) supra]. Similarly, XynZ is also multi-domain enzyme containing the UD, a family VI cellulose binding domain, a dockerin, and a family 10 xylanase domain [Grépinet et al. (1988) supra; Tomme et al. (1995) In: *Enzymatic Degradation of Insoluble Carbohydrates*. J. N. Saddler, M. H. Panner (Eds.), ACS Symposium Series, American Chemical Society, Washington, D.C., pp. 142–163]. Both XynY and XynZ are believed to be components of the cellulosome (FIG. 2). The Orpinomyces FaeA together with those homologous sequences, however, failed to show significant homology to the recently published feruloyl esterases (FaeA) of *Aspergillus niger* and *A. tubingensis* [de Vries et al. (1997) supra]. The sequence analysis implies that a new type of feruloyl esterase is encoded by the Orpinomyces cDNA and the homologous sequences described above.

We have determined that *C. thermocellum* produces feruloyl esterase activity under the conditions when the cellulosome production is induced. The bacterium was cultivated on low concentration (0.2%, w/v) of Avicel, and under this growth condition, most of the substrate was consumed and cellulosomes released into culture medium, as indicated by the activities on Avicel and xylan (Table 2). Most of the feruloyl esterase activity (97.9%) was found in the culture medium (Table 2). It is well documented that cellulosomes of *C. thermocellum* are readily adsorbed to cellulose [Morag et al. (1992) *Enzyme Microb. Technol.* 14:289–292; Choi and Ljungdahl (1996) *Biochemistry* 35:4897–4905], and thus Avicel adsorption was used to assess association of the feruloyl activity with cellulosomes. As shown in Table 2,97.1% of total feruloyl activity was removed from the culture medium by Avicel treatment, even higher than the percentages of cellulase (80.5%) and xylanase (73.3%) activities removed. These data indicate that feruloyl esterases produced by *C. thermocellum* possess cellulose-binding ability through either a cellulose-binding domain or the cellulosomes. XynZ has a family VI cellulose binding domain [Grépinet et al. (1988) supra; Tonmme et al. (1995) supra] and a docking domain between the CBD and the dockerin, whereas XynY contains a docking domain.

Figure 3:
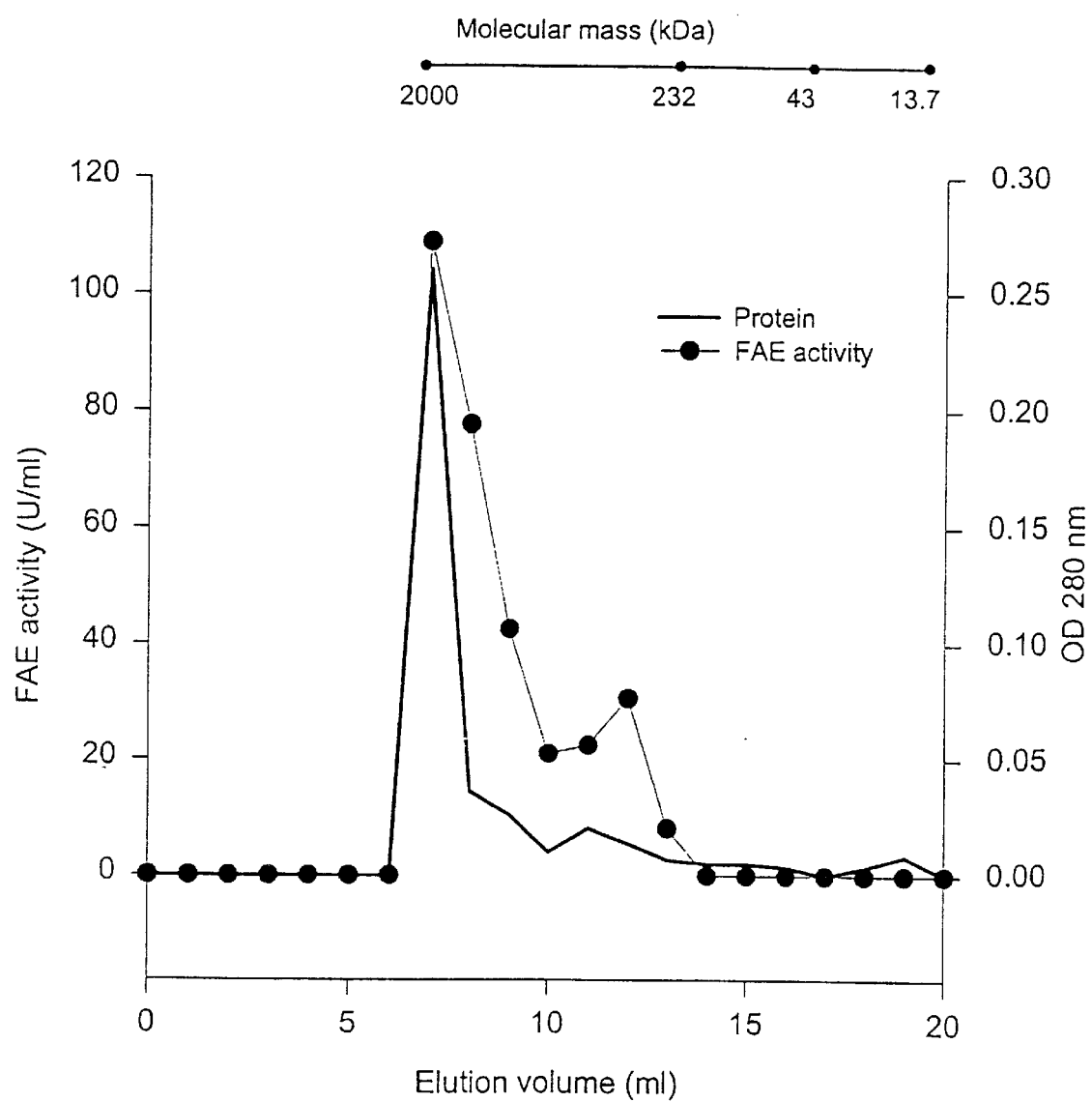
FIG. 3 illustrates the results of Superose 6 gel filtration of proteins eluted from Avicel adsorption of *C. thermocellum* culture supernatant. Fractions (0.5 ml) were collected and assayed for protein and feruloyl esterase activity. Molecular mass standards (Sigma Chemical Company, St. Louis, Mo.) including blue dextran (2,000 kDa), catalase (232 kDa), ovalbumin (43 kDa), and ribonuclease A (13.7 kDa) were run under identical conditions and their elution positions were indicated.

Cellulosomes eluted from Avicel adsorption were analyzed by gel filtration chromatography using a Superose 6 column to assess the sizes of proteins containing feruloyl esterase activity in the native state. The majority of the proteins were eluted in fractions containing molecules with sizes around 2.0 million daltons (FIG. 3), characteristic of cellulosomes eluted from gel filtration [Choi and Ljungdahl (1996) supra]. Feruloyl esterase activity in the fractions correlated well with fractions of cellulosomes. No activity was found in fractions with protein molecules less than 200 kDa, indicating that feruloyl esterase activity resides in the cellulosome.

The UD coding region of XynY and various regions of XynZ were over-expressed in *E. coli* using the pRSET system (Invitrogen, Carlsbad, Calif.). Constructs spanning the XynY UD sequence, XynZ UD alone, and UD plus the CBD sequence in PRSET gave high levels of feruloyl esterase activity whereas cell-free extracts of *E. coli* harboring the pET-21b recombinant plasmid failed to hydrolyze FAXX. Constructs with 20 and 40 amino acid residues deleted from the C-terminus of the Xynz UD did not hydrolyze FAXX, indicating that XynZ sequence from the end of the signal peptide up to amino acid 288 was required to form an active feruloyl esterase. The heterologous protein band of the UD constructs without IPTG induction on SDS-PAGE analysis reached 40–50% of total protein. Both growth rates and levels of feruloyl activity of the constructs with the XynY and XynZ sequences were lower with IPTG induction than without induction. Without wishing to be bound by theory, it is believed that low level of T7 polymerase in *E. coli* BL21 (DE3) strain was ideal for the expression of the inserted genes in pRSET B, and over-expression of T7 polymerase gene by IPTG induction resulted in toxic levels of feruloyl esterase production.

Amino acid residues 328 to 419 of XynZ were homologous to two repeated CBDs of *C. stercorarium* XynA [Sakka et al. (1993) supra; Sakka et al. (1995) supra] (FIG. 4). This domain has been recently classified as a family VI CBD [Tomme et al. (1995) supra]. Constructs containing the UD alone and both the UD plus the putative CBD of XynZ were purified from recombinant *E. coli* cultures. The majority of feruloyl esterase activity of the polypeptide containing both domains was removed by Avicel and acid swollen cellulose adsorption but not with the UD alone, indicating that strong cellulose binding capability resides in the family VI cellulose binding domain of XynZ. Cellulose-binding ability was confirmed with native gel retardation analysis.

Figure 6A:
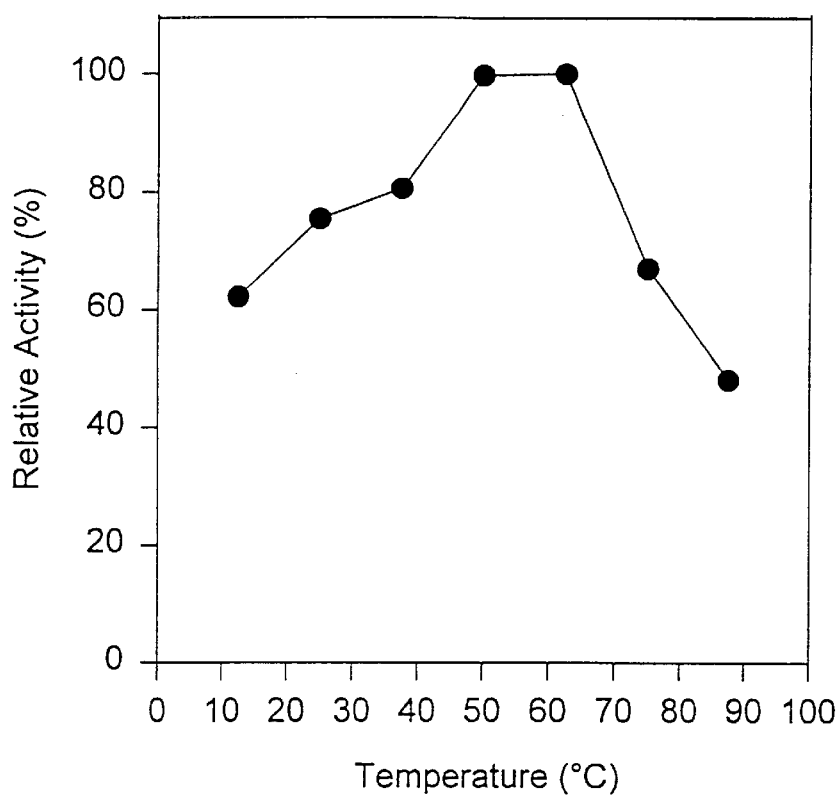
FIGS. 6A and 6B, respectively, illustrate the effects of temperature and pH on feruloyl esterase activity of the *C. thermocellum* XynZ FAE/CBD. Buffer used for evaluating temperature effects was 50 mM sodium citrate, pH 6.0. Assays mixtures with a pH range from 2 to 10 were formulated by using a universal phosphate buffer system.
Figure 6B:
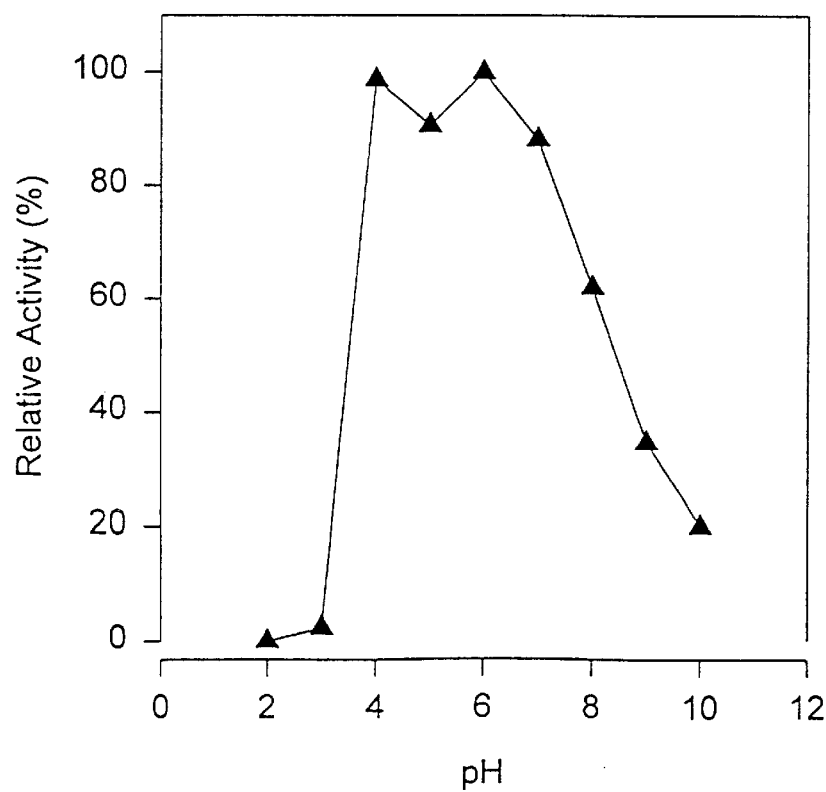

The polypeptide of the Fae domain plus CBD (FAE/CBD) has been purified from *E. coli* cell free extract to almost homogeneity after a single step of heating at 70° C. for 30 min. Over 200 milligrams of the FAE/CBD were obtained from 2.5 gram crude proteins (Table 3). The purified FAE/CBD had a mass of 45 kDa as revealed by SDS-PAGE (FIG. 6), consistent with the calculated size (46.5 kDa). This size was also consistent with what was seen on gel filtration. There was no evidence for aggregation of the recombinant polypeptides produced in *E. coli*.

The purified protein had a Vmax of 13.5 $\mu$mol ferulic acid released min-1 mg-1 and Km of 3.2 $\mu$M using $FAX_3$ as substrate. The enzyme had the highest specific activity toward FAXX, but it was almost as active as toward $FAX_3$ (Table 4). The protein released low levels of ferulic acid from ethyl ferulic acid, ground wheat bran, and Coastal Bermuda grass and p-coumaroyl acid from $PAX_3$ and ethyl-p-coumaroyl acid. The protein lacked activity toward CMC, Avicel, p-nitrophenyl (pNP)-arabinopyranoside, pNP-glucopyranoside, pNP-xylopyranoside, and pNP-acetate.

The recombinant FAE/CBD enzyme had high levels of activity between pH 3.8 and 7 and temperatures between 37 and 65° C. (FIG. 6). The FAE/CBD was stable at temperatures up at 65° C. for 6 hours.

In order to understand how microorganisms breakdown plant cell wall material, we chose to study enzymes from *Clostridium thermocellum*. In particular, XynY and XynZ from this organism were originally thought to contain a xylanase domain and second domain of unknown function. We have now demonstrated that the function of this domain is that of a feruloyl esterase. We believe this is the first report of a phenolic acid esterase in the cellulosome. Feruloyl esterases are important for the complete degradation of plant cell wall material. These enzymes are produced by several organisms, but they have not been found in a bifunctional enzyme.

A feruloyl esterase from Orpinomyces PC-2 was purified and internal fragments of the enzyme were used to screen the Orpinomyces PC-2 cDNA library. A partial clone was sequenced and showed homology to XynZ. A BLAST analysis showed that this enzyme, along with XynY, had domains of unknown function.

The high temperature stability of the enzyme is surprising because no other thermophilic feruloyl esterases have been reported until the present disclosure of the *C. thermocellum* thermotolerant feruloyl esterases. The Orpinomyces PC-2 enzyme has substrate specificity for both feruloyl and p-coumaroyl esterified substrates. The clostridial enzymes are the first from bacteria to have such a dual role. Although the Orpinomyces enzyme is not a true p-coumaroyl esterase, no p-coumaric acid esterases have been found in bacteria to date.

Applications for the enzymes of the present invention include producing ferulic acid from wheat bran or agricultural byproducts, using the enzyme to treat grasses or other plant materials used in the pulp and paper industries, feed processing, and as a food additive. These thermostable enzymes have advantages over other enzymes since they are economically and easily purified, they have high temperature optima, good thermostability, and they are stable over a wide range of pH values.

Feruloyl esterases and xylanase act synergistically to the release of ferulic acid and reducing sugars from lignocellulosic material [Borneman et al. (1993) supra]. In *C. thermocellum* XynY and Xynz, we hypothesize that this is more efficient due to the incorporation of both enzymes into one. We believe there is a multicutting event catalyzed by these enzymes much like the multicutting event in the cellulosome itself which leads to more efficient hydrolysis of plant cell wall material. The substrate, arabinoxylan could be passed from one active site to another, which would eliminate the process of each of two enzymes having to bind to the substrate and then release it for the other enzyme to attack.

XynY and XynZ are enzymatic components of the *Clostridium thermocellum* cellulosome. These components have a multi-domain structure which includes a dockerin domain, a catalytic xylanase domain, and a domain of unknown function. The previously unknown domains in XynY and XynZ have been found to have phenolic esterase activity. These domains have some amino acid homology to that of a phenolic esterase from the anaerobic fungus Orpinomyces sp. strain PC-2. Secondly, purified cellulosomes from C. thermocellum hydrolyze (O-{5-O-[(E)-feruloyl]-(-L-arabinofuranosyl}-(1(3)-O-(-D-xylopyranosyl-(1(4)-D-xylopyranose) (FAXX) and {5-O-[(E)-feruloyl]-[O-(-D-xylopyranosyl-(1(2)]-O-(-L-arabinofuranosyl-[1(3]}-O-(-D-xylopyranosyl-1(4)-D-xylopyranose (FAX$_3$) yielding ferulic acid as a product, thus indicating the presence of a phenolic acid esterase. Intracellular and extracellular fractions lacking cellulosomes had insignificant amounts of phenolic acid esterase activity which confirmed that the activity resided with the cellulosome. The final proof was obtained by cloning the domains of XynY and XynZ into *Escherichia coli*. The domains were expressed and found to possess phenolic acid esterase activities with FAXX and FAX$_3$ as substrates.

Nucleotides corresponding to regions of DNA encoding amino acids in XynZ (Genbank Accession Number M22624) from 20–421 and in XynY (Genbank Accession Number X83269) from 795–1077 were overexpressed in *E. coli* using the pET and pRSET systems respectively. The XynZ sequence will henceforth be referred to as XynZ FAE/CBD since it incorporates the family VI CBD, and the XynY protein is XynY FAE since it only contains a catalytic domain. The cell free extracts containing the expressed proteins each hydrolyzed FAXX with release of ferulic acid (FA) which suggests that these proteins are feruloyl esterases. The expressed protein from the construct containing XynY FAE had a molecular weight of 31 kDa, consistent with the sequence data. Constructs containing XynZ FAE/CBD produced a protein with a molecular mass of 45 kDa as analyzed by SDS-PAGE. The protein was expressed without IPTG induction at a level of 8% of the total protein. Levels of feruloyl esterase activity of the constructs with the XynY FAE and XynZ FAE/CBD sequences were lower with IPTG induction than without induction. Since these proteins had similar sequences and similar function coupled with the fact that XynZ had higher expression levels than XynY, we decided to focus our attention on XynZ and subsequent experiments will refer to that protein.

Constructs were made which corresponded to proteins with amino acids from the original *C. thermocellum* XynZ sequence of 20–307 (FAE287), 20–286 (FAE) and 20–247 (FAE227) (with reference to SEQ ID NO. 14 and FIG. 2). FAE287 is missing the CBD, but contains a proline rich linker which separates the CBD from the FAE domain while FAE does not contain this linker. When these constructs were expressed in *E. coli* in the same manner as XynZ FAE/CBD, they both exhibited feruloyl esterase activity. Thus, the removal of the 114 amino acids of the C13D did not have a detrimental effect on the activity. XynlZ FAE/CBD bound to acid swollen cellulose very weakly, while the other constructs missing the CBD did not bind acid swollen cellulose at all. FAE227 was an inactive but expressed enzyme. The data here show that neither the CBD nor the linker is necessary for activity, but amino acids 247–266 are necessary for generation of an active enzyme. Since neither the linker region nor the CBD is necessary for activity, we used the smallest construct which still retained activity, FAE, for subsequent experiments.

Figure 5:
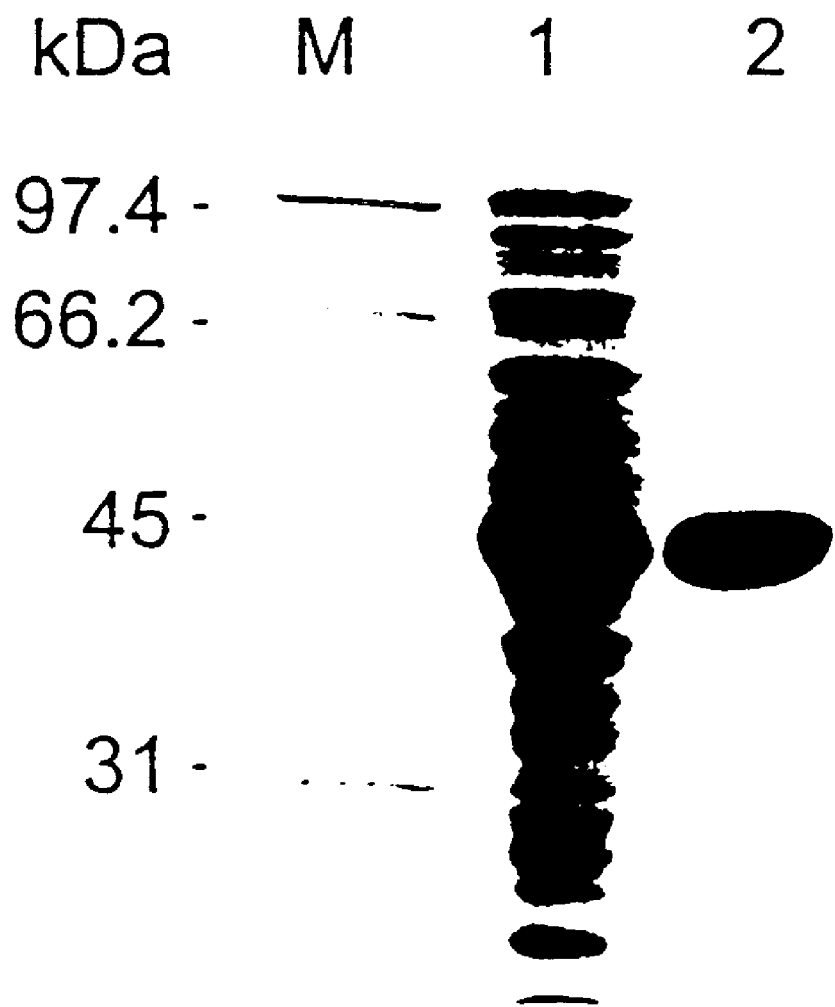
FIG. 5 shows the results of SDS-PAGE analysis of the *C. thermocellum* XynZ ferulic acid esterase+cellulose binding domain (FAE/CBD) over-expressed in *E. coli*. Lane M, low range protein standard markers (Bio-Rad Laboratories, Hercules, Calif.) including phosphorylase B (97.4 kDa), serum albumin (66.2), ovalbumin (45 kDa), and carbonic anhydrase (31 kDa) lane 1, *E. coli* cell free extract; lane 2, heat-treated cell free extract.

The XynZ FAE/CBD polypeptide was purified from *E. coli* cell free extract after a single step of heat treatment at 70° C. for 30 min. Over 200 mg of the XynZ FAE/CBD were obtained from 2.5 gram of crude protein (Table 3). The purified XynZ FAE/CBD had a mass as stated previously of 45 kDa as revealed by SDS-PAGE (FIG. 5), consistent with the calculated size (46.5 kDa). There was no evidence for aggregation of the feruloyl esterase produced in *E. coli*, and SDS-PAGE gels showed that protein which was removed from the cell free extract by centrifugation had no insoluble protein which could be attributed to inclusion bodies.

The purified protein had a Vmax of 12.5 $\mu$mol ferulic acid released min-1 mg-1 and Km of 5 mM using FAX3 as substrate. The enzyme had the highest specific activity towards FAXX but was almost as active toward FAX3 (Table 4). The protein was able to release low levels of FA from ethyl ferulic acid, ground wheat bran, and Coastal Bermuda grass and p-coumaric acid (PCA) from PAX3 and ethyl-p-coumarate. The protein lacked activity toward CMC, Avicel, p-nitrophenyl (pNP)-arabinopyranoside, pNP-glucopyranoside, pNP-xylopyranoside, and pNP-acetate. Isoelectric focusing gel electrophoresis showed that the protein had a pl of 5.8.

The FAE polypeptide of XynZ was also expressed and purified to homogeneity. A purification scheme is shown in Table 3B. The protein was expressed in a manner similar to that for XynZ FAE/CBD. The heat treatment step also resulted in 200 mg of protein, but the protein was not pure. An additional step involving gel filtration resulted in a pure enzyme with a Vmax of 28.2 $\mu$mol ferulic acid released min-1 mg-1 and Km of 10.5 mM using FAX3 as substrate. FAE was inhibited by ferulic acid but not by xylose or arabinose. The FAE had a temperature optimum between 30° and 70° C. (FIG. 6A) and had high level activity between pH 4 and 7 (FIG. 6B) The enzyme was stable at temperatures up at 70° C. for 6 hours, and in a similar experiment, FAE/CBD also was stable at 70° C. At 80° C., the relative activity of FAE decreased to around 50% after three hours of incubation, and most of the relative activity was destroyed after 1 hour of incubation at 90° C.

Anaerobic microorganisms do not readily degrade lignin, but are able to solubilize it. Anaerobic fungi are able to solubilize but not metabolize lignin, and it is suggested that the released lignin was carbohydrate linked [McSweeney et al. (1994) *Appl. Environ. Microbiol.* 60:2985–2989]. The data herein indicate that feruloyl esterases are responsible for lignin solubilization. Most studies of the cellulosome of *C. thermocellum* has been directed toward its cellulolytic activity. It also has xylanases which we have shown are bifunctional enzymes with feruloyl esterase activity. The cellulosome should be efficient in the degradation of arabinoxylan. It has been previously shown that *Clostridium xylanolyticum* released aromatics into the culture medium when grown on lignocellulosic material [Rogers et al. (1992) *International Biodeterioration & Biodegradation* 29:3–17].

XynY and XynZ each contain a glycosyl hydrolase family 10 catalytic domain in addition to the FAE catalytic domain. The xylanase domain of XynZ has been well studied, that construct has been crystallized, and the three dimensional structure solved [Dominguez et al. (1995) *Nat. Struct. Biol.* 2:569–576; Souchon et al. (1994) *J. Mol. Biol.* 235:1348–1350]. In general, xylanases are thought to be sterically hindered by groups substituted on the xylan backbone. Feruloyl esterase and xylanase have been shown to act synergistically for the release of ferulic acid and reducing sugars from lignocellulosic material [Borneman et al. (1993) supra]. In XynY and XynZ we hypothesize that this event has been made more efficient by the incorporation of both FAE and xylanase catalytic domains into one enzyme. Without wishing to be bound by theory, we believe that there is a multicutting event catalyzed by these enzymes much like the multicutting event in the cellulosome itself which leads to more efficient hydrolysis of plant cell wall material. Bifunctional enzymes like XynY and XynZ form a dumbbell-like shape which attacks the arabinoxylan polysaccharide and the substrate is passed from one active site to another, eliminating the relatively inefficient two enzyme process in which one has to bind to the substrate and then release it for the other enzyme to attack. The existence of multidomain enzymes such as the sea whip coral peroxidase-lipoxygenase [Koljak et al. (1997) *Science* 277:1994–1996] and a xylanase-β(1,3-1,4)-glucanase from *Ruminococcus flavifaciens* [Flint et al. (1993) *J. Bacteriol.* 175:2943–2951] suggests an evolutionary importance of having two or more catalytic domains in one enzyme. XynZ contains a contains a family VI CBD, which does not bind cellulose significantly. However, representatives of CBDs of this family usually efficiently bind xylan. The CBD of XynZ may participate in a tight association of the catalytic domains with the substrate. This is consistent with the higher Km of FAE as compared to that of XynZ FAE/CBD.

Both FAE/CBD and FAE are highly thermostable. They are active against both feruloyl and p-coumaroyl esterified substrates, and they represent the first FAE from bacteria to hydrolyze p-coumaroyl esters. The high Km of FAE versus XynZ FAE/CBD indicates that the CBD is important in binding the substrate before enzyme catalysis.

The FAE domains of XynZ and XynY are homologous to each other and to the Orpinomyces FaeA. The Orpinomyces FaeA, together with those homologous sequences, however, failed to show significant homology to the recently published feruloyl esterases (FaeA) of *Aspergillus niger* and *A. tubingensis* [de Vries et al. (1997) supra] as well as CinA and CinB from *Butyrivibrio fibrisolvens* [Dalrymple et al. (1996) *FEMS Microbiol. Lett.* 143:115–120; Dalrymple and Swadling (1997) *Microbiology* 143:1203–1210] and XylD from *Pseudomonas fluorescens* subsp. *cellulosa* [Ferreira et al. (1993) *Biochemical Journal* 294:349–355]. The sequence analysis implies that a new type of feruloyl esterase is encoded by the Orpinomyces gene and the homologous *C. thermocellum* sequences described above. The Orpinomyces FaeA, and the FAE domains of XynZ and XynY were also shown to be homologous to a hypothetical polypeptide of *E. coli* (Genbank Accession Number P31471) and the carboxy terminal region of a Ruminococcus sp. xylanase earlier designated as a UD [Genbank Accession Number S58235]. No function had been assigned to those sequences of *E. coli* and Ruminococcus. Without wishing to be bound by theory, the present inventors believe that these sequences also encode feruloyl esterases and that the Ruminococcus xylanase is also bifunctional. Ruminococcus has been shown to produce FAE activity [McSweeney et al. (1998) *Anaerobe* 4:57–65], and another Ruminococcus xylanase has been shown to be a bifunctional enzyme with xylanase and acetyl xylan esterase activity [Kirby et al. (1998) *Biochemical Society Transactions* 26:S169]. No feruloyl esterase activity has been observed in *E. coli*. The gene from *E. coli* may encode a dipeptidase instead, because homology exists between a dipeptidase from *Aspergillus fumigatus* and feruloyl esterases. The data suggest a common ancestral encoding feruloyl esterases from Orpinomyces, *C. thermocellum*, and Ruminococcus.

Potential applications for the enzymes of the present invention include producing ferulic acid from wheat bran or agricultural byproducts, using the enzyme to treat grasses which are used in the pulp and paper industry, feed processing, and as a food additive. These thermostable enzymes have advantages over other enzymes because they are easy to purify, have high temperature optima and are stable over a wide pH range.

The feruloyl esterase domain of XynZ was highly expressed in *E. coli* and the esterase comprised 40–50% of the total cell protein. The recombinant esterase of XynZ was purified to almost homogeneity by heat treatment. The protein had a molecular mass of 45 kDa, consistent with the size of the predicted deduced amino acid sequence. Of the substrates tested, the expressed protein had high specific activity towards FAXX and $FAX_3$. With $FAX_3$ as a substrate Km and Vmax values were 3.2 mM and 13.5 μmol ferulic acid released mind mg-I respectively at pH 6.0 at 60° C. Several phenolic esterified substrates were hydrolyzed and the specific activities with those containing feruloyl groups were higher than were those with p-coumaroyl groups confirming that the previously unknown domain of XynZ is a feruloyl esterase. The enzyme released mainly ferulic acid from wheat bran and Coastal Bermuda grass (CBG) with a smaller amount of p-coumaroyl groups released from CBS. This study represents the first demonstration of esterases in the cellulosome of *Clostridium thermocellum* and of enzymes from the cellulosome with two different activities. The present work also provides a phenolic acid esterase derived from a xylanase from Ruminococcus and as an enzyme produced by Orpinomyces PC-2.

Figure 7:
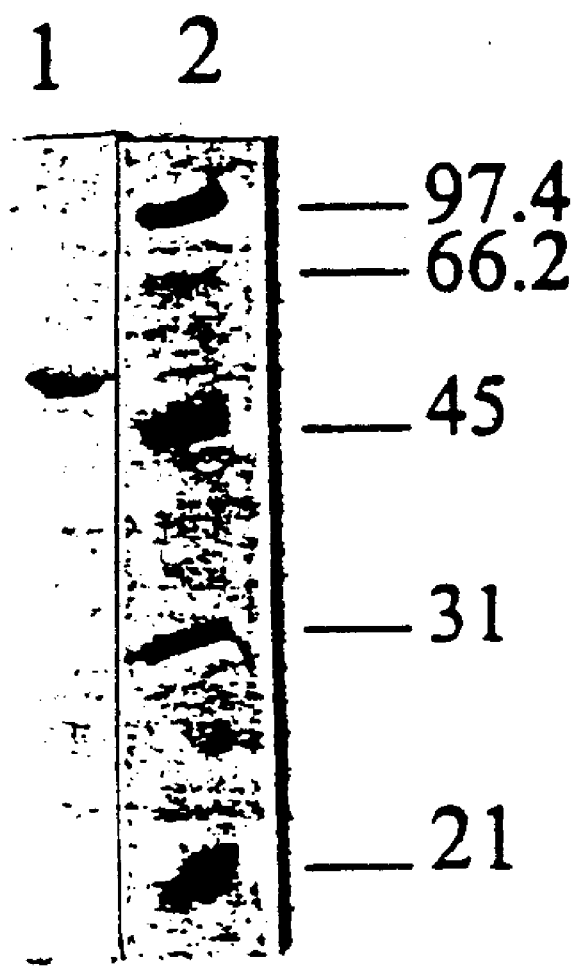
FIG. 7 illustrates the results of SDS-PAGE analysis of the purified feruloyl esterase from the culture supernatant of Orpinomyces sp. strain PC-2 (lane 1); molecular mass markers are in lane 2.

A summary of the purification of FAE from Orpinomyces sp stain PC-2 is presented in Table 7. The Q-Sepharose column separated two peaks of esterase activity. Proteins which eluted in the first peak had higher activity against ethyl-pCA while proteins eluting in the second peak had greater activity against FAXX. These data suggest that a p-coumaroyl esterase eluted in the first peak while the feruloyl esterase eluted in the second. The first peak was not studied further, but the fractions in peak 2 were further purified resulting in a purified enzyme which had an approximate molecular mass of 50 kDa as visualized by SDS-PAGE analysis (FIG. 7). There was a decrease in specific activity after the MonoQ step which could not be explained.

Figure 8B:
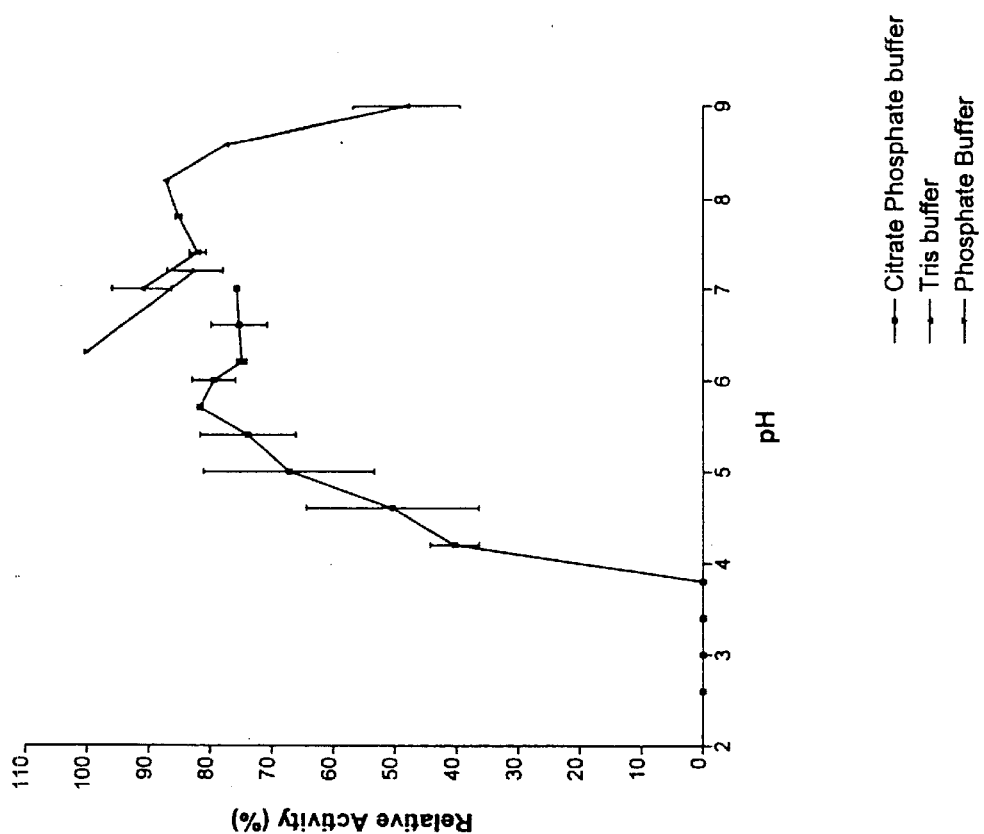
FIGS. 8A and 8B show the temperature and pH activity profiles, respectively, of the Orpinomyces sp. strain PC-2 feruloyl esterase.
Figure 8A:
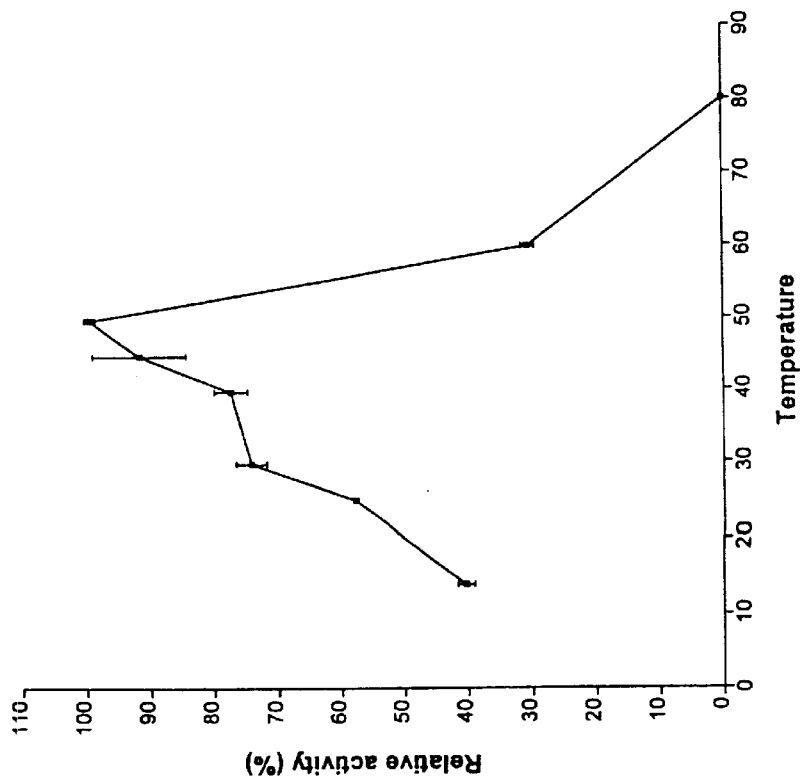
Figure 11:
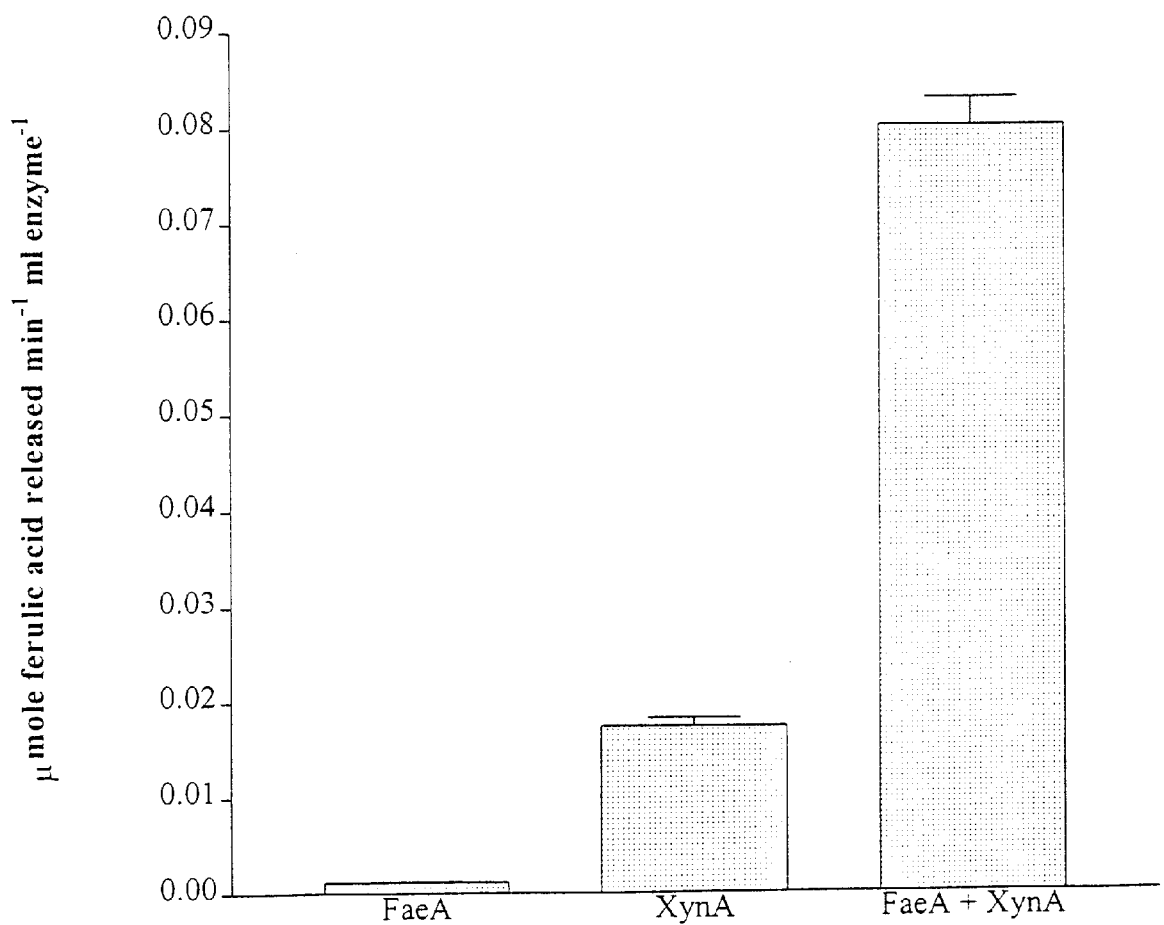
FIG. 11 illustrates the synergistic effects of the Orpinomyces FaeA and XynA on the release of ferulic acid from wheat bran as substrate.

Temperature and pH optima experiments showed that the enzyme had a temperature optimum of 50° C. (FIG. 8A) and had activity over a pH range between 5.2 and 8 (FIG. 8B). The purified enzyme was stable at 4° C. for over 18 months. The purified enzyme was subjected to N-terminal sequencing giving the sequence ETTYGITLRDTKEKFTVFKD (SEQ ID NO:21). The protein was also subjected to internal sequencing which resulted in four peptide fragments (Table 8) which were used to create degenerate PCR primers.

Two of the peptide fragments from the internal amino acid sequencing were used to create degenerate aglionucleotide primers which are listed in the materials and methods section. These primers were used to amplify regions of DNA in the Orpinomyces PC-2 cDNA library. A 216 bp PCR product was generated. The PCR product was labeled with digoxygenin-UTP and used as a probe to screen the cDNA library. After screening 50,000 phage, one positive plaque was obtained and its DNA was sequenced using T3 and T7 universal primers. Sequencing using the T3 primer did not reveal any ORFs, however, sequencing using the T7 reverse primer gave the C-terminal end of the gene. Based on the sequence data and restriction fragment analyses, but without wishing to be bound by theory, we have concluded that the faeA gene in this cDNA was truncated and furthermore that the insert comprises multiple genes. These other genes were not studied further. The deduced amino acid sequence of the insert matched the data from the peptide sequencing. The insert had a size of 1074 bp and encoded a protein of 358 amino acids. Since the size of the encoded protein did not match that of the purified enzyme and the N-terminal sequence, including a signal peptide and lack of a start codon, another round of screening was performed using the entire sequence as a probe after digoxygenin labeling. After screening an additional 50,000 phage, one positive clone was obtained which had a size of 1673 bp with the largest open reading frame comprising a protein of 530 amino acids. The sequence of this insert is believed to be an incomplete one since no 5' UTR was found and the (putative) signal sequence has only four amino acids. Most signal sequences found in hydrolytic enzymes from anaerobic fungi are at least 20 amino acids long. The insert was found to be in a reverse orientation with respect to the LacZ promoter. The upstream lac promoter should direct synthesis of the inserted gene, but no activity was found in lysed *E. coli* cells harboring the recombinant plasmid. The FaeA gene in *E. coli* was expressed using the pET system (Novagen) in the correct orientation. The recombinant FaeA released ferulic acid from FAXX as well as other substrates which were esterified with phenolic groups. The enzyme had the highest activity against FAXX, which demonstrates that it is a true feruloyl esterase (Table 10). In addition, when the enzyme was incubated with a recombinant xylanase, there was a 80 fold increase in FA released over FaeA alone.

Figure 9:
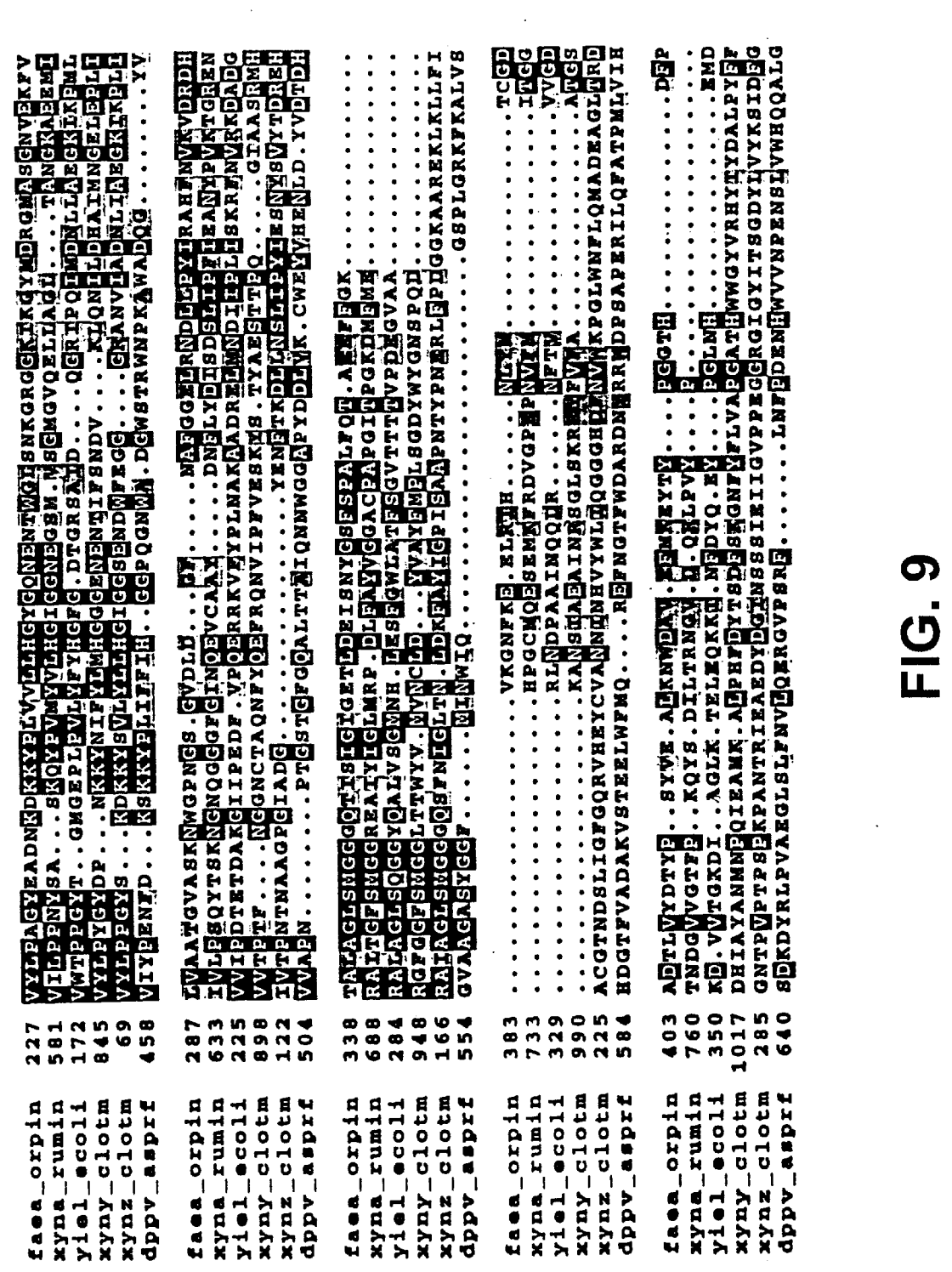

The nucleotide and deduced amino acid sequence of the faeA gene are shown in Table 9. A BLAST analysis of the encoded protein showed homology to several enzymes. These enzymes included domains of unknown function from Xylanase Z and Xylanase Y of *Clostridium thermocellum*, a domain of unknown function in a xylanase from Ruminococcus spp. and a 44 kDa hypothetical protein from *E. coli*, and a dipeptidyl peptidase from *Aspergillus fumigatus* (FIG. 9). All proteins had at least 20% identity with the C-terminal 300 amino acids of the protein. The N-terminal part of the enzyme did not show homology to any enzyme in the BLAST analysis and the function of this domain is unknown. Although FAE activity has been demonstrated in the cellulase/hemicellulase complex from Orpinomyces, this protein does not contain a non-catalytic repeated peptide domain (NCRPD). Analysis of C-terminal coding region indicated a typical signature sequence found in lipases and other esterases of GXSXG at residues 341–345 as well as an aspartic acid at residue 403 and a histidine at residue 436 which would make up the catalytic triad. A search of the sequence revealed two N-glycosylation sites at amino acids 300 and 488 (of SEQ ID NO:18) and a 16mer poly A tail in the 3' UTR.

It will be understood by those skilled in the art that other nucleic acid sequences besides those disclosed herein for the phenolic acid esterases, i.e. feruloyl esterases, will function as coding sequences synonymous with the exemplified coding sequences. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded. It is further understood in the art that codon substitutions to conform to common codon usage in a particular recombinant host cell is sometimes desirable Specifically included in this invention are sequences from other strains of Clostridium and from other microorganisms which hybridize to the sequences disclosed for feruloyl and coumaryl esterases under stringent conditions. Stringent conditions refer to conditions understood in the art for a given probe length and nucleotide composition and capable of hybridizing under stringent conditions means annealing to a subject nucleotide sequence, or its complementary strand, under standard conditions (i.e., high temperature and/or low salt content) which tend to disfavor annealing of unrelated sequences, (indicating about 95–100% nucleotide sequence identity). Also specifically included in this invention are sequences from other strains of Orpinomyces species and other anaerobic fungi which hybridize to the sequences disclosed for the esterase sequences under moderately stringent conditions. Moderately stringent conditions refer to conditions understood in the art for a given probe sequence and "conditions of medium stringency" means hybridization and wash conditions of 50°–65° C., 1×SSC and 0.1% SDS (indicating about 80–95% similarity). Also specifically included in this invention are sequences from other strains of Orpinomyces, from other anaerobic fungi, and from other organisms, including bacteria, which hybridize to the sequences disclosed for the esterase sequences under highly stringent conditions. Highly stringent conditions refer to conditions understood in the art for a given probe sequence and "conditions of high stringency" means hybridization and wash conditions of 65°–68° C., 0.1×SSC and 0.1% SDS (indicating about 95–100% similarity). Hybridization assays and conditions are further described in Sambrook et al. (1989).

A method for identifying other nucleic acids encoding feruloyl esterase- and/or coumaryl esterase-homologous enzymes is also provided wherein nucleic acid molecules encoding phenolic acid esterases are isolated from an anaerobic fungus, including but not limited to Orpinomyces or an anaerobic bacterium, such as Clostridium or Ruminococcus, among others, and nucleic acid hybridization is performed with the nucleic acid molecules and a labeled probe having a nucleotide sequence that includes all or part of a FAE coding sequence as given in Table 5, 6, 9 and/or 10 herein. By this method, phenolic acid esterase genes similar to the exemplified feruloyl and coumaryl esterases can be identified and isolated from other strains of Clostridium or other anaerobic microorganisms. All or part of a nucleotide sequence refers specifically to all continuous nucleotides of a nucleotide sequence, or e.g. 1000 continuous nucleotides, 500 continuous nucleotides, 100 continuous nucleotides, 25 continuous nucleotides, and 15 continuous nucleotides.

Sequences included in this invention are those amino acid sequences which are 40 to 100% identical to the amino acid sequences encoded by the exemplified C. thermocellum strain feruloyl esterase, amino acids proteins truncated from the XynY or XynZ proteins or the Ruminococcus FAE polypeptide or the Orpinomyces PC-2 FAE polypeptide, all specifically identified herein. Sequences included in this invention are also those amino acid sequences which are 40, 50, 60, 70, 75, 80, 85, 90, 95 to 100%, and all integers between 40% and 100%, identical to the amino acid sequences encoded by an exemplified phenolic acid esterase coding sequence and corresponding to or identifying encoded proteins which exhibit feruloyl esterase activity. In comparisons of protein or nucleic acid sequences, gaps introduced into either query or reference sequence to optimize alignment are treated as mismatches. In amino acid sequence comparisons to identify feruloyl esterase proteins, the reference sequence is, desirably, amino acids 227 to 440 of SEQ ID NO:18 (FAE of Orpinomyces PC-2).

It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pp. 345–352, which is incorporated by reference herein provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Monoclonal or polyclonal antibodies, preferably monoclonal, specifically reacting with the phenolic acid esterases of the present invention may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1 993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, New York; Old and Primrose (1981) *Principles of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

Each reference and patent document cited in the present application is incorporated by reference herein to the extent that it is not inconsistent with the present disclosure.

The following examples are provided for illustrative purposes, and is not intended to limit the scope of the invention as claimed herein. Any variations: in the exemplified articles which occur to the skilled artisan are intended to fall within the scope of the present invention.

EXAMPLES

Example 1

Bacterial Strains, Vectors, and Culture Media

C. thermocellum JW20 was cultivated in prereduced liquid medium [Wiegel and Dykstra (1984) *Appl. Microbiol. Biotechnol.* 20:59–65] at 60° C. under an atmosphere of nitrogen. Avicel (microcrystalline cellulose, 0.4% w/v, Baker TLC, 2–20 micron particle size) was used as the carbon source. E. coli strain BL21 (DE3) (Stratagene, La Jolla, Calif.) and plasmid pRSET B (Invitrogen, Carlsbad, Calif.) were used the host strain and the vector for protein expression. Improved results were obtained using plasmid pET-21b (Novagen, Madison, Wis.). The recombinant E. coli were selected for by growing in Luria-Bertani medium containing 100 µg/ml ampicillin.

Example 2

Amplification and Cloning of Sequences Coding for Different Domains of C. thermocellum XynY and XynZ Genomic DNA was isolated from C. thermocellum as previously described [Maniatis et al. (1982) supra]. PCR primers were designed (Table 1) and synthesized on an Applied Biosystems (Foster City, Calif.) DNA sequencer. To facilitate the insertion of DNA sequence into or pET-21b or pRSET B, BamHI (for pET-216) or NdeI for pRSET B, and HindIII sites were added to forward and reverse primers, respectively (Table 1). PCRs were carried out on a Perkin Elmer 480 Thermocycler for 30 cycles with each cycle on 95° C. for 1 min, 48° C. for 1 min, and 72° C. for 3 min. PCR products and the plasmid were digested with BamHI (or NdeI) and HindIII, purified with a Bio101 Geneclean kit, ligated with T4 ligase. E. coli BL21 (DE3) was transformed with the ligation mixture and at least four colonies of each construct were picked for analyzing feruloyl esterase expression. The inserted sequences were sequenced to verify the lack of unwanted mutations.

Two internal sequences were used to create degenerate oligonucleotide primers for PCR in order to amplify the feruloyl esterase coding sequence in the cDNA library in Orpinomyces. The Orpinomyces PC-2 cDNA library is described in the λZAPII vector (Stratagene, La Jolla, Calif.) in E. coli host cells is described in Chen et al. (1995) Proc. Natl. Acad. Sci. 92:2587–2591. Positive clone(s) are subcloned a pBluescript vector (Stratagene, La Jolla, Calif.). The amplified product was cloned into pCRII (Invitrogen, Carlsbad, Calif.) using the TA cloning kit and sequenced using an automatic PCR sequencer (Applied Biosystems, Foster City, Calif.) using M13 reverse primer. The resulting PCR product was used to screen the cDNA library after being labeled with digoxigenin (Boehringer Mannheim, Indianapolis, Ind.). The digoxigenin probe was bound to plaques which were lifted from a nitrocellulose blot. Antibodies conjugated to alkaline phosphatase showed a single positive clone which hybridized to the PCR product. The product was sequenced and found to contain the C-terminal 358 amino acids of the enzyme (See Table 9). A second probe which incorporated those 339 amino acids was used as a probe to screen the library in the same manner as before. A second clone was isolated which contained the C-terminal region plus an additional 172 amino acids making a polypeptide of 530 amino acids. Confirmation of the sequence came from N-terminal and internal protein sequence data from the purified enzyme which matched that of the cloned cDNA product. Expression cloning of this coding sequence, which lacks an ATG translation start site, can be achieved by expressing it, in frame, as a fusion protein using any one of a number of fusion protein vectors known to the art or an ATG translation start codon and/or ribosome binding site upstream of the ATG can be added using methodology well known to and readily accessible to the art in an expression vector appropriate to the choice of recombinant host cell.

Example 3

Isolation and Analysis of the Cellulosome

The cellulosomes were isolated from 10L of culture fluid after complete substrate exhaustion by the affinity digestion method [Morag et al. (1992) supra]. This preparation was used directly for gel filtration using a Fast Protein Liquid Chromatography (FPLC) system with a Superose 6 column (Pharmacia, Piscataway, N.J.). Proteins were eluted in 50 mM Tris-HCl, 100 mM NaCl at a flow rate of 0.2 ml/min. Fractions of 0.5 ml were collected and stored at 4° C. for further analysis. Cell extracts were prepared by first growing the organism in the presence of 0.2% cellobiose for 2 days. Cells were then separated by centrifugation, resuspended in 50 mM Tris-HCl buffer, pH 7.5, and sonicated. Culture medium was concentrated to 5 ml using a Millipore concentrator (Millipore, Bedford, Mass.). To adsorb cellulosomes from the medium, 0.5 mg of Avicel was added and the suspension was stirred at 4° C. for 4 hours. Avicel was removed by centrifugation (Avicel-treated medium). All fractions were tested for Avicelase, xylanase, and ferulic acid esterase activities.

Unless otherwise noted, all C. thermocellum enzyme assays were performed at 60° C. in 50 mM Na-citrate buffer, pH 6.0. One unit of enzyme activity was defined as the amount of enzyme that released 1 μmol of product min-1, and specific activity is given in units per milligram of protein. Feruloyl esterase activity was measured using a modified version of the assay described by Borneman et al. [Borneman et al. (1990) Anal. Biochem. 190:129–133]. The appropriately diluted protein sample (25 l) was added to 400 μl of buffer plus 8 mM of substrate. Samples were incubated at 60° C. for 5 min. and the reaction was stopped by adding 25 μl of 20% formic acid. Release of ferulic acid was measured via HPLC using a mobile phase of 10 mM Na-formate pH 3 and 30% (vol/vol) methanol. For routine assays, FAXX and FAX3 purified from wheat bran were used as substrates [Borneman et al. (1990) supra]. Ethyl-ferulate and ethyl-p-coumarate esters were a gift from D. E. Akin (USDA, Athens, Ga.). The hydrolysis of these (10 mM) were determined similarly to that of FAXX, but the HPLC analyses were performed with 50% methanol. HPLC runs were with a Hewlett Packard 1100 Series instrument equipped with an autosampler and diode array detector. Ferulic acid and p-coumaric acid were used as standards. To determine the amount of feruloyl and p-coumaroyl groups released from plant cell walls, wheat bran and Coastal Bermuda grass were ground in a Wiley mill to pass through a 250 μm screen. Plant samples of ten milligram were incubated for one hour in 400 μl of 50 mM Na-citrate buffer pH, 6.0 plus 25 μl of enzyme. After the addition of 25 μl of 20% formic acid to stop the reaction, the samples were centrifuged at 16,000×g in a microfuge and then assayed for FA and pCA by HPLC.

Assays with p-nitrophenol substrates were performed in microtiter plate wells. Two hundred microliters of substrate at a concentration of 100 μM was preincubated in wells heated to 40C. Enzyme (10 μl) was added to the reaction mixture and the absorbance was followed continuously at a wavelength of 405 nm. p-Nitrophenol was used as standard. Xylanase and Avicelase activities were measured by reducing sugar assays using dinitrosalicylate [Miller, G. L. (1959) Anal. Chem. 31:127–132].

Unless otherwise noted, all Orpinomyces enzyme assays were performed at 40° C. in 50 mM Bis-Tris Propane buffer, pH 6.0. One unit of enzyme activity is defined as the amount that released 1 μmol of product min-1, and specific activity is given in units per milligram of protein. Protein was determined by the method of Bradford [Bradford, M. (1976) Anal. Biochem. 72:248–254]. Feruloyl esterase activity was assayed by the method of Borneman et al. [(1990) supra] which involved measuring the release of ferulic acid from FAXX via HPLC using a mobile phase of 10 mM Na-formate pH 3 and 30% (vol/vol) methanol. FAXX was purified from wheat bran as previously described [Borneman et al. (1990) supra]. For assay using ethyl-p-coumarate (ethyl-pCA), the substrate (10 mM) was used with 30% methanol in the same mobile phase. Samples were run on a Hewlett Packard 1100 Series instrument equipped with an autosampler and diode array detector. Ferulic acid and p-coumaric acid were used as standards. The appropriately diluted protein sample (25 μl) was added to 400 μl of buffer containing 750 μM FAXX. Samples were incubated at 40° C. for 30 min. and the reaction was stopped by adding 25 μl of 20% formic acid. pH optimum assays were carried out in 100 mM citrate phosphate buffer in the range of 2.6–7.0, 100 mM phosphate in the range of pH 5.7–6.3, and 100 mM Tris in the range of pH 7.0–9.0. For temperature optimum determination, purified esterase were incubated for 30 minutes at the appropriate temperature within the range of 20° to 70° C.

All reactions to test the specificity of the Orpinomyces PC-2 enzyme were carried out in 50 mM citrate buffer pH 6.0. FAXX, FAX3, Et-FA and Et-pCA were assayed for 5 min. at 40° C. at a concentration of 10 mM. Enzyme solution (L) was added 400 μl of substrate solution. The reaction was stopped with 25 μl of 20% formate. For studies on wheat bran, crude recombinant FaeA (50 μl) equaling 0.7 units of activity against FAXX, XynA (50 μl) equaling 300 units of activity against birchwood xylan or both was added to a total reaction volume of 1 ml also containing 10 mg of destarched wheat bran. The reaction was carried out for 40 min at 40° C. and stopped by adding 50 μl of 20% formate.

Example 4

Enzyme Purification

One liter of recombinant E. coli expressing the C. thermocellum XynZ-derived FAE was grown in Luria broth containing 100 μg/ml ampicillin until $OD_{600}$=0.5 and then grown an additional 4–6 hours. Cells were harvested by centrifugation, resuspended at a concentration of 1 g per 3 ml in 50 mM Tris-HCl (pH 7.5) and lysed in a French pressure cell. Cell debris was removed by centrifugation at 100,000×g. The cell extract was heat treated for 30 min. at 70° C. Denatured protein was removed by centrifugation at 100,000×g. The supernatant was run on a MonoQ HR 10/10 ion exchange chromatography column (Pharmacia, Piscataway, N.J.) equilibrated with 50 mM sodium citrate buffer, pH 6.0. MonoQ (Pharmacia, Piscataway, N.J.) is a strong anion exchange resin, hydrophilic and in bead form. A linear gradient of 1M NaCl in the same buffer over 40 ml was used to elute the purified protein. Protein samples were stored at 4° C.

Alternatively, the 100,000×g supernatant after the heat treatment was concentrated to a volume of 2 ml with a Centricon 10 concentrator (Amicon, Millipore, Bedford, Mass.) and then applied to a TSK3000SW column (Tosohaas) which was run with 50 mM Tris pH 7.5 and 5% glycerol as solvent. The purified enzyme was stored at 4° C. in the elution buffer and was stable for at least a month with minimal loss.

A feruloyl esterase was purified from culture supernatant of Orpinomyces sp. strain PC-2 (Barichievicz and Calza medium [Barichievicz and Calza (1990) *Appl. Environ. Microbiol.* 56:43–48] with 0.2% Avicel as carbon source). The enzyme was obtained from a 60 liter culture of the fungus. The culture was grown under an atmosphere of $CO_2$ for 6 days. The fungal mycelia were removed by filtration through Miracloth (Calbiochem, San Diego, Calif.) The culture supernatant was concentrated 120 fold using a Pellicon system (Millipore, Bedford, Mass.) and a 10 kDa membrane. The concentrate was loaded onto a Q Sepharose (Pharmacia, Piscataway, N.J.) column equilibrated with 20 mM Tris·HCl pH 7.5, and proteins were eluted with a gradient of 1 M NaCl in the same buffer. The active fractions were detected by their ability to release ferulic acid from FAXX as measured by HPLC. The active fractions were combined and ammonium sulfate was added to a concentration of 1.7M. The solution was filtered and then loaded onto a Phenyl Sepharose High Performance Chromatography (Pharmacia) column equilibrated with 20 mM Tris·HCl pH 7.5 and 1.7 M ammonium sulfate. The protein was eluted by a negative gradient of buffer without ammonium sulfate. Active fractions were concentrated using a Centricon 10 unit (Amicon, Millipore, Bedford, Mass.) and subsequently applied to a TSK 3000SW column (Tosohaas, Montgomeryville, Pa.) which was equilibrated with 20 mM Tris·HCl pH 7.5 and 200 mM NaCl. Fractions with activity were combined and loaded directly onto an anion exchange (MonoQ HR 5/5, Pharmacia, Piscataway, N.J.) column equilibrated with 20 mM Tris·HCl pH 7.5. The purified enzyme was eluted using a gradient of 0.5 M NaCl. The purification is summarized in Table 7.

Example 5

Other Analytical Procedures

Enzyme purity was monitored using sodium dodecyl sulfate-polyacrylamide gel electrophoresis (SDS-PAGE) carried out according to the method of Laemmli [Laemmli (1970) *Nature (London)* 227:680–685]. Proteins were stained with Coomassie blue. The isoelectric point of the *C. thermocellum* XynZ-derived FAE protein was determined by running the protein on a precast IEF gel (Serva). Each gel was run at 12 W constant power for 45 min.

Protein concentrations in liquid samples were determined as described by Bradford, M. (1976) [supra].

The purity of the Orpinomyces FAE protein was verified by SDS-PAGE analysis and Coomassie blue staining. The enzyme had a molecular mass of approximately 50 kDa. Purified enzyme was blotted onto a polyvinylidene difloride (PVDF) membrane and stained according to the manufacturer's instructions. The band corresponding to the purified enzyme was cut out, and the excised band was digested with Protease Lys-C (Boehringer Mannheim, Indianapolis, Ind.). Peptides were separated by HPLC using a C8 reverse phase column. The intact protein and its peptides were subjected to N-terminal amino acid sequencing.

For internal sequencing, the enzyme was run on SDS-PAGE and then blotted onto a PVDF membrane which was stained according to the manufacturer's instructions. The band corresponding to the purified enzyme was cut out with a razor blade and digested with Protease Lys-C (Boehringer Mannheim). Peptides were separated on High Performance Liquid Chromatography with a C8 reverse phase column. The intact protein and its peptides were subjected to N-terminal amino acid sequencing using an Applied Biosystems model 477A gas-phase sequencer equipped with an automatic on-line phenylthiohydantoin analyzer.

Example 6

*C. thermocellum* Enzyme Stability Experiments

Purified enzyme at a concentration of 13 µg/ml was placed in a water bath at the appropriate temperature and incubated at intervals of one hour. Enzyme aliquots (25 µl) were removed and assays were performed in triplicate using FAX3 as a substrate as described above. FAE/CBD was tested at temperatures of 50°, 60°, and 70° C. while FAE was tested at 70°, 80° and 90° C.

Table 5 [taken from Fontes et al. (1995) supra] presents the nucleotide sequence and deduced amino acid sequence (amino acids 808–1061 of XylY) of *C. thermocellum* xylY, which is Xylanase Y. The starting points of the five domains are marked A to #, with arrows. The sequence is available under Accession Number X 83269, EMBL database.

Table 6 [taken from Grépinet et al. (1988) supra] presents the nucleotide and deduced amino acid sequences (amino acids 30–274 of XynZ) of the *C. thermocellum* xynZ and its gene product.

Table 9 presents the deduced amino acid sequence and cDNA coding sequence of the mature phenolic acid esterase of Orpinomyces PC-2.

FIG. 1 provides the amino acid sequence for a phenolic acid esterase (feruloyl esterase) which corresponds to a previously uncharacterized Ruminococcus xylanase. The sequence of the complete coding sequence of that xylanase is available under Accession No. S58235 (Gen Bank)(See Table 10). The coding sequence of the phenolic acid esterase polypeptide is nucleotide 2164–2895, exclusive of translation start and stop codons.

Catalytically active polypeptides were produced in recombinant *E. coli* after the PCR amplification and cloning as described in Example 2 herein above.

TABLE 1

Primer used in amplifying various regions of xynY and xynZ of *C. thermocellum*

| Name | Sequence[a] | Gene | Direction | Position[b] | SEQ ID NO: |
|---|---|---|---|---|---|
| XYF1Bam[a1] | TA<u>GGATCC</u>CCTGTAGCAGAAAATCCTTC | xynY | Forward | 795–800 | 1 |
| XYF1[c] | TA<u>CATATG</u>CCTGTAGCAGAAAATCCTTC | xynY | Forward | 795–800 | 2 |
| XYR1[c] | GA<u>GGAAGCTT</u>TTACATGGAAGAAATATGGAAG | xynY | Reverse | 1071–1077 | 3 |
| XZF1[d] | TA<u>CATATG</u>CTTGTCACAATAAGCAGTACA | xynZ | Forward | 20–26 | 4 |
| XZF1Bam | TA<u>GGATCC</u>CTTGTCACAATAAGCAGTACA | xynZ | Forward | 20–26 | 5 |
| XZR1[d] | GA<u>GGAAGCTT</u>TTAGTTGTTGGCAACGCAATA | xynZ | Reverse | 242–247 | 6 |
| XZR2[d] | GA<u>GGAAGCTT</u>ACTTCCACACATTAAAATC | xynZ | Reverse | 261–266 | 7 |
| XZR3[d] | GA<u>GGAAGCTT</u>AGTTTCCATCCCTCGTCAA | xynZ | Reverse | 281–286 | 8 |
| XZR4[d] | GA<u>GGAAGCTT</u>AGTCATAATCTTCCGCTTC | xynZ | Reverse | 302–307 | 9 |
| XZR5[d] | GA<u>GGAAGCTT</u>AAACGCCAAAAGTGAACCAGTC | xynZ | Reverse | 414–421 | 10 |

[a]Restriction sites NdeI and HindIII are underlined and double-underlined, respectively.
[a1]Restriction site BamH1 is underlined.
[b]Amino acid positions are according to xylanase sequences in the data banks.
[c]XYF1 or XYF1Bam and XYR1 are the forward and reverse primers used to amplify the feruloyl esterase domain from xylY(xynY) of *C. thermocellum* [see Fontes et al. (1995) supra].
[d]XZFl is the forward primer and XZR1–XZR5 are the reverse primers used in the amplification of the feruloyl esterase portion of the xynZ of *C. thermocellum*.

TABLE 2

Distribution of proteins and hydrolytic activities in *C. thermocellum* culture grown on Avicel

| Fraction | Protein mg/ml | Protein % | Feruloyl esterase U/ml | Feruloyl esterase % | Avicelase U/ml | Avicelase % | Xylanase U/ml | Xylanase % |
|---|---|---|---|---|---|---|---|---|
| Cell-associated | 0.09 | 39.1 | 0.005 | 2.1 | 0.001 | 2.4 | 0.49 | 5.3 |
| Cultural medium | 0.14 | 60.9 | 0.238 | 97.9 | 0.04 | 97.6 | 8.72 | 94.7 |
| After Avicel treatment | 0.11 | 47.8 | 0.002 | 0.8 | 0.004 | 9.7 | 1.56 | 16.9 |
| Avicel-bound | 0.03 | 13.2 | 0.24 | 97.1 | 0.033 | 80.5 | 6.75 | 73.3 |

TABLE 3A

Purification of the FAE/CBD polypeptide from *E. coli* cell free extract.

| Sample | Protein[a] (mg) | Total activity (U) | Specific Activity (U/mg) | Yield (%) | Purification Fold |
|---|---|---|---|---|---|
| Cell free extract | 2,597 | 3,253 | 1.25 | 100 | 1 |
| Heat treatment | 219.8 | 2,827 | 12.9 | 86.9 | 10.3 |

[a]The protein sample was obtained from 1.0 liter *E. coli* culture.

TABLE 3B

Purification of the XynZ FAE polypeptide from *E. coli* cell free extract.

| Sample | Protein[a] (mg) | Total activity (U) | Specific Activity (U/mg) | Yield (%) | Purification Fold |
|---|---|---|---|---|---|
| Cell free extract | 532.6 | 1520 | 2.9 | 100 | 1 |
| Heat treatment | 212.5 | 1629 | 7.7 | 107 | 2.7 |
| TSK 3000 SW | 30.9 | 823 | 26.6 | 54 | 9.7 |

[a]The protein sample was obtained from 1.0 liter *E. coli* culture.

TABLE 4

Substrate specificity of the feruloyl esterase in *C. thermocellum* XynZ.

| Substrate | Specific activity (U/mg) |
|---|---|
| FAXX | 12.5 |
| $FAX_3$ | 11.8 |
| $PAX_3$ | 1.4[a] |
| Ethyl-FA | 0.066 |
| Ethyl-pCA | 0.022 |
| CMC | 0 |
| PNP-arabinopyranoside | 0 |
| PNP-glucopyranoside | 0 |
| PNP-xylopyranoside | 0 |
| Wheat bran | 0.06 |
| Coastal Bermuda grass | 0.1 |

[a]Calculated value based on substrate concentration used in the assay

TABLE 5

Nucleotide and Deduced Amino Acid Sequences of *Clostridium thermocellum* Xylanase Y.

-200
TAAGAAACTTTAAAACACCCTTTATAAAAATACAAAGAATTACAGGCAATTATAGTGTAA

-100
TGTGGATTTTAACTAAAATGGAAGGAGGAATGTAATTGGTAATAGATATTATGATATAAT

TABLE 5-continued

Nucleotide and Deduced Amino Acid Sequences of *Clostridium thermocellum* Xylanase Y.

```
TTGTTTAGAGCATGCTTAAGTTTATTTAAATTTAATTTATAAATTAAATTAAAAATTAAA

+1
ATTTAAAAGGAGGTTCCTTATGAAAAACAAGAGAGTTTTGGCAAAAATAACGGCTCTTGTG
                  M  K  N  K  R  V  L  A  K  I  T  A  L  V

GTATTGCTGGGAGTGTTTTTTGTATTACCGTCAAACATAAGTCAGCTATATGCTGATTAT
 V  L  L  G  V  F  F  V  L  P  S  N  I  S  Q  L  Y  A  D  Y
                                 ↑
                                 A

5'pCF6
                                                        ↓
GAAGTGGTTCATGACACTTTTGAAGTTAACTTTGACGGATGGTGTAACTTGGGAGTCGAC
 E  V  V  K  D  T  F  E  V  N  F  D  G  W  C  N  L  G  V  D

200
ACATATTTAACGGCAGTTGAAAATGAAGGAAACAACGGTACAAGAGGTATGATCGTAATA
 T  Y  L  T  A  V  E  N  E  G  N  N  G  T  R  G  M  M  V  I

AATCGCTCCAGTGCGAGTGACGGTGCGTATTCGGAAAAAGGTTTCTATCTCGACGGTGGT
 N  R  S  S  A  S  D  G  A  Y  S  E  K  G  F  Y  L  D  G  G

300
GTAGAATACAAGTACAGTGTTTTTGTAAAACACAACGGGACCGGCACCGAAACTTTCAAA
 V  E  Y  K  Y  S  V  F  V  K  M  M  G  T  G  T  E  T  F  K

400
CTTTCTGTGTCCTATTTGGATTCGGAAACAGAAGAAGAAAATAAGGAAGTAATTGCAACA
 L  S  V  S  Y  L  D  S  E  T  E  E  E  N  K  E  V  I  A  T

5'pCF7
                                                        ↓
AAGGATGTTGTGGCCGGAGAATGGACTGAGATTTCGGCAAAATACAAAGCACCCAAAACT
 K  D  V  V  A  G  E  W  T  E  I  S  A  X  Y  K  A  P  X  T

500
GCAGTGAATATTACTTTGTCAATTACAACCGACAGCACTGTAGATTTCATTTTTGACGAT
 A  V  N  I  T  L  S  I  T  T  D  S  T  V  D  F  I  F  D  D

5'pCF2-5
   ↓
GTAACCATAACCCGTAAAGGAATGGCTGAGGCAAACACAGTATATGCAGCAAACGCTGTG
 V  T  I  T  R  K  G  M  A  E  A  N  T  V  Y  A  A  N  A  V

600
CTGAAAGATATGTATGCAAACTATTTCAGAGTTGGTTCGGTACTTAACTCCGGAACGGTA
 L  K  D  M  Y  A  N  Y  F  R  V  G  S  V  L  N  S  G  T  V
              ↑
              B

700
AACAATTCATCAATAAAGGCCTTGATTTTAAGAGAGTTTAACAGTATTACCTGTGAAAAT
 N  N  S  S  I  K  A  L  I  L  R  E  P  N  S  I  T  C  E  N

GAAATGAAGCCTGATGCCACACTGGTTCAATCAGGATCAACCAATACAAATATCAGGGTT
 E  M  K  P  D  A  T  L  V  Q  S  G  S  T  N  T  N  I  R  V

800
TCTCTTAATCGTGCAGCAAGTATTTTAAACTTCTGTGCACAAAATAATATAGCCGTCAGA
 S  L  N  R  A  A  S  I  L  N  F  C  A  Q  N  N  I  A  V  R

GGTCATACACTGGTTTGGCACAGCCAGACACCTCAATGGTTTTTCAAAGACAATTTCCAG
 G  H  T  L  V  W  H  S  Q  T  P  Q  W  F  F  K  D  N  F  Q

900
GACAACGGAAACTGGGTTTCCCAATCAGTTATGGACCAGCGTTTGGAAAGCTACATAAAA
 D  N  G  N  W  V  S  Q  S  V  M  D  Q  R  L  E  S  Y  I  K

1000
AATATGTTTGCTGAAATCCAAAGACAGTATCCGTCTTTGAATCTTTATGCCTATGACGTT
 N  M  F  A  E  I  Q  R  Q  Y  P  S  L  N  L  Y  A  Y  D  V
```

TABLE 5-continued

Nucleotide and Deduced Amino Acid Sequences of *Clostridium thermocellum* Xylanase Y.

```
GTAAATGAGGCAGTAAGTGATGATGCAAACAGGACCAGATATTATGGCGGGGCGAGGGAA
  V  N  E  A  V  S  D  D  A  N  R  T  R  Y  Y  G  G  A  R  E
2400
                              1100
CCTGGATACGGAAATCGTAGATCTCCATGGGTTCAGATCTACGGAGACAACAAATTTATT
  P  G  Y  G  N  R  S  P  W  V  Q  I  Y  G  D  N  K  F  I

5'pCF3
                                     ↓
GAGAAAGCATTTACATATGCAAGAAAATATGCTCCGGCAAATTGTAAGCTTTACTACAAC
  E  X  A  F  T  Y  A  R  K  Y  A  P  A  N  C  K  L  Y  Y  N

1200
GATTACAACGAATATTGGGATCATAAGAGACACTGTATTGCCTCAATTTGTGCAAACTTG
  D  Y  N  E  Y  W  D  H  K  R  D  C  I  A  S  I  C  A  N  L

1300
TACAACAAGGGCTTGCTTGACGGTGTGGGAATGCAGTCCCATATTAATGCGGATATGAAT
  Y  N  K  G  L  L  D  G  V  G  M  Q  S  K  I  N  A  D  M  N

GGATTCTCAGGTATACAAAATTATAAAGCAGCTTTGCACAAATATATAAATATCGGTTGT
  G  F  S  G  I  Q  N  Y  K  A  A  L  Q  K  Y  I  N  I  G  C

1400
GATGTCCAAATTACCGAGCTTGATATTAGTACAGAAAACGGCAAATTTAGCTTACAGCAG
  D  V  Q  I  T  E  L  D  I  S  T  E  N  G  K  F  S  L  Q  Q

CAGGCTGATAAATATAAAGCTGTTTTCCAGGCAGCTGTTGATATAAACAGAACCTCCAGC
  Q  A  D  K  Y  K  A  V  F  Q  A  A  V  D  I  N  R  T  S  S

1500
AAAGGAAAGGTTACGGCTGTCTGTGTATGGGGACCTAATGACGCCAATACTTGGCTCGGT
  K  G  K  V  T  A  V  C  V  W  G  P  N  D  A  N  T  W  L  G

1600
TCACAAAATGCACCTCTTTTGTTTAACCCAAACAATCAACCGAAACCGGCATACAATGCG
  S  Q  N  A  P  L  L  F  N  A  N  N  Q  P  K  P  A  Y  N  A

3'pCF2-3
                     ↓
GTTGCATCCATTATTCCTCAGTCCGAATGGGGCGACGGTAACAATCCGGCCGGCGGCGGA
  V  A  S  I  I  P  Q  S  E  W  G  D  G  N  N  P  A  G  G  G

1700
GGAGGAGGCAAACCGGAAGAGCCGGATGCAAACGGATATTATTATCATGACACTTTTGAA
  G  G  G  K  P  E  E  P  D  A  N  G  Y  Y  Y  N  D  T  F  E
                     ↑
                     C

GGAAGCGTAGGACAGTGGACAGCCAGAGGACCTGCGGAAGTTCTGCTTAGCGGAAGAACG
  G  S  V  G  Q  W  T  A  R  G  P  A  E  V  L  L  S  G  R  P

1800
GCTTACAAAGGTTCAGAATCACTCTTGGTAAGGAACCGTACGGCAGCATGCAACGGAGCA
  A  Y  X  G  S  E  S  L  L  V  R  N  R  T  A  A  W  N  G  A

1900
CAACGGGCGCTGAATCCCAGAACGTTTGTTCCCGGAAACACATATTGTTTCAGGGTAGTG
  Q  R  A  L  N  P  R  T  F  V  P  G  N  T  Y  C  F  S  V  V

GCATCGTTTATTGAAGGTGGGTCTTCCACAACATTCTGCATGAAGCTCCAATACGTAGAC
  A  S  F  I  E  G  A  S  S  T  T  F  C  M  K  L  Q  Y  V  D

2000
GGAAGCGGCACTCAACGGTATGATACCATAGATATGAAAACTGTGGGTCCAAATCAGTGG
  G  S  G  T  Q  R  Y  D  T  I  D  M  K  T  V  G  P  N  Q  W

GTTCACCTGTACAATCCGCAATACAGAATTCCTTCCGATGCAACAGATATGTATGTTTAT
  V  K  L  Y  N  P  Q  Y  R  I  P  S  D  A  T  D  M  Y  V  Y
```

TABLE 5-continued

Nucleotide and Deduced Amino Acid Sequences of *Clostridium thermocellum* Xylanase Y.

```
                         2100
GTGGAAACAGCGGATGACACCATTAACTTCTACATAGATGAGGCAATCGGAGCCGTTGCC
 V  E  T  A  D  D  T  I  N  P  Y  I  D  E  A  I  G  A  V  A

2200
GGAACTGTAATCGAAGGACCTGCTCCACAGCCTACACAGCCTCCGGTACTGCTTGGCGAT
 G  T  V  I  E  G  P  A  P  Q  P  T  Q  P  P  V  L  L  G  D
                                                           ↓
                                                           D

GTAAACGGTGATGGAACCATTAACTCAACTGACTTGACAATGTTAAAGAGAAGCGTGTTG
 V  N  G  D  G  T  I  N  S  T  D  L  T  M  L  K  R  S  V  L

2300
AGGGCAATCACCCTTACCGACGATGCAAAGGCTAGAGCAGACGTTGACAAGAATCGATCG
 R  A  I  T  L  T  D  D  A  K  A  R  A  D  V  D  K  N  G  S

3'pCF4
  ↓
ATAAACAGCACTGATGTTTTACTTCTTTCACGCTACCTTTTAAGAGTAATCGACAAATTT
 I  N  S  T  D  V  L  L  L  S  R  Y  L  L  R  V  I  D  K  F
                                                        ↑
                                                        E

2400
CCTGTAGCAGAAAATCCTTCTTCTTCTTTTAAATATGAGTCGGCCGTGCAATATCGGCCG
 P  V  A  E  N  P  S  S  S  F  K  Y  E  S  A  V  Q  Y  R  P

2500
GCTCCTGATTCTTATTTAAACCCTTGTCCGCAGGCGGGAAGAATTGTCAAGGAAACATAT
 A  P  D  S  Y  L  N  P  C  P  Q  A  G  R  I  V  K  E  T  Y

ACAGGAATAAACGGAACTAAGAGTCTTAATGTATATCTTCCATACGGTTATGATCCGAAC
 T  G  I  N  G  T  K  S  L  N  V  Y  L  P  Y  G  Y  D  P  N

2600
AAAAAATATAACATTTTCTACCTTATGCATGGCGGCGGTGAAAATGAGAATACGATTTTC
 K  K  Y  N  I  F  Y  L  M  H  G  G  G  E  N  E  N  T  I  F

AGCAACGATGTTAAATTGCAAAATATCCTTGACCACGCGATTATGAACGGTGAACTTGAG
 S  N  D  V  K  L  Q  N  I  L  D  N  A  I  M  N  G  E  L  E

2700
CCTTTGATTGTAGTAACACCCACTTTCAACGGCGGAAACTGCACGGCCCAAAACTTTTAT
 P  L  I  V  V  T  P  T  F  N  G  G  N  C  T  A  Q  N  F  Y

3'pCF6-8
         ↓                                        2800
CAGGAATTCAGGCAAAATGTCATTCCTTTTGTGGAAAGCAAGTACTCTACTTATGCAGAA
 Q  E  F  R  Q  N  V  I  P  F  V  E  S  K  Y  S  T  Y  A  E

TCAACAACCCCACAGGGAATAGCCGCTTCAAGAATGCACAGAGGTTTCGGCGGATTCTCA
 S  T  T  P  Q  G  I  A  A  S  R  M  H  R  G  F  G  G  F  S

2900
ATGGGAGGATTGACAACATGGTATGTAATGGTTAACTGCCTTGATTACGTTGCATATTTT
 M  G  G  L  T  T  W  Y  V  M  V  N  C  L  D  Y  V  A  Y  F

ATGCCTTTAAGCGGTGACTACTGGTATGGAAACAGTCCGCAGGATAAGGCTAATTCATT
 M  P  L  S  G  D  Y  N  G  N  S  P  Q  D  K  A  N  S  I

3000
GCTGAAGCAATTAACAGATCCGGACTTTCAAAGAGGGAGTATTTCGTATTTGCGGCCACC
 A  E  A  I  N  R  S  G  L  S  K  R  E  Y  F  V  P  A  A  T

3100
GGTTCCGACCATATTGCATATGCTAATATGAATCCTCAAATTGAAGCTATGAAGGCTTTG
 G  S  D  H  I  A  Y  A  N  M  M  P  Q  I  E  A  K  K  A  L

CCGCATTTTGATTATACTTCGGATTTTTCCAAACGTAATTTTTACTTTCTTGTAGCTCCG
 P  H  F  D  Y  T  S  D  F  S  K  G  N  P  Y  F  L  V  A  P
```

TABLE 5-continued

Nucleotide and Deduced Amino Acid Sequences of *Clostridium thermocellum* Xylanase Y.

```
                      ]                3200
GGCGCCACTCACTGGTGGGGATACGTAAGACATTATATTTATGATGCACTTCCATATTTC
 G  A  T  M  W  W  G] Y  V  R  H  Y  I  Y  D  A  L  P  Y  F

TTCCATGAATGAATGAGAAAGAAAAACATGATTGAGTTTCTAATCAATAAAAAAAGGAA
 P  H  E

3300
TTTTTTAGTGGTGTCCAGGTTATTGAA
```

Nucleotide sequence of xynY

The nucleotide sequence of xynY and the deduced primary structure of XYLY are shown. The locations of the first residues of domains A, B, C, D and E are indicated with the corresponding letters. The positions of the two primers used to amplify the region of xynY coding for the catalytic domain of the xylanase (pCF2/ 3) are indicated by overlining. The 5' and 3' nucleotides of truncated forms of xynY are indicated by a downward arrow and the plasmids that encode the derivatives of the xylanase gene. The nucleotide sequence has been submitted to the EMBL database under the accession number X83269.

TABLE 6

```
ATATATAAAT AAGGGTATTA ATTCTGCAAA AAGAAAAGTG TTTGCTACAT GAGGTCCATT AATTTTTATT TTATATCATA AATCAAAAAG GAGGAGAAAC
-100                                                                                                    SD    -1

MET SER ARG LYS LEU PHE SER VAL LEU LEU GLY LEU VAL MET LEU MET THR SER LEU VAL THR LEU VAL ILE SER SER THR SER ALA
ATG TCA ACA AAA CTT TTC AGT GTA CTT TTA GGC TTG GTT ATG CTT ATG ACA TCG CTT GTC ACA TTG GTT ATA AGC AGT ACA TCA GCG
 1                                                                         50

ALA SER PRO THR MET PRO PRO SER GLY TYR ASP GLN VAL ARG ASN GLY VAL GLN VAL VAL ASN ILE SER SER TYR
GCA TCC CCA ACC ATG CCG CCT TCG GGA TAT GAC CAG GTT ACG AAC GGC GTA CAG GTA GTC AAT ATT TCT TAT
              100

PHE SER THR ALA THR SER ARG ALA PRO ALA ARG VAL LEU PRO PRO GLY TYR SER LYS ASP LYS LYS TYR SER VAL LEU
TTC TCC ACG GCC ACC AGT CGA GCC CCG GCA AGA GTT TTG CCG CCG GGA TAT TCA AAG GAC AAA AAA TAC AGT GTT TTG
                              200

TYR LEU HIS GLY ILE GLY SER GLU ASN ASP TRP PHE GLU ASN THR PRO ASN VAL ILE ALA ASP ASN LEU ILE
TAT CTC CAC GGC ATA GGT AGT GAA AAT GAC TGG TTC GAA AAT ACT GTA ATT GCC GAC AAT CTG ATT
                                          100
                                              300

ALA GLU LYS ILE LYS PRO LEU ILE ILE THR PRO ILE ILE GLY ALA ALA GLY PRO ILE TYR GLU ASN
GCC GAG AAA ATC AAG CCC CTG ATA ATT ACA CCG ATA ATC GCC GCC GGT CCG ATA TAT GAA AAT
                                                  400                     500

PHE THR LYS ASP LEU LEU ASN SER LEU PRO TYR ILE GLU SER ASN TYR SER VAL TYR ASP ARG GLU HIS ARG ALA ILE
TTC ACA AAA GAT TTG CTC AAC AGT CTC ATT CCC TAT ATC GAA TCT AAC TAT TCA GTC TAC GAC CGC GAA CAT CGG GCG ATT

ALA GLY LEU SER MET GLY GLY GLN GLN SER PHE ASN ILE LEU THR ASP LYS PHE ALA TYR ILE GLY PRO ILE SER
GCA GGA CTT TCA ATG GGT GGA CAA TCG TTT AAT ATT GGA ACC GAT AAA TTT GCC TAT ATT GGC CCG ATT TCA

ALA ALA PRO ASN THR TYR PRO ASN GLU LEU PHE PRO ASP ALA ALA ARG LYS LEU LEU PHE ILU
GCG GCT CCA AAC ACT TAT CCA AAT GAG CTT TTT CCT GAC GCT GCA AGG GAG CTC TTT ATT
          200           600

ALA CYS GLY THR ASN ASP SER LEU ILE GLY PHE GLN ARG VAL HIS GLU TYR CYS VAL ALA ASN HIS VAL TYR
GCC TGC GGA ACC AAT GAC AGT CTG ATA GGT TTT CAG AGA GTA CAT GAA TAT TGC GTT GCC AAC CAT GTC TAT
                                                                                250

TRP LEU ILE GLN GLY GLY HIS ASP PHE ASN VAL TRP LYS PRO GLN MET ALA ASP ALA GLY
TGG CTT ATT CAG GGC GCA GGA CAC GAT TTT AAT GTG TGG AAG CCC CTT CAA ATG GCA GAT GAA GCC GGA
                                                    800

LEU THR ARG ASP GLY ASN THR PRO VAL PRO THR PRO SER PRO LYS PRO ALA ASN THR ARG ILE GLU ALA GLU ASP TYR ASP GLY
                                                    300 300
```

TABLE 6-continued

```
TTC ACG AGG GAT GGA AAC ACT CCG GTT ATT GAG TCA AGT CCA AAG CCG GCT AAC ACA CGT ATT GAA GCG GAA GAT TAT GAC GGT
ILE ASN SER SER ILE GLU SER SER PRO PRO GLU GLY VAL PRO LEU GLY TYR ILE THR SER GLY ASP TYR LEU
ATT AAT TCT TCA AGT ATT GAG AAC CTT CCA GTT CCA CTT GAA CGA AGA GGA ATA GGT TAT ATT ACC AGT GGT GAT TAT CTG
                                                                                                              1000
       pCT1208, pCT1211                                           350                              pCT1223
                                         ┌────
VAL TYR LYS SER ILE ASP PHE GLY ASN GLY ALA THR SER PHE LYS ALA│LYS VAL ALA ASN ALA ASN THR ASN SER ILE GLU LEU
GTA TAC AAG AGT ATA GAC TTT GGA AAC GGA GCA ACG TCG TTT AAG GCC│AAG GTT GCA AAT GCA AAT ACT ACT AAT ATT GAA CTT

ARG LEU ASN GLY PRO ASN GLY THR LEU ILE GLY THR LEU SER VAL LYS SER THR GLY ASP TRP ASN THR TYR GLU GLN THR
AGA TTA AAC GGT CCG AAT GGT ACT CTC ATA GGC ACA CTC TCG GTA AAA TCC ACA GGA GAT TGG AAT ACA TAT GAG CAA ACT
                                    1100
CYS SER ILE SER LYS VAL THR GLY ILE ASN ASP LEU TYR LEU VAL PHE LYS GLY PRO VAL ASN ILE ASP TRP PHE THR PHE GLY
TGC AGC ATT AGC AAA GTC ACC GGA ATA AAT GAT TTG TAC TTG GTA TTC AAA GGC CCT GTA AAC ATA GAC TGG TTC ACT TTT GGC
                                                                1200
                                  ┌─────
VAL GLU SER SER THR GLY LEU GLY│ASP LEU ASN GLY ASP GLY ASN SER SER ASP LEU GLN ALA LEU LYS ARG HIS
GTT GAA AGC AGT TCC ACA GGT CTG│GAT TTA AAT GGT GAC GGA AAT TCT AGT GAT CTT CAG GCG TTA AAG AGG CAT
                                     1300                                                         ┌────
                                                                                         pCT1216
                       ┌─────                  ─────┐                                  ┌────
LEU LEU GLY ILE SER│PRO LEU THR PRO ILE LEU ALA LEU LEU ARG ALA│ASP VAL ASN ARG SER GLY LYS VAL ASP SER THR ASP TYR
TTG CTC GGT ATA TCA│CCG CTT ACG GGA GAG CTT TTA AGA GCG│GAT GTA AAT AGG AGC GGC AAA GTG GAT TCT ACT GAC TAT
                                                                      1400                                    500
     pCT1218                                                                     pCT1215                          pCT1217
                   ┌─────                          ─────┐          ┌─────                                              ─────┐
SER VAL LEU LYS ARG TYR ILE LEU LEU ARG ILE ILE│THR GLU PHE PRO│GLY GLN GLY ASP VAL GLN THR PRO│ASN PRO SER VAL THR
TCA GTG CTG AAA AGA TAT ATA CTC CGC ATT ATT│ACA GAG TTC CCC│GGA CAA GGT GAT GTA CAG ACA CCC│AAT CCG TCT GTT ACT
                   pCT1219
                                                                                         pCT1221
PRO TER GLN THR PRO ILE PRO THR ILE SER GLY ASN ALA LEU ARG ASP TYR ALA GLU ALA ARG GLY ILE LYS ILE GLY THR CYS
CCG TAA CAA ACT CCC ATC CCT ACG ATT TCG GGA AAT GCT CTT AGG GAT TAT GCG GAG GCA AGG GGC ATA AAA ATC GGA ACA TGT
                                                                                                     550
                                  pCT1220
             ┌─────                                    ─────┐
SER VAL ASN TYR PRO PHE TYR THR│TYR ASN SER ASP PRO THR│TYR ASN SER ILE LEU GLN ARG GLU PHE SER MET VAL CYS GLU ASN
GTC AAC TAT CCG TTT TAC ACC│TAC AAT TCA GAT CCA ACC│TAT AAC AGC ATT TTG CAA AGA GAA TTT TCA ATG GTT GTA TGT GAA AAT
1600
```

TABLE 6-continued

```
GLU MET LYS PHE ASP ALA LEU GLN PRO ARG GLN ASN VAL PHE ASP PRE SER LYS GLY ASP GLN LEU LEU ALA PHE ALA GLU ARG
GAA ATG AAG TTT GAT GCT TTG CAG CCG AGA CAA AAC GTT TTT GAT TTT TCG AAA GGA GAC CAG TTG CTT GCA GAA AGA
                              1700                                600

ASN GLY MET GLN MET ARG GLY HIS THR LEU ILE TRP HIS ASN GLN ASN PRO SER TRP LEU THR ASN GLY ASN TRP ASN ARG ASP
AAC GGT ATG CAG ATG AGG GGA CAT ACG TTG ATT TGG CAC AAT CAA AAC CCG TCA TGG CTT ACA AAC GGT AAC TGG AAC CGG GAT
                                                      1800

SER LEU LEU ALA VAL MET LYS ASN HIS ILE THR THR VAL MET HIS TYR LYS GLY ILE VAL GLU TRP ASP VAL ALA ASN
TCG CTG CTT GCG GTA ATG AAA AAT CAC ATT ACC ACT GTT ATG CAT TAC AAA GGT ATT GTT GAG TGG GAT GCA AAC
                  650                                          1900

GLU CYS MET ASP ASP SER GLY ASN GLY LEU ARG SER SER ILE TRP ARG ASN VAL ILE GLY GLN ASP TYR LEU ASP TYR ALA PHE
GAA TGT ATG GAT GAT TCC GGC AAC GGC TTA AGA AGC ATA TGG AGA AAT GTA ATC GGT CAG GAC TAC CTT GAC TAT GCT TTC
                                                                          2000

ARG TYR ALA ARG GLU ALA ASP PRO ASP ALA LEU PHE TYR PHE ASN ASP TYR ASN ILE GLU ASN TRP LYS GLY PRO LYS SER ASN ALA
AGG TAT GCA AGA GAA GCA GAT CCC GAT GCA CTT TTC TAC TTT AAT GAT TAT AAT ATT GAA AAC TGG AAA GGT CCA AAG TCC AAT GCG
                                                                                                            700
                                                                                                2100

VAL PHE ASN MET ILE LYS SER MET ILE LYS GLU ARG GLY VAL PRO ILE ASP GLY VAL GLY PHE GLN CYS HIS PHE ILE ASN GLY MET
GTA TTT AAC ATG ATT AAA AGT ATG ATA AAA GAA AGA GGT GTG CCG ATT GAC GGA GTA GGA TTC CAA TGC CAC TTT ATC AAT GGA ATG

SER PRO GLU TYR LEU ALA SER ILE ASP GLN ASN ILE LYS TYR ALA GLU ILE GLY VAL ILE SER PHE THR GLU ILE ASP
AGC CCC GAG TAC CTT GCC AGT ATT GAT CAA AAT ATT AAG GAA ATA GGC GTT ATA GTA TCC TTT ACC GAA ATA GAT
                                                2200                                            750

ILE ARG ILE PRO GLN SER GLU ASN PRO ALA THR PHE ALA ASN GLN VAL GLN ALA ASN ASN TYR LYS GLU LEU MET LYS ILE CYS LEU
ATA CGC ATA CCT CAG TCG GAA AAC CCG GCA ACT TTC GCA AAT CAG GTA CAG GCA AAC AAT TAT AAG GAA CTT ATG AAA ATT TCT CTG
                                        2300

ALA ASN PRO ASN CYS ASN THR PHE VAL MET TRP GLY PHE THR ASP LYS TYR THR TRP ILE PRO GLY THR PHE PRO GLY TYR GLY
GCA AAC CCC AAT TGC AAT ACC TTT GTA ATG TGG GGA TTC ACA GAT AAA TAC ACA TGG ATT CCG GGA ACT TTC CCA GGA TAT GCC
                                                                800                 2400

ASN PRO LEU ILE TYR ASP SER ASN TYR ASN PRO LYS PRO ALA TYR ASN ALA ILE LYS GLU ALA LEU MET GLY TYR END
AAT CCA TTG ATT TAT GAC AGC AAT TAC AAT CCG AAA CCG GCA TAC AAT GCA ATA AAG GAA CCT CTT ATG GGC TAT TGA TAATTCC
                                                                                    2500

GAA AAGCTGAGCA GATAATGATG CCGTAAAGCC GGCTTCTGAA TTAAGAGCCG GCTTTACGGA CATATACTTT TTACGGCAGA ATACCTGTTA TTTCCATG
                                              →                                          2600
                                                                                          ←
```

Nucleotide sequence and deduced amino acid sequence of the xynZ gene of C. thermocellum. Numbering of both nucleotides amino acids starts with the beginning of the coding sequence. The putative Shine-Dalgarno sequence (SD) is underlined. Pro- and Thr- regions are in boldface type. The conserved, duplicated stretch is boxed (residues 430 to 453 and 464 to 487). A perfect 14-bp palindr which may serve as a transcription terminator is indicated by inverted arrows. Arrows in the coding sequence indicate the beginning of xynZ gene in the deleted clones.

TABLE 7

Purification of a Feruloyl Esterase from Orpinomyces PC-2 Culture Supernatant

| Step | Total Activity (U) | Total Protein (mg) | Specific Activity (Umg$^{-1}$) | Purification Fold |
|---|---|---|---|---|
| Culture Supernatant | 32.38 | 5,830 | 5.6E − 3 | 1 |
| Concentrate | 7.9 | 1460 | 5.42E − 3 | 0.96 |
| Q Sepharose | 2.58 | 181 | 1.43e − 2 | 2.55 |
| Phenyl Sepharose HP | 1.68 | 28.2 | 5.96E − 2 | 10.6 |
| TSK 3000 SW | 0.85 | 0.62 | 1.39 | 253 |
| Mono Q HR 5/5 | 0.26 | 0.24 | 1.087 | 198 |

TABLE 8

Substrate specificity of Orpinomyces FaeA

| Sample | μmole FA released min$^{-1}$ mg enzyme$^{-1}$ |
|---|---|
| FAXX | 2.05 |
| FAX$_3$ | 1.80 |
| Ethyl-ferulate | 0.07 |
| Ethyl-p-coumarate | 0.02 |
| Wheat Bran FaeA | 0.0002 |
| Wheat bran FaeA + XynA | 0.013 |

All reactions were carried out in 50 mM citrate buffer pH 6.0. FAXX, FAX$_3$, Et-FA and Et pCA were assayed for 5 min at 40° C. at a concentration of 10 mM. Enzyme solution (μL) was added 400 μL of substrate solution. The reaction was stopped with 25 μL of 20% formate.

For studies on wheat bran, crude recombinant FaeA (50 μL) equaling 0.7 units of activity against FAXX, XynA (50 μL) equaling 300 units of activity against birchwood xylan or both was added to a total reaction volume of 1 ml also containing 10 mg of destarched what bran. The reaction was carried out for 40 min at 40° C. and stopped by adding 50 μL of 20% formate.

TABLE 9

Nucleotide and Deduced Amino Acid Sequence for Feruloyl Esterase from Orpinomyces PC-2.

```
                GGTTGTTTCTTGTGAAACTACTTACGGTATTACTTTACGTGATACTA
 1              V   V   S   C   E T T Y G I T L R D T K

AGGAAAAATTCACTGTATTCAAAGACGGTTCCGCTGCTACTGATATTGTTGAATCAGAAG
 17  E  K F T V F K D =10 G S A A T D I-
     V  E S E D

ATGGTTCCGTTTCTTGGATTGCTACTGCTGCCGGTGGTGCTGGTGGTGGTGTTGCCTTCT
 37  G   S   V   S   W   I   A   T   A   A   G   G   A   G   G   G   V   A   F   Y

ATGTTAAGGCTAACAAGGAAGAAATTAACATTGCTAACTATGAATCTATCGATATTGAAA
 57  V   K   A   N   K   E   E   I   N   I   A   N   Y   E   S   I   D   I   E   M

TGGAATACACTCCAGTTGAAAACAAATGGAATGATGCTGCTAAGAACCCAAGTTTCTGTA
 77  E   Y   T   P   V   E   N   K   W   N   D   A   A   K   N   P   S   F   C   M

TGAGAATTCTTCCATGGGATTCCACTGGTATGTTCGGTGGTTACGAAGATCTTGAATACT
 97  R   I   L   P   W   D   S   T   G   M   F   G   G   Y   E   D   L   E   Y   F

TCGATACTCCAGCAAAATCTGGTAATTTCAAATACACTATTAAGATTCCTTCCTTCTTTG
117  D   T   P   A   K   S   G   N   F   K   Y   T   I   K   I   P   S   F   F   A

CTGATAAGATTTTATCTAGCTCTGATCTCGATTCTATCTTAAGTTTTGCTATCAAGTTCA
137  D   K   I   L   S   S   S   D   L   D   S   I   L   S   F   A   I   K   F   N

ACGATTATGAAAGAGGTAACACGGACGGTGACCAAATTAAGATTCAATTAAAGAATGTTA
157  D   Y   E   R   G   N   T   D   G   D   Q   I   K   I   Q   L   K   N   V   K

AATTCAACCCAAAGGAAAATGCTCCAGAAGATAAGGCTTTCGATGATGGTTTAAGGGATT
177  F   N   P   K   E   N   A   P   E   D   K   A   F   D   D   G   L   R   D   S

CTCAACGTGGTACTGTCGTTGAAATGAAATACTCATCTAGAGATTACACCGTCAAGGAAT
197  Q   R   G   T   V   V   E   M   K   Y   S   S   R   D   Y   T   V   K   E   S

CTGAAGCTGACAAATACGAAAAGCACGCTTGGGTTTACCTTCCAGCTGGTTATGAAGCTG
217  E   A   D   K   Y   E   K   H   A   W   V   Y   L   P   A   G   Y   E   A   D

ATAACAAGGATAAGAAATACCCATTAGTTGTTTTACTTCACGGTTATGGTCAAAATGAAA
237  N   K   D   K   K   Y   P   L   V   V   L   L   H   G   Y   G   Q   N   E   N

ACACTTGGGGTCTTTCCAACAAGGGTCGTGGTGGTAAGATCAAGGGTTACATGGACAGAG
257  T   W   G   L   S   N   K   G   R   G   G   K   I   K   G   Y   M   D   R   G

GTATGGCTAGTGGTAATGTTGAAAAGTTTGTTCTTGTTGCCGCTACTGGTGTTGCCAGTA
277  M   A   S   G   N   V   E   K   F   V   L   V   A   A   T   G   V   A   S   K
```

TABLE 9-continued

Nucleotide and Deduced Amino Acid Sequence for Feruloyl Esterase from Orpinomyces PC-2.

```
      AGAATTGGGGTCCAAACGGTTCTGGTGTTGATCTTGATGGTTTCAATGCTTTCGGTGGTG
297    N  W  G  P  N  G  S  G  V  D  L  D  G  F  N  A  F  G  G  E

AACTCAGAAACGATTTACTCCCATACATTAGAGCTCACTTCAATGTTAAGGTCGATCGTG
317    L  R  N  D  L  L  P  Y  I  R  A  H  F  N  V  K  V  D  R  D

ATCACACTGCTTTAGCTGGTCTTTCCATGGGTGGTGGTCAAACTATCAGTATTGGTATTG
337    H  T  A  L  A  G  L  S  M  G  G  G  Q  T  I  S  I  G  I  G

GTGAAACTCTTGATGAAATCAGTAACTACGGTTCTTTCTCTCCAGCTTTATTCCAAACTG
357    E  T  L  D  E  I  S  N  Y  G  S  F  S  P  A  L  F  Q  T  A

CTGAAGAATTCTTCGGTAAGGTTAAGGGTAACTTCAAGGAAGAACTTAGAATTCACAACC
377    E  E  F  F  G  K  V  K  G  N  F  K  E  E  L  R  I  H  N  L

TTTACATGACTTGTGGTGATGCTGATACTTTAGTTTACGATACTTACCCAAGTTACGTTG
397    Y  M  T  C  G  D  A  D  T  L  V  Y  D  T  Y  P  S  Y  V  E

AAGCTTTAAAGAATTGGGATGCTGTTGAATTCATGAAGGAATACACTTACCCAGGTGGTA
417    A  L  K  N  W  D  A  V  E  F  M  K  E  Y  T  Y  P  G  G  T

CTCACGATTTCCCAGTTTGGTACAGAGGTTTCAACGAATTCATTCAAATTGTTTTCAAAA
437    H  D  F  P  V  W  Y  R  G  F  N  E  F  I  Q  I  V  F  K  N

ATCAAAAAGTTAAGGAAGAACCAATTCATGCTGATCCAGTAGAAGACCCATCTGATGAAC
457    Q  K  V  K  E  E  P  I  H  A  D  P  V  E  D  P  S  D  E  P

CAGTTAGTGTTGATCCATCTGTTTCTGTCGAAGAACCAAATGACAGTGAATCTTCCTCTG
477    V  S  V  D  P  S  V  S  V  E  E  P  N  D  S  E  S  S  S  E

AAGATGAACCAGTGGTTAAAAAAACTATTAAGCACACCATTGCTAAGAAGAAGCCATCTA
497    D  E  P  V  V  K  K  T  I  K  H  T  I  A  K  K  K  P  S  K

AGACTAGAACTGTTACCAAGAAGGTCATTAAGAAGAAGAATAACTAAGAAAGTTTAGTTA
517    T  R  T  V  T  K  K  V  I  K  K  K  N  N  *

GTACAGTAGTGTAAAAAAAAAAAAAAAATCAAAAAGAAACTCGTGCCGAATTCGAT
```

TABLE 10

Nucleotide and Deduced Amino Acid Sequence for Ruminococcus sp. Xylanase (Xyn1)

GENBANK ACCESSION Z49970
Amino Acid Sequence

MKKTVKQFISSAVTALMVAASLPAVPSVNAADAQQRGNIGGFDY
EMWNQNGQGQVSMTPKAGSFTCSWSNIENFLARMGKNYDSQKKNYKAFGDITLSYDVE
YTPKGNSYMCVYGWTRNPLMEYYIVEGWGDWRPPGNDGENKGTVTLNGNTYDIRKTMR
YNQPSLDGTATFPQYWSVRQKSGSQNNTTNYMKGTISVSKHFDAWSKAGLDMSGTLYE
VSLNIEGYRSSGNANVKAISFDGSIPEPTSEPVTQPVVKAEPDANGYYFKEKFESGAG
DWSARGTGAKVTSSDGFNGSKGILVSGRGDNWHGAQLTLDSSAFTAGETYSFGALVKQ
DGESSTAMKLTLQYNDASGTANYDKVAEFTAPKGEWVDLSNTSFTIPSGASDLILYVE
APDSLTDFYIDNAFGGIKNTSPLEDVGSHTISTPGSETTTVTTASNKGIRGDINGDGV
INSFDLAPLRRGILKMMSGSGSTPENADVNGDGTVNVADLLLLQKFILGMEKSFPDPV
TTTTTKPITTTTEKIVTTTTSSSSSSSGKNLNADIRKDMPTSVPGGNEKSGGCKVEKK
TYNCKFTGGQKSCNVILPPNYSASKQYPVMYVLHGIGGNEGSMVSGMGVQELLAGLTA
NGKAEEMIIVLPSQYTSKNGNQGGGFGINQEVCAAYDNFLYDISDSLIPFIEANYPVK
TGRENRAITGFSMGGREAIYIGLMRPDLFAYVGGACPAPGITPGKDMFMEHPGCMQES
EMKFRDVGPEPNVFMITGGTNDGVVGTFPKQYSDILTRNGVDQRLPVYP"

| | |
|---|---|
| Coding Sequence | Nucleotides 529–2898 |
| signal peptide | encoded at nucleotides 529–627 |
| mature peptide | encoded at nucleotides 628–2895 |

```
  1 gatcttttc ataagtatgc ccccattatt aagttttta gatgcttgcc
    tataatttcc
 61 cttctggttt tgtgaacttc ttaacggtca gagttcacac tttctttata tat-
    tgtctat
121 attataatgt atattgtagt aataatatac caaaattttc ctttaagtaa
    caatatcttt
181 accctattta gcaatttta acgatatttt ataatttgat tattttaaa ctata-
    cagtg
```

TABLE 10-continued

Nucleotide and Deduced Amino Acid Sequence for
Ruminococcus sp. Xylanase (Xyn1)

```
 241 taaatactat tatttaaaaa gtccaccaaa aatgtaaaat acaatgatat
     cttaaacgta
 301 aaaacctgta caatgattgt tcatcttttt acattattgt tatatatcgt cttgg-
     tatag
 361 tcagcaattt ttagtcaaga tatacaaggt ccgcaaattt taacttgcaa ttaa-
     caggtc
 421 agatgtttta taatgatatc atagaaataa aaggagcact tggctcctta tggg-
     gattac
 481 tgaaatcata agtttgcttt ttttctaaaa acaaaggag tgattgaagt
     gaaaaaaaca
 541 gttaaacaat tcatcagcag tgccgttaca gcgttaatgg tggctgcaag cctgc-
     ctgcc
 601 gttccttccg tgaacgcagc cgacgcccag cagagaggca atatcggcgg tttc-
     gattac
 661 gaaatgtgga accagaacgg tcagggacag gtatcaatga cgcctaaggc
     aggctcttc
 721 acctgctcat ggagcaacat tgaaaacttc ctcgcacgta tgggcaagaa ctac-
     gacagc
 781 cagaaaaaga actacaaggc tttcggagac attaccctct cctacgacgt agag-
     tacacc
 841 cccaagggca actcttatat gtgcgtatac ggctggacga ggaaccctct catg-
     gaatac
 901 tacatcgtcg aaggctgggg cgactggcgt ccacccggaa atgacggcga aaa-
     caagggt
 961 acagttaccc tgaacggcaa cacctacgat atccgcaaaa caatgcgtta taat-
     cagcca
1021 tctctggacg gcacggctac attccctcag tactggagcg tacgtcagaa gagcg-
     gttca
1081 cagaataata ccaccaacta tatgaagggt actatcagcg tatccaagca
     ctttgacgca
1141 tggtcaaagg caggtctgga tatgagcggt actctctacg aggtatccct caa-
     catcgag
1201 ggctacagat caagcggaaa cgctaacgtt aaagctatct cattcgacgg cag-
     tataccc
1261 gagcccacaa gcgagcccgt aactcagccc gttgtcaagg cagagcctga
     cgcaaacggc
1321 tactacttca agaaaaatt cgagagcggc gcaggcgact ggtcagcccg cggaa-
     cagga
1381 gctaaggtaa caagctctga cggattcaac ggttcaaagg catactggt atcag-
     gacgc
1441 ggcgacaact ggcacggcgc acagctcaca ctcgactcaa gtgctttcac agcag-
     gcgaa
1501 acatacagct tcggcgcact tgtaaagcag gacggcgagt cctcaacagc tat-
     gaagctc
1561 actctccagt ataacgacgc aagcggcaca gccaattacg ataaggtggc agagt-
     tcaca
1621 gctccaaagg gtgaatgggt agacctttcc aatacatcgt tcactatccc gtcag-
     gcgct
1681 tcagacctca ttctctatgt tgaagctccc gacagcctta cggatttcta tatc-
     gacaac
1741 gctttcggcg gcatcaagaa cacatctcct cttgaagatg tcggaagcca tac-
     tatcagc
1801 actccgggca gcgagacaac aacagtcaca actgcatcaa ataagggtat cagag-
     gcgat
1861 atcaacggcg acggcgttat caactcattc gaccttgctc ctctcagaag
     aggcattctc
1921 aagatgatgt caggcagcgg ctcgactccc gaaaatgctg acgtaaacgg cgacg-
     gcact
1981 gtaaatgttg cagacctcct gcttctccag aagtttatac tcggtatgga gaagt-
     cattc
2041 cccgatcctg taacaactac cacgaccaag ccgataacaa caactaccga gaa-
     gatagtt
2101 accacaacta cttcttcatc ttcttcaagc tcaggcaaga acctcaatgc
     agatatccgc
2161 aaggatatgc ctacttcagt tcccggcgga aacgaaaaga gcggcggctg caag-
     gtcgag
2221 aagaagacat acaactgcaa gttcacaggc ggtcagaaga gctgcaacgt tatc-
     ctgcct
2281 cctaactaca gcgcaagcaa gcagtaccct gttatgtacg ttctccacgg tatcg-
     gcgga
2341 aacgagggaa gcatggtaag cggcatgggc gttcaggagc ttcttgcagg act-
     taccgca
2401 aacggcaagg cagaggaaat gataatcgtt ctcccgagcc agtacaccag caa-
     gaacggc
2461 aatcagggcg gcggcttcgg aatcaatcag gaagtatgcg cagcttacga taact-
     tcctc
2521 tatgatatct cagacagcct tatcccattc atcgaggcta actatcccgt taaga-
     caggc
2581 agagaaaacc gtgctatcac aggcttctca atgggcggac gtgaagctat
     ctatatcggt
2641 cttatgcgtc ccgacctctt cgcttacgtt ggcggagctt gccctgcacc cgg-
     tatcacc
```

TABLE 10-continued

Nucleotide and Deduced Amino Acid Sequence for
Ruminococcus sp. Xylanase (Xyn1)

2701 ccaggcaagg atatgttcat ggagcaccca ggctgtatgc aggagagcga aat-
     gaagttc
2761 agagacgttg gacctgagcc gaatgtattc atgataacag gcggcacaaa cgacg-
     gcgtc
2821 gtaggaacat tccccaagca gtacagcgat atccttacaa gaaacggcgt tgac-
     caacgt
2881 ttaccagtct atccctaacg gcggacacga cgcaggctct gtaaagcctc atctc-
     tacac
2941 attcatgaga tacgcattca aataatgata tagttgacat atgaaggaca
     gcgctttatg
3001 cgctgtcttt cttttgtgc aaaaagaaaa gccatttgag cttttgaagc
     tcaaatggct
3061 tatatttata atagtatagc ttattctgtt ctgagagcct ccaca

SEQUENCE LISTING

<160> NUMBER OF SEQ ID NOS: 24

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 1
taggatcccc tgtagcagaa aatccttc                                28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 2
tacatatgcc tgtagcagaa aatccttc                                28

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 3
gaggaagctt ttacatggaa gaaatatgga ag                           32

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:
      oligonucleotide used in polymerase chain reaction.

<400> SEQUENCE: 4
tacatatgct tgtcacaata agcagtaca                               29

<210> SEQ ID NO 5

```
<211> LENGTH: 29
<212> TYPE: DNA
<213> ORGANISM: Artificial Sequence
<220> FEATURE:
<223> OTHER INFORMATION: Description of Artificial  Sequence:
      oligonucleotide used in polymerase chain reaction.

<400> SEQUENCE: 5
taggatccct tgtcacaata agcagtaca                                    29

<210> SEQ ID NO 6
<211> LENGTH: 31
<212> TYPE: DNA
<213> ORGANISM: Artificial Sequence
<220> FEATURE:
<223> OTHER INFORMATION: Description of Artificial  Sequence:
      oligonucleotide used in polymerase chain reaction.

<400> SEQUENCE: 6
gaggaagctt ttagttgttg gcaacgcaat a                                 31

<210> SEQ ID NO 7
<211> LENGTH: 29
<212> TYPE: DNA
<213> ORGANISM: Artificial Sequence
<220> FEATURE:
<223> OTHER INFORMATION: Description of Artificial  Sequence:
      oligonucleotide used in polymerase chain reaction.

<400> SEQUENCE: 7
gaggaagctt acttccacac attaaaatc                                    29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial  Sequence:
      oligonucleotide used in polymerase chain reaction.

<400> SEQUENCE: 8
gaggaagctt agtttccatc cctcgtcaa                                    29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial  Sequence:
      oligonucleotide used in polymerase chain reaction.

<400> SEQUENCE: 9
gaggaagctt agtcataatc ttccgcttc                                    29

<210> SEQ ID NO 10
<211> LENGTH: 32
<212> TYPE: DNA
<213> ORGANISM: Artificial Sequence
<220> FEATURE:
<223> OTHER INFORMATION: Description of Artificial  Sequence:
      oligonucleotide used in polymerase chain reaction.

<400> SEQUENCE: 10
gaggaagctt aaacgccaaa agtgaaccag tc                                32

<210> SEQ ID NO 11
<211> LENGTH: 3507
```

```
<212> TYPE: DNA
<213> ORGANISM: Clostridium thermocellum
<220> FEATURE:
<221> NAME/KEY: CDS
<222> LOCATION: (200)..(3430)

<400> SEQUENCE: 11
taagaaactt taaaacaccc tttataaaaa tacaaagaat tacaggcaat t atagtgtaa      60 tgtggatttt aactaaaatg gaaggaggaa tgtaattcgt aatagatatt a tgatataat    120 ttgtttagag catgcttaag tttatttaaa tttaatttat aaattaaatt a aaaattaaa   180 atttaaaagg aggttgctt atg aaa aac aag aga gtt tt g gca aaa ata acg      232
                     Met Lys Asn Lys Arg Val Leu Ala Lys  Ile Thr
                      1               5                    10 gct ctt gtg gta ttg ctg gga gtg ttt ttt g ta tta ccg tca aac ata       280
Ala Leu Val Val Leu Leu Gly Val Phe Phe V al Leu Pro Ser Asn Ile
             15                  20                 25 agt cag cta tat gct gat tat gaa gtg gtt c at gac act ttt gaa gtt      328
Ser Gln Leu Tyr Ala Asp Tyr Glu Val Val H is Asp Thr Phe Glu Val
         30                  35                  40 aac ttt gac gga tgg tgt aac ttg gga gtc g ac aca tat tta acg gca      376
Asn Phe Asp Gly Trp Cys Asn Leu Gly Val A sp Thr Tyr Leu Thr Ala
     45                  50                  55 gtt gaa aat gaa gga aac aac ggt aca aga g gt atg atg gta ata aat      424
Val Glu Asn Glu Gly Asn Asn Gly Thr Arg G ly Met Met Val Ile Asn
 60                  65                  70                  75 cgc tcc agt gcg agt gac ggt gcg tat tcg g aa aaa ggt ttc tat ctc      472
Arg Ser Ser Ala Ser Asp Gly Ala Tyr Ser G lu Lys Gly Phe Tyr Leu
                 80                  85                  90 gac ggt ggt gta gaa tac aag tac agt gtt t tt gta aaa cac aac ggg      520
Asp Gly Gly Val Glu Tyr Lys Tyr Ser Val P he Val Lys His Asn Gly
             95                 100                 105 acc ggc acc gaa act ttc aaa ctt tct gtg t cc tat ttg gat tcg gaa      568
Thr Gly Thr Glu Thr Phe Lys Leu Ser Val S er Tyr Leu Asp Ser Glu
        110                 115                 120 aca gaa gaa gaa aat aag gaa gta att gca a ca aag gat gtt gtg gcc      616
Thr Glu Glu Glu Asn Lys Glu Val Ile Ala T hr Lys Asp Val Val Ala
    125                 130                 135 gga gaa tgg act gag att tcg gca aaa tac a aa gca ccc aaa act gca      664
Gly Glu Trp Thr Glu Ile Ser Ala Lys Tyr L ys Ala Pro Lys Thr Ala
140                 145                 150                 155 gtg aat att act ttg tca att aca acc gac a gc act gta gat ttc att      712
Val Asn Ile Thr Leu Ser Ile Thr Thr Asp S er Thr Val Asp Phe Ile
                160                 165                 170 ttt gac gat gta acc ata acc cgt aaa gga a tg gct gag gca aac aca      760
Phe Asp Asp Val Thr Ile Thr Arg Lys Gly M et Ala Glu Ala Asn Thr
            175                 180                 185 gta tat gca gca aac gct gtg ctg aaa gat a tg tat gca aac tat ttc      808
Val Tyr Ala Ala Asn Ala Val Leu Lys Asp M et Tyr Ala Asn Tyr Phe
        190                 195                 200 aga gtt ggt tcg gta ctt aac tcc gga acg g ta aac aat tca tca ata      856
Arg Val Gly Ser Val Leu Asn Ser Gly Thr V al Asn Asn Ser Ser Ile
    205                 210                 215 aag gcc ttg att tta aga gag ttt aac agt a tt acc tgt gaa aat gaa      904
Lys Ala Leu Ile Leu Arg Glu Phe Asn Ser I le Thr Cys Glu Asn Glu
220                 225                 230                 235 atg aag cct gat gcc aca ctg gtt caa tca g ga tca acc aat aca aat      952
Met Lys Pro Asp Ala Thr Leu Val Gln Ser G ly Ser Thr Asn Thr Asn
                240                 245                 250 atc agg gtt tct ctt aat cgt gca gca agt a tt tta aac ttc tgt gca     1000
```

```
                Ile Arg Val Ser Leu Asn Arg Ala Ala Ser I le Leu Asn Phe Cys Ala
                            255                 260                 265 caa aat aat ata gcc gtc aga ggt cat aca c tg gtt tgg cac agc cag          1048
Gln Asn Asn Ile Ala Val Arg Gly His Thr L eu Val Trp His Ser Gln
            270                 275                 280 aca cct caa tgg ttt ttc aaa gac aat ttc c ag gac aac gga aac tgg          1096
Thr Pro Gln Trp Phe Phe Lys Asp Asn Phe G ln Asp Asn Gly Asn Trp
            285                 290                 295 gtt tcc caa tca gtt atg gac cag cgt ttg g aa agc tac ata aaa aat          1144
Val Ser Gln Ser Val Met Asp Gln Arg Leu G lu Ser Tyr Ile Lys Asn
300                 305                 310                 315 atg ttt gct gaa atc caa aga cag tat ccg t ct ttg aat ctt tat gcc          1192
Met Phe Ala Glu Ile Gln Arg Gln Tyr Pro S er Leu Asn Leu Tyr Ala
                320                 325                 330 tat gac gtt gta aat gag gca gta agt gat g at gca aac agg acc aga          1240
Tyr Asp Val Val Asn Glu Ala Val Ser Asp A sp Ala Asn Arg Thr Arg
            335                 340                 345 tat tat ggc ggg gcg agg gaa cct gga tac g ga aat ggt aga tct cca          1288
Tyr Tyr Gly Gly Ala Arg Glu Pro Gly Tyr G ly Asn Gly Arg Ser Pro
            350                 355                 360 tgg gtt cag atc tac gga gac aac aaa ttt a tt gag aaa gca ttt aca          1336
Trp Val Gln Ile Tyr Gly Asp Asn Lys Phe I le Glu Lys Ala Phe Thr
            365                 370                 375 tat gca aga aaa tat gct ccg gca aat tgt a ag ctt tac tac aac gat          1384
Tyr Ala Arg Lys Tyr Ala Pro Ala Asn Cys L ys Leu Tyr Tyr Asn Asp
380                 385                 390                 395 tac aac gaa tat tgg gat cat aag aga gac t gt att gcc tca att tgt          1432
Tyr Asn Glu Tyr Trp Asp His Lys Arg Asp C ys Ile Ala Ser Ile Cys
                400                 405                 410 gca aac ttg tac aac aag ggc ttg ctt gac g gt gtg gga atg cag tcc          1480
Ala Asn Leu Tyr Asn Lys Gly Leu Leu Asp G ly Val Gly Met Gln Ser
            415                 420                 425 cat att aat gcg gat atg aat gga ttc tca g gt ata caa aat tat aaa          1528
His Ile Asn Ala Asp Met Asn Gly Phe Ser G ly Ile Gln Asn Tyr Lys
            430                 435                 440 gca gct ttg cag aaa tat ata aat atc ggt t gt gat gtc caa att acc          1576
Ala Ala Leu Gln Lys Tyr Ile Asn Ile Gly C ys Asp Val Gln Ile Thr
            445                 450                 455 gag ctt gat att agt aca gaa aac ggc aaa t tt agc tta cag cag cag          1624
Glu Leu Asp Ile Ser Thr Glu Asn Gly Lys P he Ser Leu Gln Gln Gln
460                 465                 470                 475 gct gat aaa tat aaa gct gtt ttc cag gca g ct gtt gat ata aac aga          1672
Ala Asp Lys Tyr Lys Ala Val Phe Gln Ala A la Val Asp Ile Asn Arg
                480                 485                 490 acc tcc agc aaa gga aag gtt acg gct gtc t gt gta tgg gga cct aat          1720
Thr Ser Ser Lys Gly Lys Val Thr Ala Val C ys Val Trp Gly Pro Asn
            495                 500                 505 gac gcc aat act tgg ctc ggt tca caa aat g ca cct ctt ttg ttt aac          1768
Asp Ala Asn Thr Trp Leu Gly Ser Gln Asn A la Pro Leu Leu Phe Asn
            510                 515                 520 gca aac aat caa ccg aaa ccg gca tac aat g cg gtt gca tcc att att          1816
Ala Asn Asn Gln Pro Lys Pro Ala Tyr Asn A la Val Ala Ser Ile Ile
525                 530                 535 cct cag tcc gaa tgg ggc gac ggt aac aat c cg gcc ggc ggc gga gga          1864
Pro Gln Ser Glu Trp Gly Asp Gly Asn Asn P ro Ala Gly Gly Gly Gly
540                 545                 550                 555 gga ggc aaa ccg gaa gag ccg gat gca aac g ga tat tat tat cat gac          1912
Gly Gly Lys Pro Glu Glu Pro Asp Ala Asn G ly Tyr Tyr Tyr His Asp
                560                 565                 570
```

-continued

| | |
|---|---|
| act ttt gaa gga agc gta gga cag tgg aca g cc aga gga cct gcg aa<br>Thr Phe Glu Gly Ser Val Gly Gln Trp Thr A la Arg Gly Pro Ala Glu<br>575 580 585 | 1960 |
| gtt ctg ctt agc gga aga acg gct tac aaa g gt tca gaa tca ctc ttg<br>Val Leu Leu Ser Gly Arg Thr Ala Tyr Lys G ly Ser Glu Ser Leu Leu<br>590 595 600 | 2008 |
| gta agg aac cgt acg gca gca tgg aac gga g ca caa cgg gcg ctg aat<br>Val Arg Asn Arg Thr Ala Ala Trp Asn Gly A la Gln Arg Ala Leu Asn<br>605 610 615 | 2056 |
| ccc aga acg ttt gtt ccc gga aac aca tat t gt ttc agc gta gtg gca<br>Pro Arg Thr Phe Val Pro Gly Asn Thr Tyr C ys Phe Ser Val Val Ala<br>620 625 630 635 | 2104 |
| tcg ttt att gaa ggt gcg tct tcc aca aca t tc tgc atg aag ctg caa<br>Ser Phe Ile Glu Gly Ala Ser Ser Thr Thr P he Cys Met Lys Leu Gln<br>640 645 650 | 2152 |
| tac gta gac gga agc ggc act caa cgg tat g at acc ata gat atg aaa<br>Tyr Val Asp Gly Ser Gly Thr Gln Arg Tyr A sp Thr Ile Asp Met Lys<br>655 660 665 | 2200 |
| act gtg ggt cca aat cag tgg gtt cac ctg t ac aat ccg caa tac aga<br>Thr Val Gly Pro Asn Gln Trp Val His Leu T yr Asn Pro Gln Tyr Arg<br>670 675 680 | 2248 |
| att cct tcc gat gca aca gat atg tat gtt t at gtg gaa aca gcg gat<br>Ile Pro Ser Asp Ala Thr Asp Met Tyr Val T yr Val Glu Thr Ala Asp<br>685 690 695 | 2296 |
| gac acc att aac ttc tac ata gat gag gca a tc gga gcg gtt gcc gga<br>Asp Thr Ile Asn Phe Tyr Ile Asp Glu Ala I le Gly Ala Val Ala Gly<br>700 705 710 715 | 2344 |
| act gta atc gaa gga cct gct cca cag cct a ca cag cct ccg gta ctg<br>Thr Val Ile Glu Gly Pro Ala Pro Gln Pro T hr Gln Pro Pro Val Leu<br>720 725 730 | 2392 |
| ctt ggc gat gta aac ggt gat gga acc att a ac tca act gac ttg aca<br>Leu Gly Asp Val Asn Gly Asp Gly Thr Ile A sn Ser Thr Asp Leu Thr<br>735 740 745 | 2440 |
| atg tta aag aga agc gtg ttg agg gca atc a cc ctt acc gac gat gca<br>Met Leu Lys Arg Ser Val Leu Arg Ala Ile T hr Leu Thr Asp Asp Ala<br>750 755 760 | 2488 |
| aag gct aga gca gac gtt gac aag aat gga t cg ata aac agc act gat<br>Lys Ala Arg Ala Asp Val Asp Lys Asn Gly S er Ile Asn Ser Thr Asp<br>765 770 775 | 2536 |
| gtt tta ctt ctt tca cgc tac ctt tta aga g ta atc gac aaa ttt cct<br>Val Leu Leu Leu Ser Arg Tyr Leu Leu Arg V al Ile Asp Lys Phe Pro<br>780 785 790 795 | 2584 |
| gta gca gaa aat cct tct tct tct ttt aaa t at gag tcg gcc gtg caa<br>Val Ala Glu Asn Pro Ser Ser Ser Phe Lys T yr Glu Ser Ala Val Gln<br>800 805 810 | 2632 |
| tat cgg ccg gct cct gat tct tat tta aac c ct tgt ccg cag gcg gga<br>Tyr Arg Pro Ala Pro Asp Ser Tyr Leu Asn P ro Cys Pro Gln Ala Gly<br>815 820 825 | 2680 |
| aga att gtc aag gaa aca tat aca gga ata a ac gga act aag agt ctt<br>Arg Ile Val Lys Glu Thr Tyr Thr Gly Ile A sn Gly Thr Lys Ser Leu<br>830 835 840 | 2728 |
| aat gta tat ctt cca tac ggt tat gat ccg a ac aaa aaa tat aac att<br>Asn Val Tyr Leu Pro Tyr Gly Tyr Asp Pro A sn Lys Lys Tyr Asn Ile<br>845 850 855 | 2776 |
| ttc tac ctt atg cat ggc ggt gaa aat g ag aat acg att ttc agc<br>Phe Tyr Leu Met His Gly Gly Glu Asn G lu Asn Thr Ile Phe Ser<br>860 865 870 875 | 2824 |
| aac gat gtt aaa ttg caa aat atc ctt gac c ac gcg att atg aac ggt<br>Asn Asp Val Lys Leu Gln Asn Ile Leu Asp H is Ala Ile Met Asn Gly<br>880 885 890 | 2872 |

-continued

```
gaa ctt gag cct ttg att gta gta aca ccc a ct ttc aac ggc gga aac      2920
Glu Leu Glu Pro Leu Ile Val Val Thr Pro T hr Phe Asn Gly Gly Asn
            895                 900                 905 tgc acg gcc caa aac ttt tat cag gaa ttc a gg caa aat gtc att cct      2968
Cys Thr Ala Gln Asn Phe Tyr Gln Glu Phe A rg Gln Asn Val Ile Pro
        910                 915                 920 ttt gtg gaa agc aag tac tct act tat gca g aa tca aca acc cca cag      3016
Phe Val Glu Ser Lys Tyr Ser Thr Tyr Ala G lu Ser Thr Thr Pro Gln
    925                 930                 935 gga ata gcc gct tca aga atg cac aga ggt t tc ggc gga ttc tca atg      3064
Gly Ile Ala Ala Ser Arg Met His Arg Gly P he Gly Gly Phe Ser Met
940                 945                 950                 955 gga gga ttg aca aca tgg tat gta atg gtt a ac tgc ctt gat tac gtt      3112
Gly Gly Leu Thr Thr Trp Tyr Val Met Val A sn Cys Leu Asp Tyr Val
                960                 965                 970 gca tat ttt atg cct tta agc ggt gac tac t gg tat gga aac agt ccg      3160
Ala Tyr Phe Met Pro Leu Ser Gly Asp Tyr T rp Tyr Gly Asn Ser Pro
            975                 980                 985 cag gat aag gct aat tca att gct gaa gca a tt aac aga tcc gga ctt      3208
Gln Asp Lys Ala Asn Ser Ile Ala Glu Ala I le Asn Arg Ser Gly Leu
        990                 995                1000 tca aag agg gag tat ttc gta ttt gcg gcc a cc ggt tcc gac cat att      3256
Ser Lys Arg Glu Tyr Phe Val Phe Ala Ala T hr Gly Ser Asp His Ile
    1005                1010                1015 gca tat gct aat atg aat cct caa att gaa g ct atg aag gct ttg ccg      3304
Ala Tyr Ala Asn Met Asn Pro Gln Ile Glu A la Met Lys Ala Leu Pro
1020                1025                1030                1035 cat ttt gat tat act tcg gat ttt tcc aaa g gt aat ttt tac ttt ctt      3352
His Phe Asp Tyr Thr Ser Asp Phe Ser Lys G ly Asn Phe Tyr Phe Leu
                1040                1045                1050 gta gct ccg ggc gcc act cac tgg tgg gga t ac gta aga cat tat att      3400
Val Ala Pro Gly Ala Thr His Trp Trp Gly T yr Val Arg His Tyr Ile
            1055                1060                1065 tat gat gca ctt cca tat ttc ttc cat gaa t gaatgagaa agaaaaacat        3450
Tyr Asp Ala Leu Pro Tyr Phe Phe His Glu
        1070                1075 gattgagttt gtaatcaata aaaaaggaa tttttagtg gtgtccaggt t attgaa         3507
```

<210> SEQ ID NO 12
<211> LENGTH: 1077
<212> TYPE: PRT
<213> ORGANISM: Clostridium thermocellum

<400> SEQUENCE: 12

```
Met Lys Asn Lys Arg Val Leu Ala Lys Ile T hr Ala Leu Val Val Leu
  1               5                  10                  15

Leu Gly Val Phe Phe Val Leu Pro Ser Asn I le Ser Gln Leu Tyr Ala
            20                  25                  30

Asp Tyr Glu Val Val His Asp Thr Phe Glu V al Asn Phe Asp Gly Trp
        35                  40                  45

Cys Asn Leu Gly Val Asp Thr Tyr Leu Thr A la Val Glu Asn Glu Gly
    50                  55                  60

Asn Asn Gly Thr Arg Gly Met Met Val Ile A sn Arg Ser Ser Ala Ser
65                  70                  75                  80

Asp Gly Ala Tyr Ser Glu Lys Gly Phe Tyr L eu Asp Gly Gly Val Glu
                85                  90                  95

Tyr Lys Tyr Ser Val Phe Val Lys His Asn G ly Thr Gly Thr Glu Thr
            100                 105                 110
```

```
Phe Lys Leu Ser Val Ser Tyr Leu Asp Ser Glu Thr Glu Glu Asn
        115                 120                 125
Lys Glu Val Ile Ala Thr Lys Asp Val Val Ala Gly Glu Trp Thr Glu
130                 135                 140
Ile Ser Ala Lys Tyr Lys Ala Pro Lys Thr Ala Val Asn Ile Thr Leu
145                 150                 155                 160
Ser Ile Thr Thr Asp Ser Thr Val Asp Phe Ile Phe Asp Asp Val Thr
                165                 170                 175
Ile Thr Arg Lys Gly Met Ala Glu Ala Asn Thr Val Tyr Ala Ala Asn
            180                 185                 190
Ala Val Leu Lys Asp Met Tyr Ala Asn Tyr Phe Arg Val Gly Ser Val
            195                 200                 205
Leu Asn Ser Gly Thr Val Asn Asn Ser Ser Ile Lys Ala Leu Ile Leu
210                 215                 220
Arg Glu Phe Asn Ser Ile Thr Cys Glu Asn Glu Met Lys Pro Asp Ala
225                 230                 235                 240
Thr Leu Val Gln Ser Gly Ser Thr Asn Thr Asn Ile Arg Val Ser Leu
                245                 250                 255
Asn Arg Ala Ala Ser Ile Leu Asn Phe Cys Ala Gln Asn Asn Ile Ala
            260                 265                 270
Val Arg Gly His Thr Leu Val Trp His Ser Gln Thr Pro Gln Trp Phe
            275                 280                 285
Phe Lys Asp Asn Phe Gln Asp Asn Gly Asn Trp Val Ser Gln Ser Val
290                 295                 300
Met Asp Gln Arg Leu Glu Ser Tyr Ile Lys Asn Met Phe Ala Glu Ile
305                 310                 315                 320
Gln Arg Gln Tyr Pro Ser Leu Asn Leu Tyr Ala Tyr Asp Val Val Asn
                325                 330                 335
Glu Ala Val Ser Asp Asp Ala Asn Arg Thr Arg Tyr Tyr Gly Gly Ala
            340                 345                 350
Arg Glu Pro Gly Tyr Gly Asn Gly Arg Ser Pro Trp Val Gln Ile Tyr
            355                 360                 365
Gly Asp Asn Lys Phe Ile Glu Lys Ala Phe Thr Tyr Ala Arg Lys Tyr
370                 375                 380
Ala Pro Ala Asn Cys Lys Leu Tyr Tyr Asn Asp Tyr Asn Glu Tyr Trp
385                 390                 395                 400
Asp His Lys Arg Asp Cys Ile Ala Ser Ile Cys Ala Asn Leu Tyr Asn
                405                 410                 415
Lys Gly Leu Leu Asp Gly Val Gly Met Gln Ser His Ile Asn Ala Asp
            420                 425                 430
Met Asn Gly Phe Ser Gly Ile Gln Asn Tyr Lys Ala Ala Leu Gln Lys
            435                 440                 445
Tyr Ile Asn Ile Gly Cys Asp Val Gln Ile Thr Glu Leu Asp Ile Ser
450                 455                 460
Thr Glu Asn Gly Lys Phe Ser Leu Gln Gln Gln Ala Asp Leu Tyr Lys
465                 470                 475                 480
Ala Val Phe Gln Ala Ala Val Asp Ile Asn Arg Thr Ser Ser Lys Gly
                485                 490                 495
Lys Val Thr Ala Val Cys Val Trp Gly Pro Asn Asp Ala Asn Thr Trp
            500                 505                 510
Leu Gly Ser Gln Asn Ala Pro Leu Leu Phe Asn Ala Asn Asn Gln Pro
            515                 520                 525
```

-continued

```
Lys Pro Ala Tyr Asn Ala Val Ala Ser Ile I le Pro Gln Ser Glu Trp
    530                 535                 540
Gly Asp Gly Asn Asn Pro Ala Gly Gly G ly Gly Gly Lys Pro Glu
545                 550                 555                 560
Glu Pro Asp Ala Asn Gly Tyr Tyr His A sp Thr Phe Glu Gly Ser
                565                 570                 575
Val Gly Gln Trp Thr Ala Arg Gly Pro Ala G lu Val Leu Leu Ser Gly
            580                 585                 590
Arg Thr Ala Tyr Lys Gly Ser Glu Ser Leu L eu Val Arg Asn Arg Thr
        595                 600                 605
Ala Ala Trp Asn Gly Ala Gln Arg Ala Leu A sn Pro Arg Thr Phe Val
    610                 615                 620
Pro Gly Asn Thr Tyr Cys Phe Ser Val Val A la Ser Phe Ile Glu Gly
625                 630                 635                 640
Ala Ser Ser Thr Thr Phe Cys Met Lys Leu G ln Tyr Val Asp Gly Ser
                645                 650                 655
Gly Thr Gln Arg Tyr Asp Thr Ile Asp Met L ys Thr Val Gly Pro Asn
            660                 665                 670
Gln Trp Val His Leu Tyr Asn Pro Gln Tyr A rg Ile Pro Ser Asp Ala
        675                 680                 685
Thr Asp Met Tyr Val Tyr Val Glu Thr Ala A sp Asp Thr Ile Asn Phe
    690                 695                 700
Tyr Ile Asp Glu Ala Ile Gly Ala Val Ala G ly Thr Val Ile Glu Gly
705                 710                 715                 720
Pro Ala Pro Gln Pro Thr Gln Pro Pro Val L eu Leu Gly Asp Val Asn
                725                 730                 735
Gly Asp Gly Thr Ile Asn Ser Thr Asp Leu T hr Met Leu Lys Arg Ser
            740                 745                 750
Val Leu Arg Ala Ile Thr Leu Thr Asp Ala L ys Ala Arg Ala Asp
        755                 760                 765
Val Asp Lys Asn Gly Ser Ile Asn Ser Thr A sp Val Leu Leu Leu Ser
    770                 775                 780
Arg Tyr Leu Leu Arg Val Ile Asp Lys Phe P ro Val Ala Glu Asn Pro
785                 790                 795                 800
Ser Ser Ser Phe Lys Tyr Glu Ser Ala Val G ln Tyr Arg Pro Ala Pro
                805                 810                 815
Asp Ser Tyr Leu Asn Pro Cys Pro Gln Ala G ly Arg Ile Val Lys Glu
            820                 825                 830
Thr Tyr Thr Gly Ile Asn Gly Thr Lys Ser L eu Asn Val Tyr Leu Pro
        835                 840                 845
Tyr Gly Tyr Asp Pro Asn Lys Lys Tyr Asn I le Phe Tyr Leu Met His
    850                 855                 860
Gly Gly Gly Glu Asn Glu Asn Thr Ile Phe S er Asn Asp Val Lys Leu
865                 870                 875                 880
Gln Asn Ile Leu Asp His Ala Ile Met Asn G ly Glu Leu Glu Pro Leu
                885                 890                 895
Ile Val Val Thr Pro Thr Phe Asn Gly Gly A sn Cys Thr Ala Gln Asn
            900                 905                 910
Phe Tyr Gln Glu Phe Arg Gln Asn Val Ile P ro Phe Val Glu Ser Lys
        915                 920                 925
Tyr Ser Thr Tyr Ala Glu Ser Thr Thr Pro G ln Gly Ile Ala Ala Ser
    930                 935                 940
Arg Met His Arg Gly Phe Gly Gly Phe Ser M et Gly Gly Leu Thr Thr
```

```
945              950              955              960

Trp Tyr Val Met Val Asn Cys Leu Asp Tyr V al Ala Tyr Phe Met Pro
                965              970              975

Leu Ser Gly Asp Tyr Trp Tyr Gly Asn Ser P ro Gln Asp Lys Ala Asn
            980              985              990

Ser Ile Ala Glu Ala Ile Asn Arg Ser Gly L eu Ser Lys Arg Glu Tyr
        995              1000             1005

Phe Val Phe Ala Ala Thr Gly Ser Asp His I le Ala Tyr Ala Asn Met
    1010             1015             1020

Asn Pro Gln Ile Glu Ala Met Lys Ala Leu P ro His Phe Asp Tyr Thr
025              1030             1035             1040

Ser Asp Phe Ser Lys Gly Asn Phe Tyr Phe L eu Val Ala Pro Gly Ala
            1045             1050             1055

Thr His Trp Trp Gly Tyr Val Arg His Tyr I le Tyr Asp Ala Leu Pro
            1060             1065             1070

Tyr Phe Phe His Glu
        1075

<210> SEQ ID NO 13
<211> LENGTH: 2722
<212> TYPE: DNA
<213> ORGANISM: Clostridium thermocellum
<220> FEATURE:
<221> NAME/KEY: CDS
<222> LOCATION: (101)..(2611)

<400> SEQUENCE: 13
atatataaat aagggtatta attctgcaaa aagaaaagtg tttgctacat g aggtccatt       60 aattttatt ttatatcata atcaaaaag gaggagaaac atg tca a ga aaa ctt          115
                                          Met Ser Arg Lys Leu
                                            1           5 ttc agt gta tta ctt gtt ggc ttg atg ctt a tg aca tcg ttg ctt gtc        163
Phe Ser Val Leu Leu Val Gly Leu Met Leu M et Thr Ser Leu Leu Val
            10              15              20 aca ata agc agt aca tca gcg gca tcc ttg c ca acc atg ccg cct tcg        211
Thr Ile Ser Ser Thr Ser Ala Ala Ser Leu P ro Thr Met Pro Pro Ser
        25              30              35 gga tat gac cag gta agg aac ggc gtt ccg a ga ggg cag gtc gta aat        259
Gly Tyr Asp Gln Val Arg Asn Gly Val Pro A rg Gly Gln Val Val Asn
    40              45              50 att tct tat ttc tcc acg gcc acc aac agt a cc agg ccg gca aga gtt        307
Ile Ser Tyr Phe Ser Thr Ala Thr Asn Ser T hr Arg Pro Ala Arg Val
55              60              65 tat ttg ccg ccg gga tat tca aag gac aaa a aa tac agt gtt ttg tat        355
Tyr Leu Pro Pro Gly Tyr Ser Lys Asp Lys L ys Tyr Ser Val Leu Tyr
70              75              80              85 ctc tta cac ggc ata ggc ggt agt gaa aac g ac tgg ttc gaa ggg gga        403
Leu Leu His Gly Ile Gly Gly Ser Glu Asn A sp Trp Phe Glu Gly Gly
            90              95              100 ggc aga gcc aat gtt att gcc gac aat ctg a tt gcc gag gga aaa atc       451
Gly Arg Ala Asn Val Ile Ala Asp Asn Leu I le Ala Glu Gly Lys Ile
        105             110             115 aag ccc ctg ata att gta aca ccg aat act a ac gcc gcc ggt ccg gga       499
Lys Pro Leu Ile Ile Val Thr Pro Asn Thr A sn Ala Ala Gly Pro Gly
    120             125             130 ata gcg gac ggt tat gaa aat ttc aca aaa g at ttg ctc aac agt ctt       547
Ile Ala Asp Gly Tyr Glu Asn Phe Thr Lys A sp Leu Leu Asn Ser Leu
    135             140             145
```

-continued

| | |
|---|---|
| att ccc tat atc gaa tct aac tat tca gtc t ac acc gac cgc gaa cat<br>Ile Pro Tyr Ile Glu Ser Asn Tyr Ser Val T yr Thr Asp Arg Glu His<br>150                   155                   160                   165 | 595 |
| cgg gcg att gca gga ctt tca atg ggt gga g ga caa tcg ttt aat att<br>Arg Ala Ile Ala Gly Leu Ser Met Gly Gly G ly Gln Ser Phe Asn Ile<br>              170                   175                   180 | 643 |
| gga ttg acc aat ctc gat aaa ttt gcc tat a tt ggc ccg att tca gcg<br>Gly Leu Thr Asn Leu Asp Lys Phe Ala Tyr I le Gly Pro Ile Ser Ala<br>         185                   190                   195 | 691 |
| gct cca aac act tat cca aat gag agg ctt t tt cct gac gga gga aaa<br>Ala Pro Asn Thr Tyr Pro Asn Glu Arg Leu P he Pro Asp Gly Gly Lys<br>              200                   205                   210 | 739 |
| gct gca agg gag aaa ttg aaa ctg ctc ttt a tt gcc tgc gga acc aat<br>Ala Ala Arg Glu Lys Leu Lys Leu Leu Phe I le Ala Cys Gly Thr Asn<br>215                   220                   225 | 787 |
| gac agt ctg ata ggt ttt gga cag aga gta c at gaa tat tgc gtt gcc<br>Asp Ser Leu Ile Gly Phe Gly Gln Arg Val H is Glu Tyr Cys Val Ala<br>230                   235                   240                   245 | 835 |
| aac aac att aac cat gtc tat tgg ctt att c ag ggc gga gga cac gat<br>Asn Asn Ile Asn His Val Tyr Trp Leu Ile G ln Gly Gly Gly His Asp<br>         250                   255                   260 | 883 |
| ttt aat gtg tgg aag ccc gga ttg tgg aat t tc ctt caa atg gca gat<br>Phe Asn Val Trp Lys Pro Gly Leu Trp Asn P he Leu Gln Met Ala Asp<br>              265                   270                   275 | 931 |
| gaa gcc gga ttg acg agg gat gga aac act c cg gtt ccg aca ccc agt<br>Glu Ala Gly Leu Thr Arg Asp Gly Asn Thr P ro Val Pro Thr Pro Ser<br>              280                   285                   290 | 979 |
| cca aag ccg gct aac aca cgt att gaa gcg g aa gat tat gac ggt att<br>Pro Lys Pro Ala Asn Thr Arg Ile Glu Ala G lu Asp Tyr Asp Gly Ile<br>295                   300                   305 | 1027 |
| aat tct tca agt att gag ata ata ggt gtt c ca cct gaa gga ggc aga<br>Asn Ser Ser Ser Ile Glu Ile Ile Gly Val P ro Pro Glu Gly Gly Arg<br>310                   315                   320                   325 | 1075 |
| gga ata ggt tat att acc agt ggt gat tat c tg gta tac aag agt ata<br>Gly Ile Gly Tyr Ile Thr Ser Gly Asp Tyr L eu Val Tyr Lys Ser Ile<br>              330                   335                   340 | 1123 |
| gac ttt gga aac gga gca acg tcg ttt aag g cc aag gtt gca aat gca<br>Asp Phe Gly Asn Gly Ala Thr Ser Phe Lys A la Lys Val Ala Asn Ala<br>         345                   350                   355 | 1171 |
| aat act tcc aat att gaa ctt aga tta aac g gt ccg aat ggt act ctc<br>Asn Thr Ser Asn Ile Glu Leu Arg Leu Asn G ly Pro Asn Gly Thr Leu<br>              360                   365                   370 | 1219 |
| ata ggc aca ctc tcg gta aaa tcc aca gga g at tgg aat aca tat gag<br>Ile Gly Thr Leu Ser Val Lys Ser Thr Gly A sp Trp Asn Thr Tyr Glu<br>375                   380                   385 | 1267 |
| gag caa act tgc agc att agc aaa gtc acc g ga ata aat gat ttg tac<br>Glu Gln Thr Cys Ser Ile Ser Lys Val Thr G ly Ile Asn Asp Leu Tyr<br>390                   395                   400                   405 | 1315 |
| ttg gta ttc aaa ggc cct gta aac ata gac t gg ttc act ttt ggc gtt<br>Leu Val Phe Lys Gly Pro Val Asn Ile Asp T rp Phe Thr Phe Gly Val<br>              410                   415                   420 | 1363 |
| gaa agc agt tcc aca ggt ctg ggg gat tta a at ggt gac gga aat att<br>Glu Ser Ser Ser Thr Gly Leu Gly Asp Leu A sn Gly Asp Gly Asn Ile<br>         425                   430                   435 | 1411 |
| aac tcg tcg gac ctt cag gcg tta aag agg c at ttg ctc ggt ata tca<br>Asn Ser Ser Asp Leu Gln Ala Leu Lys Arg H is Leu Leu Gly Ile Ser<br>              440                   445                   450 | 1459 |
| ccg ctt acg gga gag gct ctt tta aga gcg g at gta aat agg agc ggc<br>Pro Leu Thr Gly Glu Ala Leu Leu Arg Ala A sp Val Asn Arg Ser Gly<br>455                   460                   465 | 1507 |

-continued

| | |
|---|---|
| aaa gtg gat tct act gac tat tca gtg ctg a aa aga tat ata ctc cgc<br>Lys Val Asp Ser Thr Asp Tyr Ser Val Leu Lys Arg Tyr Ile Leu Arg<br>470                      475                  480                  485 | 1555 |
| att att aca gag ttc ccc gga caa ggt gat g ta cag aca ccc aat ccg<br>Ile Ile Thr Glu Phe Pro Gly Gln Gly Asp Val Gln Thr Pro Asn Pro<br>490                      495                  500 | 1603 |
| tct gtt act ccg aca caa act cct atc ccc a cg att tcg gga aat gct<br>Ser Val Thr Pro Thr Gln Thr Pro Ile Pro Thr Ile Ser Gly Asn Ala<br>505                      510                  515 | 1651 |
| ctt agg gat tat gcg gag gca agg gga ata a aa atc gga aca tgt gtc<br>Leu Arg Asp Tyr Ala Glu Ala Arg Gly Ile Lys Ile Gly Thr Cys Val<br>520                      525                  530 | 1699 |
| aac tat ccg ttt tac aac aat tca gat cca a cc tac aac agc att ttg<br>Asn Tyr Pro Phe Tyr Asn Asn Ser Asp Pro Thr Tyr Asn Ser Ile Leu<br>535                      540                  545 | 1747 |
| caa aga gaa ttt tca atg gtt gta tgt gaa a at gaa atg aag ttt gat<br>Gln Arg Glu Phe Ser Met Val Val Cys Glu Asn Glu Met Lys Phe Asp<br>550                      555                  560                  565 | 1795 |
| gct ttg cag ccg aga caa aac gtt ttt gat t tt tcg aaa gga gac cag<br>Ala Leu Gln Pro Arg Gln Asn Val Phe Asp Phe Ser Lys Gly Asp Gln<br>570                      575                  580 | 1843 |
| ttg ctt gct ttt gca gaa aga aac ggt atg c ag atg agg gga cat acg<br>Leu Leu Ala Phe Ala Glu Arg Asn Gly Met Gln Met Arg Gly His Thr<br>585                      590                  595 | 1891 |
| ttg att tgg cac aat caa aac ccg tca tgg c tt aca aac ggt aac tgg<br>Leu Ile Trp His Asn Gln Asn Pro Ser Trp Leu Thr Asn Gly Asn Trp<br>600                      605                  610 | 1939 |
| aac cgg gat tcg ctg ctt gcg gta atg aaa a at cac att acc act gtt<br>Asn Arg Asp Ser Leu Leu Ala Val Met Lys Asn His Ile Thr Thr Val<br>615                      620                  625 | 1987 |
| atg acc cat tac aaa ggt aaa att gtt gag t gg gat gtg gca aac gaa<br>Met Thr His Tyr Lys Gly Lys Ile Val Glu Trp Asp Val Ala Asn Glu<br>630                      635                  640                  645 | 2035 |
| tgt atg gat gat tcc ggc aac ggc tta aga a gc agc ata tgg aga aat<br>Cys Met Asp Asp Ser Gly Asn Gly Leu Arg Ser Ser Ile Trp Arg Asn<br>650                      655                  660 | 2083 |
| gta atc ggt cag gac tac ctt gac tat gct t tc agg tat gca aga gaa<br>Val Ile Gly Gln Asp Tyr Leu Asp Tyr Ala Phe Arg Tyr Ala Arg Glu<br>665                      670                  675 | 2131 |
| gca gat ccc gat gca ctt ctt ttc tac aat g at tat aat att gaa gac<br>Ala Asp Pro Asp Ala Leu Leu Phe Tyr Asn Asp Tyr Asn Ile Glu Asp<br>680                      685                  690 | 2179 |
| ttg ggt cca aag tcc aat gcg gta ttt aac a tg att aaa agt atg aag<br>Leu Gly Pro Lys Ser Asn Ala Val Phe Asn Met Ile Lys Ser Met Lys<br>695                      700                  705 | 2227 |
| gaa aga ggt gtg ccg att gac gga gta gga t tc caa tgc cac ttt atc<br>Glu Arg Gly Val Pro Ile Asp Gly Val Gly Phe Gln Cys His Phe Ile<br>710                      715                  720                  725 | 2275 |
| aat gga atg agc ccc gag tac ctt gcc agc a tt gat caa aat att aag<br>Asn Gly Met Ser Pro Glu Tyr Leu Ala Ser Ile Asp Gln Asn Ile Lys<br>730                      735                  740 | 2323 |
| aga tat gcg gaa ata ggc gtt ata gta tcc t tt acc gaa ata gat ata<br>Arg Tyr Ala Glu Ile Gly Val Ile Val Ser Phe Thr Glu Ile Asp Ile<br>745                      750                  755 | 2371 |
| cgc ata cct cag tcg gaa aac ccg gca act g ca ttc cag gta cag gca<br>Arg Ile Pro Gln Ser Glu Asn Pro Ala Thr Ala Phe Gln Val Gln Ala<br>760                      765                  770 | 2419 |
| aac aac tat aag gaa ctt atg aaa att tgt c tg gca aac ccc aat tgc<br>Asn Asn Tyr Lys Glu Leu Met Lys Ile Cys Leu Ala Asn Pro Asn Cys | 2467 |

```
                 775              780              785
aat acc ttt gta atg tgg gga ttc aca gat a aa tac aca tgg att ccg       2515
Asn Thr Phe Val Met Trp Gly Phe Thr Asp L ys Tyr Thr Trp Ile Pro
790             795             800              805 gga act ttc cca gga tat ggc aat cca ttg a tt tat gac agc aat tac       2563
Gly Thr Phe Pro Gly Tyr Gly Asn Pro Leu I le Tyr Asp Ser Asn Tyr
                810             815             820 aat ccg aaa ccg gca tac aat gca ata aag g aa gct ctt atg ggc tat       2611
Asn Pro Lys Pro Ala Tyr Asn Ala Ile Lys G lu Ala Leu Met Gly Tyr
                825             830             835 tgataattcc gaaaagctga gcagataatg atgccgtaaa gccggcttct g aattaagag     2671 ccggctttac ggagatatac tttttacggc agaatacctg ttatttccat g              2722

<210> SEQ ID NO 14
<211> LENGTH: 837
<212> TYPE: PRT
<213> ORGANISM: Clostridium thermocellum

<400> SEQUENCE: 14

Met Ser Arg Lys Leu Phe Ser Val Leu Leu V al Gly Leu Met Leu Met
1               5                  10                  15

Thr Ser Leu Leu Val Thr Ile Ser Ser Thr S er Ala Ala Ser Leu Pro
            20                  25                  30

Thr Met Pro Pro Ser Gly Tyr Asp Gln Val A rg Asn Gly Val Pro Arg
        35                  40                  45

Gly Gln Val Val Asn Ile Ser Tyr Phe Ser T hr Ala Thr Asn Ser Thr
    50                  55                  60

Arg Pro Ala Arg Val Tyr Leu Pro Pro Gly T yr Ser Lys Asp Lys Lys
65              70                  75                  80

Tyr Ser Val Leu Tyr Leu Leu His Gly Ile G ly Gly Ser Glu Asn Asp
                85                  90                  95

Trp Phe Glu Gly Gly Gly Arg Ala Asn Val I le Ala Asp Asn Leu Ile
            100                 105                 110

Ala Glu Gly Lys Ile Lys Pro Leu Ile Ile V al Thr Pro Asn Thr Asn
        115                 120                 125

Ala Ala Gly Pro Gly Ile Ala Asp Gly Tyr G lu Asn Phe Thr Lys Asp
    130                 135                 140

Leu Leu Asn Ser Leu Ile Pro Tyr Ile Glu S er Asn Tyr Ser Val Tyr
145                 150                 155                 160

Thr Asp Arg Glu His Arg Ala Ile Ala Gly L eu Ser Met Gly Gly Gly
                165                 170                 175

Gln Ser Phe Asn Ile Gly Leu Thr Asn Leu A sp Lys Phe Ala Tyr Ile
            180                 185                 190

Gly Pro Ile Ser Ala Ala Pro Asn Thr Tyr P ro Asn Glu Arg Leu Phe
        195                 200                 205

Pro Asp Gly Gly Lys Ala Ala Arg Glu Lys L eu Lys Leu Leu Phe Ile
    210                 215                 220

Ala Cys Gly Thr Asn Asp Ser Leu Ile Gly P he Gly Gln Arg Val His
225                 230                 235                 240

Glu Tyr Cys Val Ala Asn Asn Ile Asn His V al Tyr Trp Leu Ile Gln
                245                 250                 255

Gly Gly Gly His Asp Phe Asn Val Trp Lys P ro Gly Leu Trp Asn Phe
            260                 265                 270

Leu Gln Met Ala Asp Glu Ala Gly Leu Thr A rg Asp Gly Asn Thr Pro
        275                 280                 285
```

```
Val Pro Thr Pro Ser Pro Lys Pro Ala Asn Thr Arg Ile Glu Ala Glu
    290                 295                 300

Asp Tyr Asp Gly Ile Asn Ser Ser Ile Glu Ile Ile Gly Val Pro
305                 310                 315                 320

Pro Glu Gly Gly Arg Gly Ile Gly Tyr Ile Thr Ser Gly Asp Tyr Leu
                325                 330                 335

Val Tyr Lys Ser Ile Asp Phe Gly Asn Gly Ala Thr Ser Phe Lys Ala
            340                 345                 350

Lys Val Ala Asn Ala Asn Thr Ser Asn Ile Glu Leu Arg Leu Asn Gly
        355                 360                 365

Pro Asn Gly Thr Leu Ile Gly Thr Leu Ser Val Lys Ser Thr Gly Asp
    370                 375                 380

Trp Asn Thr Tyr Glu Glu Gln Thr Cys Ser Ile Ser Lys Val Thr Gly
385                 390                 395                 400

Ile Asn Asp Leu Tyr Leu Val Phe Lys Gly Pro Val Asn Ile Asp Trp
                405                 410                 415

Phe Thr Phe Gly Val Glu Ser Ser Thr Gly Leu Gly Asp Leu Asn
            420                 425                 430

Gly Asp Gly Asn Ile Asn Ser Ser Asp Leu Gln Ala Leu Lys Arg His
        435                 440                 445

Leu Leu Gly Ile Ser Pro Leu Thr Gly Glu Ala Leu Leu Arg Ala Asp
    450                 455                 460

Val Asn Arg Ser Gly Lys Val Asp Ser Thr Asp Tyr Ser Val Leu Lys
465                 470                 475                 480

Arg Tyr Ile Leu Arg Ile Ile Thr Glu Phe Pro Gly Gln Gly Asp Val
                485                 490                 495

Gln Thr Pro Asn Pro Ser Val Thr Pro Thr Gln Thr Pro Ile Pro Thr
            500                 505                 510

Ile Ser Gly Asn Ala Leu Arg Asp Tyr Ala Glu Ala Arg Gly Ile Lys
        515                 520                 525

Ile Gly Thr Cys Val Asn Tyr Pro Phe Tyr Asn Asn Ser Asp Pro Thr
    530                 535                 540

Tyr Asn Ser Ile Leu Gln Arg Glu Phe Ser Met Val Val Cys Glu Asn
545                 550                 555                 560

Glu Met Lys Phe Asp Ala Leu Gln Pro Arg Gln Asn Val Phe Asp Phe
                565                 570                 575

Ser Lys Gly Asp Gln Leu Leu Ala Phe Ala Glu Arg Asn Gly Met Gln
            580                 585                 590

Met Arg Gly His Thr Leu Ile Trp His Asn Gln Asn Pro Ser Trp Leu
    595                 600                 605

Thr Asn Gly Asn Trp Asn Arg Asp Ser Leu Leu Ala Val Met Lys Asn
610                 615                 620

His Ile Thr Thr Val Met Thr His Tyr Lys Gly Lys Ile Val Glu Trp
625                 630                 635                 640

Asp Val Ala Asn Glu Cys Met Asp Asp Ser Gly Asn Gly Leu Arg Ser
                645                 650                 655

Ser Ile Trp Arg Asn Val Ile Gly Gln Asp Tyr Leu Asp Tyr Ala Phe
            660                 665                 670

Arg Tyr Ala Arg Glu Ala Asp Pro Asp Ala Leu Leu Phe Tyr Asn Asp
        675                 680                 685

Tyr Asn Ile Glu Asp Leu Gly Pro Lys Ser Asn Ala Val Phe Asn Met
    690                 695                 700
```

```
Ile Lys Ser Met Lys Glu Arg Gly Val Pro I le Asp Gly Val Gly Phe
705                 710                 715                 720

Gln Cys His Phe Ile Asn Gly Met Ser Pro G lu Tyr Leu Ala Ser Ile
                725                 730                 735

Asp Gln Asn Ile Lys Arg Tyr Ala Glu Ile G ly Val Ile Val Ser Phe
            740                 745                 750

Thr Glu Ile Asp Ile Arg Ile Pro Gln Ser G lu Asn Pro Ala Thr Ala
            755                 760                 765

Phe Gln Val Gln Ala Asn Asn Tyr Lys Glu L eu Met Lys Ile Cys Leu
        770                 775                 780

Ala Asn Pro Asn Cys Asn Thr Phe Val Met T rp Gly Phe Thr Asp Lys
785                 790                 795                 800

Tyr Thr Trp Ile Pro Gly Thr Phe Pro Gly T yr Gly Asn Pro Leu Ile
                805                 810                 815

Tyr Asp Ser Asn Tyr Asn Pro Lys Pro Ala T yr Asn Ala Ile Lys Glu
            820                 825                 830

Ala Leu Met Gly Tyr
            835

<210> SEQ ID NO 15
<211> LENGTH: 3105
<212> TYPE: DNA
<213> ORGANISM: Ruminococcus sp.
<220> FEATURE:
<221> NAME/KEY: CDS
<222> LOCATION: (529)..(2895)

<400> SEQUENCE: 15
gatctttttc ataagtatgc ccccattatt aagtttttta gatgcttgcc t ataatttcc      60 cttctggttt tgtgaacttc ttaacggtca gagttcacac tttctttata t attgtctat     120 attataatgt atattgtagt aataatatac caaaattttc ctttaagtaa c aatatcttt     180 accctatttta gcaatttttta acgatatttt ataatttgat tattttttaaa c tatacagtg   240 taaatactat tatttaaaaa gtccaccaaa aatgtaaaat acaatgatat c ttaaacgta     300 aaaacctgta caatgattgt tcatcttttt acattattgt tatatatcgt c ttggtatag     360 tcagcaattt ttagtcaaga tatacaaggt ccgcaaattt taacttgcaa t taacaggtc     420 agatgtttta taatgatatc atagaaataa aaggagcact tggctcctta t ggggattac    480 tgaaatcata agtttgcttt ttttctaaaa aacaaaggag tgattgaa gtg aaa aaa       537
                                                      Val Lys Lys
                                                        1 aca gtt aaa caa ttc atc agc agt gcc gtt a ca gcg tta atg gtg gct      585
Thr Val Lys Gln Phe Ile Ser Ser Ala Val T hr Ala Leu Met Val Ala
    5                  10                  15 gca agc ctg cct gcc gtt cct tcc gtg aac g ca gcc gac gcc cag cag      633
Ala Ser Leu Pro Ala Val Pro Ser Val Asn A la Ala Asp Ala Gln Gln
 20                  25                 30                  35 aga ggc aat atc ggc ggt ttc gat tac gaa a tg tgg aac cag aac ggt      681
Arg Gly Asn Ile Gly Gly Phe Asp Tyr Glu M et Trp Asn Gln Asn Gly
                40                  45                  50 cag gga cag gta tca atg acg cct aag gca g gc tct ttc acc tgc tca      729
Gln Gly Gln Val Ser Met Thr Pro Lys Ala G ly Ser Phe Thr Cys Ser
             55                  60                  65 tgg agc aac att gaa aac ttc ctc gca cgt a tg ggc aag aac tac gac      777
Trp Ser Asn Ile Glu Asn Phe Leu Ala Arg M et Gly Lys Asn Tyr Asp
         70                  75                  80 agc cag aaa aag aac tac aag gct ttc gga g ac att acc ctc tcc tac      825
```

```
Ser Gln Lys Lys Asn Tyr Lys Ala Phe Gly A sp Ile Thr Leu Ser Tyr
    85              90                  95 gac gta gag tac acc ccc aag ggc aac tct t at atg tgc gta tac ggc        873
Asp Val Glu Tyr Thr Pro Lys Gly Asn Ser T yr Met Cys Val Tyr Gly
100             105                 110                 115 tgg acg agg aac cct ctc atg gaa tac tac a tc gtc gaa ggc tgg ggc        921
Trp Thr Arg Asn Pro Leu Met Glu Tyr Tyr I le Val Glu Gly Trp Gly
                120                 125                 130 gac tgg cgt cca ccc gga aat gac ggc gaa a ac aag ggt aca gtt acc        969
Asp Trp Arg Pro Pro Gly Asn Asp Gly Glu A sn Lys Gly Thr Val Thr
            135                 140                 145 ctg aac ggc aac acc tac gat atc cgc aaa a ca atg cgt tat aat cag       1017
Leu Asn Gly Asn Thr Tyr Asp Ile Arg Lys T hr Met Arg Tyr Asn Gln
        150                 155                 160 cca tct ctg gac ggc acg gct aca ttc cct c ag tac tgg agc gta cgt       1065
Pro Ser Leu Asp Gly Thr Ala Thr Phe Pro G ln Tyr Trp Ser Val Arg
    165                 170                 175 cag aag agc ggt tca cag aat aat acc acc a ac tat atg aag ggt act       1113
Gln Lys Ser Gly Ser Gln Asn Asn Thr Thr A sn Tyr Met Lys Gly Thr
180             185                 190                 195 atc agc gta tcc aag cac ttt gac gca tgg t ca aag gca ggt ctg gat       1161
Ile Ser Val Ser Lys His Phe Asp Ala Trp S er Lys Ala Gly Leu Asp
                200                 205                 210 atg agc ggt act ctc tac gag gta tcc ctc a ac atc gag ggc tac aga       1209
Met Ser Gly Thr Leu Tyr Glu Val Ser Leu A sn Ile Glu Gly Tyr Arg
            215                 220                 225 tca agc gga aac gct aac gtt aaa gct atc t ca ttc gac ggc agt ata       1257
Ser Ser Gly Asn Ala Asn Val Lys Ala Ile S er Phe Asp Gly Ser Ile
        230                 235                 240 ccc gag ccc aca agc gag ccc gta act cag c cc gtt gtc aag gca gag       1305
Pro Glu Pro Thr Ser Glu Pro Val Thr Gln P ro Val Val Lys Ala Glu
    245                 250                 255 cct gac gca aac ggc tac tac ttc aaa gaa a aa ttc gag agc ggc gca       1353
Pro Asp Ala Asn Gly Tyr Tyr Phe Lys Glu L ys Phe Glu Ser Gly Ala
260             265                 270                 275 ggc gac tgg tca gcc cgc gga aca gga gct a ag gta aca agc tct gac       1401
Gly Asp Trp Ser Ala Arg Gly Thr Gly Ala L ys Val Thr Ser Ser Asp
                280                 285                 290 gga ttc aac ggt tca aag ggc ata ctg gta t ca gga cgc ggc gac aac       1449
Gly Phe Asn Gly Ser Lys Gly Ile Leu Val S er Gly Arg Gly Asp Asn
            295                 300                 305 tgg cac ggc gca cag ctc aca ctc gac tca a gt gct ttc aca gca ggc       1497
Trp His Gly Ala Gln Leu Thr Leu Asp Ser S er Ala Phe Thr Ala Gly
        310                 315                 320 gaa aca tac agc ttc ggc gca ctt gta aag c ag gac ggc gag tcc tca       1545
Glu Thr Tyr Ser Phe Gly Ala Leu Val Lys G ln Asp Gly Glu Ser Ser
    325                 330                 335 aca gct atg aag ctc act ctc cag tat aac g ac gca agc ggc aca gcc       1593
Thr Ala Met Lys Leu Thr Leu Gln Tyr Asn A sp Ala Ser Gly Thr Ala
340             345                 350                 355 aat tac gat aag gtg gca gag ttc aca gct c ca aag ggt gaa tgg gta       1641
Asn Tyr Asp Lys Val Ala Glu Phe Thr Ala P ro Lys Gly Glu Trp Val
                360                 365                 370 gac ctt tcc aat aca tcg ttc act atc ccg t ca ggc gct tca gac ctc       1689
Asp Leu Ser Asn Thr Ser Phe Thr Ile Pro S er Gly Ala Ser Asp Leu
            375                 380                 385 att ctc tat gtt gaa gct ccc gac agc ctt a cg gat ttc tat atc gac       1737
Ile Leu Tyr Val Glu Ala Pro Asp Ser Leu T hr Asp Phe Tyr Ile Asp
        390                 395                 400
```

```
aac gct ttc ggc ggc atc aag aac aca tct c ct ctt gaa gat gtc gga    1785
Asn Ala Phe Gly Gly Ile Lys Asn Thr Ser P ro Leu Glu Asp Val Gly
        405                 410                 415 agc cat act atc agc act ccg ggc agc gag a ca aca aca gtc aca act    1833
Ser His Thr Ile Ser Thr Pro Gly Ser Glu T hr Thr Thr Val Thr Thr
420                 425                 430                 435 gca tca aat aag ggt atc aga ggc gat atc a ac ggc gac ggc gtt atc    1881
Ala Ser Asn Lys Gly Ile Arg Gly Asp Ile A sn Gly Asp Gly Val Ile
                440                 445                 450 aac tca ttc gac ctt gct cct ctc aga aga g gc att ctc aag atg atg    1929
Asn Ser Phe Asp Leu Ala Pro Leu Arg Arg G ly Ile Leu Lys Met Met
            455                 460                 465 tca ggc agc ggc tcg act ccc gaa aat gct g ac gta aac ggc gac ggc    1977
Ser Gly Ser Gly Ser Thr Pro Glu Asn Ala A sp Val Asn Gly Asp Gly
        470                 475                 480 act gta aat gtt gca gac ctc ctg ctt ctc c ag aag ttt ata ctc ggt    2025
Thr Val Asn Val Ala Asp Leu Leu Leu Leu G ln Lys Phe Ile Leu Gly
485                 490                 495 atg gag aag tca ttc ccc gat cct gta aca a ct acc acg acc aag ccg    2073
Met Glu Lys Ser Phe Pro Asp Pro Val Thr T hr Thr Thr Lys Pro
500                 505                 510                 515 ata aca aca act acc gag aag ata gtt acc a ca act act tct tca tct    2121
Ile Thr Thr Thr Thr Glu Lys Ile Val Thr T hr Thr Thr Ser Ser Ser
                520                 525                 530 tct tca agc tca ggc aag aac ctc aat gca g at atc cgc aag gat atg    2169
Ser Ser Ser Ser Gly Lys Asn Leu Asn Ala A sp Ile Arg Lys Asp Met
            535                 540                 545 cct act tca gtt ccc ggc gga aac gaa aag a gc ggc ggc tgc aag gtc    2217
Pro Thr Ser Val Pro Gly Gly Asn Glu Lys S er Gly Gly Cys Lys Val
        550                 555                 560 gag aag aag aca tac aac tgc aag ttc aca g gc ggt cag aag agc tgc    2265
Glu Lys Lys Thr Tyr Asn Cys Lys Phe Thr G ly Gly Gln Lys Ser Cys
565                 570                 575 aac gtt atc ctg cct cct aac tac agc gca a gc aag cag tac cct gtt    2313
Asn Val Ile Leu Pro Pro Asn Tyr Ser Ala S er Lys Gln Tyr Pro Val
580                 585                 590                 595 atg tac gtt ctc cac ggt atc ggc gga aac g ag gga agc atg gta agc    2361
Met Tyr Val Leu His Gly Ile Gly Gly Asn G lu Gly Ser Met Val Ser
                600                 605                 610 ggc atg ggc gtt cag gag ctt ctt gca gga c tt acc gca aac ggc aag    2409
Gly Met Gly Val Gln Glu Leu Leu Ala Gly L eu Thr Ala Asn Gly Lys
            615                 620                 625 gca gag gaa atg ata atc gtt ctc ccg agc c ag tac acc agc aag aac    2457
Ala Glu Glu Met Ile Ile Val Leu Pro Ser G ln Tyr Thr Ser Lys Asn
        630                 635                 640 ggc aat cag ggc ggc ggc ttc gga atc aat c ag gaa gta tgc gca gct    2505
Gly Asn Gln Gly Gly Gly Phe Gly Ile Asn G ln Glu Val Cys Ala Ala
645                 650                 655 tac gat aac ttc ctc tat gat atc tca gac a gc ctt atc cca ttc atc    2553
Tyr Asp Asn Phe Leu Tyr Asp Ile Ser Asp S er Leu Ile Pro Phe Ile
                660                 665                 670                 675 gag gct aac tat ccc gtt aag aca ggc aga g aa aac cgt gct atc aca    2601
Glu Ala Asn Tyr Pro Val Lys Thr Gly Arg G lu Asn Arg Ala Ile Thr
            680                 685                 690 ggc ttc tca atg ggc gga cgt gaa gct atc t at atc ggt ctt atg cgt    2649
Gly Phe Ser Met Gly Gly Arg Glu Ala Ile T yr Ile Gly Leu Met Arg
        695                 700                 705 ccc gac ctc ttc gct tac gtt ggc gga gct t gc cct gca ccc ggt atc    2697
Pro Asp Leu Phe Ala Tyr Val Gly Gly Ala C ys Pro Ala Pro Gly Ile
710                 715                 720
```

```
acc cca ggc aag gat atg ttc atg gag cac c ca ggc tgt atg cag gag        2745
Thr Pro Gly Lys Asp Met Phe Met Glu His P ro Gly Cys Met Gln Glu
        725                 730                 735 agc gaa atg aag ttc aga gac gtt gga cct g ag ccg aat gta ttc atg        2793
Ser Glu Met Lys Phe Arg Asp Val Gly Pro G lu Pro Asn Val Phe Met
740                 745                 750                 755 ata aca ggc ggc aca aac gac ggc gtc gta g ga aca ttc ccc aag cag        2841
Ile Thr Gly Gly Thr Asn Asp Gly Val Val G ly Thr Phe Pro Lys Gln
                760                 765                 770 tac agc gat atc ctt aca aga aac ggc gtt g ac caa cgt tta cca gtc        2889
Tyr Ser Asp Ile Leu Thr Arg Asn Gly Val A sp Gln Arg Leu Pro Val
            775                 780                 785 tat ccc taacggcgga cacgacgcag gctctgtaaa gcctcatctc t acacattca         2945
Tyr Pro tgagatacgc attcaaataa tgatatagtt gacatatgaa ggacagcgct t tatgcgctg      3005 tctttctttt tgtgcaaaaa gaaaagccat ttgagctttt gaagctcaaa t ggcttatat     3065 ttataatagt atagcttatt ctgttctgag agcctccaca                             3105
```

<210> SEQ ID NO 16
<211> LENGTH: 789
<212> TYPE: PRT
<213> ORGANISM: Ruminococcus sp.

<400> SEQUENCE: 16

```
Val Lys Lys Thr Val Lys Gln Phe Ile Ser S er Ala Val Thr Ala Leu
 1               5                  10                  15

Met Val Ala Ala Ser Leu Pro Ala Val Pro S er Val Asn Ala Ala Asp
            20                  25                  30

Ala Gln Gln Arg Gly Asn Ile Gly Gly Phe A sp Tyr Glu Met Trp Asn
        35                  40                  45

Gln Asn Gly Gln Gly Gln Val Ser Met Thr P ro Lys Ala Gly Ser Phe
    50                  55                  60

Thr Cys Ser Trp Ser Asn Ile Glu Asn Phe L eu Ala Arg Met Gly Lys
65                  70                  75                  80

Asn Tyr Asp Ser Gln Lys Lys Asn Tyr Lys A la Phe Gly Asp Ile Thr
                85                  90                  95

Leu Ser Tyr Asp Val Glu Tyr Thr Pro Lys G ly Asn Ser Tyr Met Cys
            100                 105                 110

Val Tyr Gly Trp Thr Arg Asn Pro Leu Met G lu Tyr Tyr Ile Val Glu
        115                 120                 125

Gly Trp Gly Asp Trp Arg Pro Pro Gly Asn A sp Gly Glu Asn Lys Gly
    130                 135                 140

Thr Val Thr Leu Asn Gly Asn Thr Tyr Asp I le Arg Lys Thr Met Arg
145                 150                 155                 160

Tyr Asn Gln Pro Ser Leu Asp Gly Thr Ala T hr Phe Pro Gln Tyr Trp
                165                 170                 175

Ser Val Arg Gln Lys Ser Gly Ser Gln Asn A sn Thr Thr Asn Tyr Met
            180                 185                 190

Lys Gly Thr Ile Ser Val Ser Lys His Phe A sp Ala Trp Ser Lys Ala
        195                 200                 205

Gly Leu Asp Met Ser Gly Thr Leu Tyr Glu V al Ser Leu Asn Ile Glu
    210                 215                 220

Gly Tyr Arg Ser Ser Gly Asn Ala Asn Val L ys Ala Ile Ser Phe Asp
225                 230                 235                 240
```

```
Gly Ser Ile Pro Glu Pro Thr Ser Glu Pro Val Thr Gln Pro Val Val
                245                 250                 255

Lys Ala Glu Pro Asp Ala Asn Gly Tyr Tyr Phe Lys Glu Lys Phe Glu
            260                 265                 270

Ser Gly Ala Gly Asp Trp Ser Ala Arg Gly Thr Gly Ala Lys Val Thr
        275                 280                 285

Ser Ser Asp Gly Phe Asn Gly Ser Lys Gly Ile Leu Val Ser Gly Arg
    290                 295                 300

Gly Asp Asn Trp His Gly Ala Gln Leu Thr Leu Asp Ser Ser Ala Phe
305                 310                 315                 320

Thr Ala Gly Glu Thr Tyr Ser Phe Gly Ala Leu Val Lys Gln Asp Gly
                325                 330                 335

Glu Ser Ser Thr Ala Met Lys Leu Thr Leu Gln Tyr Asn Asp Ala Ser
            340                 345                 350

Gly Thr Ala Asn Tyr Asp Lys Val Ala Glu Phe Thr Ala Pro Lys Gly
        355                 360                 365

Glu Trp Val Asp Leu Ser Asn Thr Ser Phe Thr Ile Pro Ser Gly Ala
    370                 375                 380

Ser Asp Leu Ile Leu Tyr Val Glu Ala Pro Asp Ser Leu Thr Asp Phe
385                 390                 395                 400

Tyr Ile Asp Asn Ala Phe Gly Ile Lys Asn Thr Ser Pro Leu Glu
                405                 410                 415

Asp Val Gly Ser His Thr Ile Ser Thr Pro Gly Ser Glu Thr Thr Thr
            420                 425                 430

Val Thr Thr Ala Ser Asn Lys Gly Ile Arg Gly Asp Ile Asn Gly Asp
        435                 440                 445

Gly Val Ile Asn Ser Phe Asp Leu Ala Pro Leu Arg Arg Gly Ile Leu
    450                 455                 460

Lys Met Met Ser Gly Ser Gly Ser Thr Pro Glu Asn Ala Asp Val Asn
465                 470                 475                 480

Gly Asp Gly Thr Val Asn Val Ala Asp Leu Leu Leu Leu Gln Lys Phe
                485                 490                 495

Ile Leu Gly Met Glu Lys Ser Phe Pro Asp Pro Val Thr Thr Thr Thr
            500                 505                 510

Thr Lys Pro Ile Thr Thr Thr Glu Lys Ile Val Thr Thr Thr Thr
        515                 520                 525

Ser Ser Ser Ser Ser Ser Gly Lys Asn Leu Asn Ala Asp Ile Arg
    530                 535                 540

Lys Asp Met Pro Thr Ser Val Pro Gly Gly Asn Glu Lys Ser Gly Gly
545                 550                 555                 560

Cys Lys Val Glu Lys Lys Thr Tyr Asn Cys Lys Phe Thr Gly Gly Gln
                565                 570                 575

Lys Ser Cys Asn Val Ile Leu Pro Pro Asn Tyr Ser Ala Ser Lys Gln
            580                 585                 590

Tyr Pro Val Met Tyr Val Leu His Gly Ile Gly Gly Asn Glu Gly Ser
        595                 600                 605

Met Val Ser Gly Met Gly Val Gln Glu Leu Leu Ala Gly Leu Thr Ala
    610                 615                 620

Asn Gly Lys Ala Glu Glu Met Ile Ile Val Leu Pro Ser Gln Tyr Thr
625                 630                 635                 640

Ser Lys Asn Gly Asn Gln Gly Gly Phe Gly Ile Asn Gln Glu Val
                645                 650                 655
```

```
Cys Ala Ala Tyr Asp Asn Phe Leu Tyr Asp Ile Ser Asp Ser Leu Ile
            660                 665                 670

Pro Phe Ile Glu Ala Asn Tyr Pro Val Lys Thr Gly Arg Glu Asn Arg
            675                 680                 685

Ala Ile Thr Gly Phe Ser Met Gly Gly Arg Glu Ala Ile Tyr Ile Gly
            690                 695                 700

Leu Met Arg Pro Asp Leu Phe Ala Tyr Val Gly Gly Ala Cys Pro Ala
705                 710                 715                 720

Pro Gly Ile Thr Pro Gly Lys Asp Met Phe Met Glu His Pro Gly Cys
                725                 730                 735

Met Gln Glu Ser Glu Met Lys Phe Arg Asp Val Gly Pro Glu Pro Asn
            740                 745                 750

Val Phe Met Ile Thr Gly Gly Thr Asn Asp Gly Val Val Gly Thr Phe
            755                 760                 765

Pro Lys Gln Tyr Ser Asp Ile Leu Thr Arg Asn Gly Val Asp Gln Arg
            770                 775                 780

Leu Pro Val Tyr Pro
785

<210> SEQ ID NO 17
<211> LENGTH: 1662
<212> TYPE: DNA
<213> ORGANISM: Orpinomyces sp. PC-2
<220> FEATURE:
<221> NAME/KEY: CDS
<222> LOCATION: (1)..(1590)

<400> SEQUENCE: 17 gtt gtt tct tgt gaa act act tac ggt att act tta cgt gat act aag     48
Val Val Ser Cys Glu Thr Thr Tyr Gly Ile Thr Leu Arg Asp Thr Lys
  1               5                  10                  15 gaa aaa ttc act gta ttc aaa gac ggt tcc gct gct act gat att gtt     96
Glu Lys Phe Thr Val Phe Lys Asp Gly Ser Ala Ala Thr Asp Ile Val
             20                  25                  30 gaa tca gaa gat ggt tcc gtt tct tgg att gct act gct gcc ggt ggt    144
Glu Ser Glu Asp Gly Ser Val Ser Trp Ile Ala Thr Ala Ala Gly Gly
         35                  40                  45 gct ggt ggt ggt gtt gcc ttc tat gtt aag gct aac aag gaa gaa att    192
Ala Gly Gly Gly Val Ala Phe Tyr Val Lys Ala Asn Lys Glu Glu Ile
     50                  55                  60 aac att gct aac tat gaa tct atc gat att gaa atg gaa tac act cca    240
Asn Ile Ala Asn Tyr Glu Ser Ile Asp Ile Glu Met Glu Tyr Thr Pro
 65                  70                  75                  80 gtt gaa aac aaa tgg aat gat gct gct aag aac cca agt ttc tgt atg    288
Val Glu Asn Lys Trp Asn Asp Ala Ala Lys Asn Pro Ser Phe Cys Met
                 85                  90                  95 aga att ctt cca tgg gat tcc act ggt atg ttc ggt ggt tac gaa gat    336
Arg Ile Leu Pro Trp Asp Ser Thr Gly Met Phe Gly Gly Tyr Glu Asp
            100                 105                 110 ctt gaa tac ttc gat act cca gca aaa tct ggt aat ttc aaa tac act    384
Leu Glu Tyr Phe Asp Thr Pro Ala Lys Ser Gly Asn Phe Lys Tyr Thr
        115                 120                 125 att aag att cct tcc ttc ttt gct gat aag att tta tct agc tct gat    432
Ile Lys Ile Pro Ser Phe Phe Ala Asp Lys Ile Leu Ser Ser Ser Asp
    130                 135                 140 ctc gat tct atc tta agt ttt gct atc aag ttc aac gat tat gaa aga    480
Leu Asp Ser Ile Leu Ser Phe Ala Ile Lys Phe Asn Asp Tyr Glu Arg
145                 150                 155                 160 ggt aac acg gac ggt gac caa att aag att caa tta aag aat gtt aaa    528
```

```
                    Gly Asn Thr Asp Gly Asp Gln Ile Lys Ile G ln Leu Lys Asn Val Lys
                                    165                 170                 175 ttc aac cca aag gaa aat gct cca gaa gat a ag gct ttc gat gat ggt              576
Phe Asn Pro Lys Glu Asn Ala Pro Glu Asp L ys Ala Phe Asp Asp Gly
                180                 185                 190 tta agg gat tct caa cgt ggt act gtc gtt g aa atg aaa tac tca tct              624
Leu Arg Asp Ser Gln Arg Gly Thr Val Val G lu Met Lys Tyr Ser Ser
            195                 200                 205 aga gat tac acc gtc aag gaa tct gaa gct g ac aaa tac gaa aag cac              672
Arg Asp Tyr Thr Val Lys Glu Ser Glu Ala A sp Lys Tyr Glu Lys His
        210                 215                 220 gct tgg gtt tac ctt cca gct ggt tat gaa g ct gat aac aag gat aag              720
Ala Trp Val Tyr Leu Pro Ala Gly Tyr Glu A la Asp Asn Lys Asp Lys
225                 230                 235                 240 aaa tac cca tta gtt gtt tta ctt cac ggt t at ggt caa aat gaa aac              768
Lys Tyr Pro Leu Val Val Leu Leu His Gly T yr Gly Gln Asn Glu Asn
                245                 250                 255 act tgg ggt ctt tcc aac aag ggt cgt ggt g gt aag atc aag ggt tac              816
Thr Trp Gly Leu Ser Asn Lys Gly Arg Gly G ly Lys Ile Lys Gly Tyr
            260                 265                 270 atg gac aga ggt atg gct agt ggt aat gtt g aa aag ttt gtt ctt gtt              864
Met Asp Arg Gly Met Ala Ser Gly Asn Val G lu Lys Phe Val Leu Val
        275                 280                 285 gcc gct act ggt gtt gcc agt aag aat tgg g gt cca aac ggt tct ggt              912
Ala Ala Thr Gly Val Ala Ser Lys Asn Trp G ly Pro Asn Gly Ser Gly
    290                 295                 300 gtt gat ctt gat ggt ttc aat gct ttc ggt g gt gaa ctc aga aac gat              960
Val Asp Leu Asp Gly Phe Asn Ala Phe Gly G ly Glu Leu Arg Asn Asp
305                 310                 315                 320 tta ctc cca tac att aga gct cac ttc aat g tt aag gtc gat cgt gat             1008
Leu Leu Pro Tyr Ile Arg Ala His Phe Asn V al Lys Val Asp Arg Asp
                325                 330                 335 cac act gct tta gct ggt ctt tcc atg ggt g gt ggt caa act atc agt             1056
His Thr Ala Leu Ala Gly Leu Ser Met Gly G ly Gly Gln Thr Ile Ser
            340                 345                 350 att ggt att ggt gaa act ctt gat gaa atc a gt aac tac ggt tct ttc             1104
Ile Gly Ile Gly Glu Thr Leu Asp Glu Ile S er Asn Tyr Gly Ser Phe
        355                 360                 365 tct cca gct tta ttc caa act gct gaa gaa t tc ttc ggt aag gtt aag             1152
Ser Pro Ala Leu Phe Gln Thr Ala Glu Glu P he Phe Gly Lys Val Lys
    370                 375                 380 ggt aac ttc aag gaa gaa ctt aga att cac a ac ctt tac atg act tgt             1200
Gly Asn Phe Lys Glu Glu Leu Arg Ile His A sn Leu Tyr Met Thr Cys
385                 390                 395                 400 ggt gat gct gat act tta gtt tac gat act t ac cca agt tac gtt gaa             1248
Gly Asp Ala Asp Thr Leu Val Tyr Asp Thr T yr Pro Ser Tyr Val Glu
                405                 410                 415 gct tta aag aat tgg gat gct gtt gaa ttc a tg aag gaa tac act tac             1296
Ala Leu Lys Asn Trp Asp Ala Val Glu Phe M et Lys Glu Tyr Thr Tyr
            420                 425                 430 cca ggt ggt act cac gat ttc cca gtt tgg t ac aga ggt ttc aac gaa             1344
Pro Gly Gly Thr His Asp Phe Pro Val Trp T yr Arg Gly Phe Asn Glu
        435                 440                 445 ttc att caa att gtt ttc aaa aat caa aaa g tt aag gaa gaa cca att             1392
Phe Ile Gln Ile Val Phe Lys Asn Gln Lys V al Lys Glu Glu Pro Ile
    450                 455                 460 cat gct gat cca gta gaa gac cca tct gat g aa cca gtt agt gtt gat             1440
His Ala Asp Pro Val Glu Asp Pro Ser Asp G lu Pro Val Ser Val Asp
465                 470                 475                 480
```

```
cca tct gtt tct gtc gaa gaa cca aat gac a gt gaa tct tcc tct gaa    1488
Pro Ser Val Ser Val Glu Glu Pro Asn Asp S er Glu Ser Ser Glu
                485                 490                 495 gat gaa cca gtg gtt aaa aaa act att aag c ac acc att gct aag aag    1536
Asp Glu Pro Val Val Lys Lys Thr Ile Lys H is Thr Ile Ala Lys Lys
        500                 505                 510 aag cca tct aag act aga act gtt acc aag a ag gtc att aag aag aag    1584
Lys Pro Ser Lys Thr Arg Thr Val Thr Lys L ys Val Ile Lys Lys Lys
            515                 520                 525 aat aac taagaaagtt tagttagtac agtagtgtaa aaaaaaaaa a aaatcaaaa      1640
Asn Asn
    530 agaaactcgt gccgaattcg at                                           1662

<210> SEQ ID NO 18
<211> LENGTH: 530
<212> TYPE: PRT
<213> ORGANISM: Orpinomyces sp. PC-2

<400> SEQUENCE: 18

Val Val Ser Cys Glu Thr Thr Tyr Gly Ile T hr Leu Arg Asp Thr Lys
  1               5                  10                  15

Glu Lys Phe Thr Val Phe Lys Asp Gly Ser A la Ala Thr Asp Ile Val
             20                  25                  30

Glu Ser Glu Asp Gly Ser Val Ser Trp Ile A la Thr Ala Gly Gly
         35                  40                  45

Ala Gly Gly Gly Val Ala Phe Tyr Val Lys A la Asn Lys Glu Glu Ile
     50                  55                  60

Asn Ile Ala Asn Tyr Glu Ser Ile Asp Ile G lu Met Glu Tyr Thr Pro
 65                  70                  75                   80

Val Glu Asn Lys Trp Asn Asp Ala Ala Lys A sn Pro Ser Phe Cys Met
                 85                  90                   95

Arg Ile Leu Pro Trp Asp Ser Thr Gly Met P he Gly Gly Tyr Glu Asp
            100                 105                 110

Leu Glu Tyr Phe Asp Thr Pro Ala Lys Ser G ly Asn Phe Lys Tyr Thr
        115                 120                 125

Ile Lys Ile Pro Ser Phe Phe Ala Asp Lys I le Leu Ser Ser Ser Asp
    130                 135                 140

Leu Asp Ser Ile Leu Ser Phe Ala Ile Lys P he Asn Asp Tyr Glu Arg
145                 150                 155                 160

Gly Asn Thr Asp Gly Asp Gln Ile Lys Ile G ln Leu Lys Asn Val Lys
                165                 170                 175

Phe Asn Pro Lys Glu Asn Ala Pro Glu Asp L ys Ala Phe Asp Asp Gly
            180                 185                 190

Leu Arg Asp Ser Gln Arg Gly Thr Val Val G lu Met Lys Tyr Ser Ser
        195                 200                 205

Arg Asp Tyr Thr Val Lys Glu Ser Glu Ala A sp Lys Tyr Glu Lys His
    210                 215                 220

Ala Trp Val Tyr Leu Pro Ala Gly Tyr Glu A la Asp Asn Lys Asp Lys
225                 230                 235                 240

Lys Tyr Pro Leu Val Val Leu Leu His Gly T yr Gly Gln Asn Glu Asn
                245                 250                 255

Thr Trp Gly Leu Ser Asn Lys Gly Arg Gly G ly Lys Ile Lys Gly Tyr
            260                 265                 270

Met Asp Arg Gly Met Ala Ser Gly Asn Val G lu Lys Phe Val Leu Val
        275                 280                 285
```

-continued

```
Ala Ala Thr Gly Val Ala Ser Lys Asn Trp Gly Pro Asn Gly Ser Gly
        290                 295                 300
Val Asp Leu Asp Gly Phe Asn Ala Phe Gly Gly Glu Leu Arg Asn Asp
305                 310                 315                 320
Leu Leu Pro Tyr Ile Arg Ala His Phe Asn Val Lys Val Asp Arg Asp
                325                 330                 335
His Thr Ala Leu Ala Gly Leu Ser Met Gly Gly Gln Thr Ile Ser
            340                 345                 350
Ile Gly Ile Gly Glu Thr Leu Asp Glu Ile Ser Asn Tyr Gly Ser Phe
        355                 360                 365
Ser Pro Ala Leu Phe Gln Thr Ala Glu Glu Phe Phe Gly Lys Val Lys
    370                 375                 380
Gly Asn Phe Lys Glu Glu Leu Arg Ile His Asn Leu Tyr Met Thr Cys
385                 390                 395                 400
Gly Asp Ala Asp Thr Leu Val Tyr Asp Thr Tyr Pro Ser Tyr Val Glu
                405                 410                 415
Ala Leu Lys Asn Trp Asp Ala Val Glu Phe Met Lys Glu Tyr Thr Tyr
            420                 425                 430
Pro Gly Gly Thr His Asp Phe Pro Val Trp Tyr Arg Gly Phe Asn Glu
        435                 440                 445
Phe Ile Gln Ile Val Phe Lys Asn Gln Lys Val Lys Glu Glu Pro Ile
    450                 455                 460
His Ala Asp Pro Val Glu Asp Pro Ser Asp Glu Pro Val Ser Val Asp
465                 470                 475                 480
Pro Ser Val Ser Val Glu Glu Pro Asn Asp Ser Glu Ser Ser Ser Glu
                485                 490                 495
Asp Glu Pro Val Val Lys Lys Thr Ile Lys His Thr Ile Ala Lys Lys
            500                 505                 510
Lys Pro Ser Lys Thr Arg Thr Val Thr Lys Lys Val Ile Lys Lys Lys
        515                 520                 525
Asn Asn
    530

<210> SEQ ID NO 19
<211> LENGTH: 400
<212> TYPE: PRT
<213> ORGANISM: Escherichia coli

<400> SEQUENCE: 19

Met Val Met Glu Leu Asn Glu Arg Asn Ile Thr Met Asn Ile Lys Ile
 1               5                  10                  15
Ala Ala Leu Thr Leu Ala Ile Ala Ser Gly Ile Ser Ala Gln Trp Ala
            20                  25                  30
Ile Ala Ala Asp Met Pro Ala Ser Pro Ala Pro Thr Ile Pro Val Lys
        35                  40                  45
Gln Tyr Val Thr Gln Val Asn Ala Asp Asn Ser Val Thr Phe Arg Tyr
    50                  55                  60
Phe Ala Pro Gly Ala Lys Asn Val Ser Val Val Val Gly Val Pro Val
65                  70                  75                  80
Pro Asp Asn Ile His Pro Met Thr Lys Asp Glu Ala Gly Val Trp Ser
                85                  90                  95
Trp Arg Thr Pro Ile Leu Lys Gly Asn Leu Tyr Glu Tyr Phe Phe Asn
            100                 105                 110
Val Asp Gly Val Arg Ser Ile Asp Thr Gly Thr Ala Met Thr Asn Pro
```

-continued

```
               115                 120                 125
Gln Arg Gln Val Asn Ser Ser Met Ile Leu Val Pro Gly Ser Tyr Leu
        130                 135                 140

Asp Thr Arg Ser Val Ala His Gly Asp Leu Ile Ala Ile Thr Tyr His
145                 150                 155                 160

Ser Asn Ala Leu Gln Ser Glu Arg Gln Met Tyr Val Trp Thr Pro Pro
                165                 170                 175

Gly Tyr Thr Gly Met Gly Glu Pro Leu Pro Val Leu Tyr Phe Tyr His
            180                 185                 190

Gly Phe Gly Asp Thr Gly Arg Ser Ala Ile Asp Gln Gly Arg Ile Pro
            195                 200                 205

Gln Ile Met Asp Asn Leu Leu Ala Glu Gly Lys Ile Lys Pro Met Leu
        210                 215                 220

Val Val Ile Pro Asp Thr Glu Thr Asp Ala Lys Gly Ile Ile Pro Glu
225                 230                 235                 240

Asp Phe Val Pro Gln Glu Arg Arg Lys Val Phe Tyr Pro Leu Asn Ala
                245                 250                 255

Lys Ala Ala Asp Arg Glu Leu Met Asn Asp Ile Ile Pro Leu Ile Ser
            260                 265                 270

Lys Arg Phe Asn Val Arg Lys Asp Ala Asp Gly Arg Ala Leu Ala Gly
        275                 280                 285

Leu Ser Gln Gly Gly Tyr Gln Ala Leu Val Ser Gly Met Asn His Leu
        290                 295                 300

Glu Ser Phe Gly Trp Leu Ala Thr Phe Ser Gly Val Thr Thr Thr Thr
305                 310                 315                 320

Val Pro Asp Glu Gly Val Ala Ala Arg Leu Asn Asp Pro Ala Ala Ile
                325                 330                 335

Asn Gln Gln Leu Arg Asn Phe Thr Val Val Val Gly Asp Lys Asp Val
            340                 345                 350

Val Thr Gly Lys Asp Ile Ala Gly Leu Lys Thr Glu Leu Glu Gln Lys
            355                 360                 365

Lys Ile Asn Phe Asp Tyr Gln Glu Tyr Pro Gly Leu Asn His Glu Met
        370                 375                 380

Asp Val Trp Arg Pro Ala Tyr Ala Ala Phe Val Gln Lys Leu Phe Lys
385                 390                 395                 400

<210> SEQ ID NO 20
<211> LENGTH: 721
<212> TYPE: PRT
<213> ORGANISM: Aspergillus fumigatus

<400> SEQUENCE: 20

Met Gly Ala Phe Arg Trp Leu Ser Ile Ala Ala Ala Ala Ser Thr Ala
1               5                   10                  15

Leu Ala Leu Thr Pro Glu Gln Leu Ile Thr Ala Pro Arg Arg Ser Glu
            20                  25                  30

Ala Ile Pro Asp Pro Ser Gly Lys Val Ala Val Phe Ser Thr Ser Gln
        35                  40                  45

Tyr Ser Phe Glu Thr His Lys Arg Thr Ser Trp Trp Ser Leu Leu Asp
    50                  55                  60

Leu Lys Thr Gly Gln Thr Lys Val Leu Thr Asn Asp Ser Ser Val Ser
65                  70                  75                  80

Glu Ile Val Trp Leu Ser Asp Asp Ser Ile Leu Tyr Val Asn Ser Thr
                85                  90                  95
```

```
Asn Ala Asp Ile Pro Gly Gly Val Glu Leu Trp Val Thr Gln Ala Ser
            100                 105                 110
Ser Phe Ala Lys Gly Tyr Lys Ala Ala Ser Leu Pro Ala Ser Phe Ser
            115                 120                 125
Gly Leu Lys Ala Ala Lys Thr Lys Ser Gly Asp Ile Arg Phe Val Ala
            130                 135                 140
Tyr Gly Gln Ser Tyr Pro Asn Gly Thr Ala Tyr Asn Glu Glu Leu Ala
145                 150                 155                 160
Thr Ala Pro Leu Ser Ser Ala Arg Ile Tyr Asp Ser Ile Tyr Val Arg
                    165                 170                 175
His Trp Asp Tyr Trp Leu Ser Thr Thr Phe Asn Ala Val Phe Ser Gly
            180                 185                 190
Thr Leu Lys Lys Gly His Gly Lys Asn Gly Tyr Ser Leu Asp Gly Glu
            195                 200                 205
Leu Lys Asn Leu Val Ser Pro Val Lys Asn Ala Glu Ser Pro Tyr Pro
            210                 215                 220
Pro Phe Gly Gly Ala Ser Asp Tyr Asp Leu Ser Pro Asp Gly Lys Trp
225                 230                 235                 240
Val Ala Phe Lys Ser Lys Ala Pro Glu Leu Pro Lys Ala Asn Phe Thr
                245                 250                 255
Thr Ser Tyr Ile Tyr Leu Val Pro His Asp Ala Ser Glu Thr Ala Arg
            260                 265                 270
Pro Ile Asn Gly Pro Asp Ser Pro Gly Thr Pro Lys Gly Ile Lys Gly
            275                 280                 285
Asp Ser Ser Pro Val Phe Ser Pro Asn Gly Asp Lys Leu Ala Tyr
            290                 295                 300
Phe Gln Met Arg Asp Glu Thr Tyr Glu Ser Asp Arg Ala Leu Leu Tyr
305                 310                 315                 320
Val Tyr Ser Leu Gly Ser Lys Lys Thr Ile Pro Ser Val Ala Gly Asp
                325                 330                 335
Trp Asp Arg Ser Pro Asp Ser Val Lys Trp Thr Pro Asp Gly Lys Thr
            340                 345                 350
Leu Ile Val Gly Ser Glu Asp Leu Gly Arg Thr Arg Leu Phe Ser Leu
            355                 360                 365
Pro Ala Asn Ala Lys Asp Asp Tyr Lys Pro Lys Asn Phe Thr Asp Gly
            370                 375                 380
Gly Ser Val Ser Ala Tyr Tyr Phe Leu Pro Asp Ser Ser Leu Leu Val
385                 390                 395                 400
Thr Gly Ser Ala Leu Trp Thr Asn Trp Asn Val Tyr Thr Ala Lys Pro
                405                 410                 415
Glu Lys Gly Val Ile Lys Lys Ile Ala Ser Ala Asn Glu Ile Asp Pro
            420                 425                 430
Glu Leu Lys Gly Leu Gly Pro Ser Asp Ile Ser Glu Phe Tyr Phe Gln
            435                 440                 445
Gly Asn Phe Thr Asp Ile His Ala Trp Val Ile Tyr Pro Glu Asn Phe
            450                 455                 460
Asp Lys Ser Lys Lys Tyr Pro Leu Ile Phe Phe Ile His Gly Gly Pro
465                 470                 475                 480
Gln Gly Asn Trp Ala Asp Gly Trp Ser Thr Arg Trp Asn Pro Lys Ala
                485                 490                 495
Trp Ala Asp Gln Gly Tyr Val Val Ala Pro Asn Pro Thr Gly Ser
            500                 505                 510
Thr Gly Phe Gly Gln Ala Leu Thr Thr Ala Ile Gln Asn Asn Trp Gly
```

-continued

```
                 515                 520                      525
Gly Ala Pro Tyr Asp Asp Leu Val Lys Cys T rp Glu Tyr Val His Glu
            530                 535                 540

Asn Leu Asp Tyr Val Asp Thr Asp His Gly V al Ala Ala Gly Ala Ser
545                 550                 555                 560

Tyr Gly Gly Phe Met Ile Asn Trp Ile Gln G ly Ser Pro Leu Gly Arg
                565                 570                 575

Lys Phe Lys Ala Leu Val Ser His Asp Gly T hr Phe Val Ala Asp Ala
            580                 585                 590

Lys Val Ser Thr Glu Glu Leu Trp Phe Met G ln Arg Glu Phe Asn Gly
            595                 600                 605

Thr Phe Trp Asp Ala Arg Asp Asn Tyr Arg A rg Trp Asp Pro Ser Ala
    610                 615                 620

Pro Glu Arg Ile Leu Gln Phe Ala Thr Pro M et Leu Val Ile His Ser
625                 630                 635                 640

Asp Lys Asp Tyr Arg Leu Pro Val Ala Glu G ly Leu Ser Leu Phe Asn
                645                 650                 655

Val Leu Gln Glu Arg Gly Val Pro Ser Arg P he Leu Asn Phe Pro Asp
            660                 665                 670

Glu Asn His Trp Val Val Asn Pro Glu Asn S er Leu Val Trp His Gln
            675                 680                 685

Gln Ala Leu Gly Trp Ile Asn Lys Tyr Ser G ly Val Glu Lys Ser Asn
            690                 695                 700

Pro Asn Ala Val Ser Leu Glu Asp Thr Val V al Pro Val Val Asn Tyr
705                 710                 715                 720

Asn

<210> SEQ ID NO 21
<211> LENGTH: 20
<212> TYPE: PRT
<213> ORGANISM: Orpinomyces sp. PC-2
<220> FEATURE:
<223> OTHER INFORMATION: Description of Artificial  Sequence:N-terminal
      amino acid sequence of a feruloy l esterase of
      Orpinomyces PC-2.

<400> SEQUENCE: 21

Glu Thr Thr Tyr Gly Ile Thr Leu Arg Asp T hr Lys Glu Lys Phe Thr
  1               5                  10                  15

Val Phe Lys Asp
             20

<210> SEQ ID NO 22
<211> LENGTH: 400
<212> TYPE: PRT
<213> ORGANISM: Escherichia coli

<400> SEQUENCE: 22

Met Val Met Glu Leu Asn Glu Arg Asn Ile T hr Met Asn Ile Lys Ile
  1               5                  10                  15

Ala Ala Leu Thr Leu Ala Ile Ala Ser Gly I le Ser Ala Gln Trp Ala
             20                  25                  30

Ile Ala Ala Asp Met Pro Ala Ser Pro Ala P ro Thr Ile Pro Val Lys
         35                  40                  45

Gln Tyr Val Thr Gln Val Asn Ala Asp Asn S er Val Thr Phe Arg Tyr
     50                  55                  60

Phe Ala Pro Gly Ala Lys Asn Val Ser Val V al Val Gly Val Pro Val
```

```
                 65                  70                  75                  80
         Pro Asp Asn Ile His Pro Met Thr Lys Asp G lu Ala Gly Val Trp Ser
                              85                  90                  95

Trp Arg Thr Pro Ile Leu Lys Gly Asn Leu T yr Glu Tyr Phe Phe Asn
                         100                 105                 110

Val Asp Gly Val Arg Ser Ile Asp Thr Gly T hr Ala Met Thr Asn Pro
                         115                 120                 125

Gln Arg Gln Val Asn Ser Ser Met Ile Leu V al Pro Gly Ser Tyr Leu
                         130                 135                 140

Asp Thr Arg Ser Val Ala His Gly Asp Leu I le Ala Ile Thr Tyr His
         145                 150                 155                 160

Ser Asn Ala Leu Gln Ser Glu Arg Gln Met T yr Val Trp Thr Pro Pro
                         165                 170                 175

Gly Tyr Thr Gly Met Gly Glu Pro Leu Pro V al Leu Tyr Phe Tyr His
                         180                 185                 190

Gly Phe Gly Asp Thr Gly Arg Ser Ala Ile A sp Gln Gly Arg Ile Pro
                         195                 200                 205

Gln Ile Met Asp Asn Leu Leu Ala Glu Gly L ys Ile Lys Pro Met Leu
                         210                 215                 220

Val Val Ile Pro Asp Thr Glu Thr Asp Ala L ys Gly Ile Ile Pro Glu
         225                 230                 235                 240

Asp Phe Val Pro Gln Glu Arg Arg Lys Val P he Tyr Pro Leu Asn Ala
                         245                 250                 255

Lys Ala Ala Asp Arg Glu Leu Met Asn Asp I le Ile Pro Leu Ile Ser
                         260                 265                 270

Lys Arg Phe Asn Val Arg Lys Asp Ala Asp G ly Arg Ala Leu Ala Gly
                         275                 280                 285

Leu Ser Gln Gly Gly Tyr Gln Ala Leu Val S er Gly Met Asn His Leu
                         290                 295                 300

Glu Ser Phe Gly Trp Leu Ala Thr Phe Ser G ly Val Thr Thr Thr Thr
         305                 310                 315                 320

Val Pro Asp Glu Gly Val Ala Ala Arg Leu A sn Asp Pro Ala Ala Ile
                         325                 330                 335

Asn Gln Gln Leu Arg Asn Phe Thr Val Val V al Gly Asp Lys Asp Val
                         340                 345                 350

Val Thr Gly Lys Asp Ile Ala Gly Leu Lys T hr Glu Leu Glu Gln Lys
                         355                 360                 365

Lys Ile Asn Phe Asp Tyr Gln Glu Tyr Pro G ly Leu Asn His Glu Met
                         370                 375                 380

Asp Val Trp Arg Pro Ala Tyr Ala Ala Phe V al Gln Lys Leu Phe Lys
         385                 390                 395                 400

<210> SEQ ID NO 23
<211> LENGTH: 2364
<212> TYPE: DNA
<213> ORGANISM: Clostridium stercorarium
<220> FEATURE:
<221> NAME/KEY: CDS
<222> LOCATION: (440)..(1975)

<400> SEQUENCE: 23
aagcttaatt tgtttggtat accttgcttt atgttcaatc acgttctcgt c attaaacaa      60 cccatataag ctgctccctg accggaaagt tgaacattga ttcttgcatt c cgaatctgc     120 tccaataaaa catttctgaa tttcgagacg gcaaaaaatg atgccgcttc c atttcaaca    180
```

-continued

```
gtaacacagc cttctgcaat cctttcgtc agcttccttt aaattttaag t ttgtctatt      240 gacaaaacta aaaactgtaa ttactataaa aatataacta ataaattaca t ttttaacat      300 cattatgggg tactggtaaa gacgtgatag ttattaataa atttaacaaa t aataacaca      360 ctgctatctt cgaccgtaaa tttactatgt ctctaatgta atatgacata a ataatataa      420 gtaaaggagg taaaagtttt atg aag cgt aag gtt aag aa g atg gca gct atg      472
                      Met Lys Arg Lys Val Lys Lys Met Ala  Ala Met
                        1               5                    10 gca acg agt ata att atg gct atc atg atc a tc cta cat agt ata cca       520
Ala Thr Ser Ile Ile Met Ala Ile Met Ile I le Leu His Ser Ile Pro
             15                  20                   25 gta ctc gcc ggg cga ata att tac gac aat g ag aca ggc aca cat gga       568
Val Leu Ala Gly Arg Ile Ile Tyr Asp Asn G lu Thr Gly Thr His Gly
         30                   35                      40 ggc tac gac tat gag ctc tgg aaa gac tac g ga aat acg att atg gaa       616
Gly Tyr Asp Tyr Glu Leu Trp Lys Asp Tyr G ly Asn Thr Ile Met Glu
         45                   50                      55 ctt aac gac ggt ggt act ttt agt tgt caa t gg agt aat atc ggt aat       664
Leu Asn Asp Gly Gly Thr Phe Ser Cys Gln T rp Ser Asn Ile Gly Asn
60                   65                      70                 75 gca cta ttt aga aaa ggg aga aaa ttt aat t cc gac aaa acc tat caa       712
Ala Leu Phe Arg Lys Gly Arg Lys Phe Asn S er Asp Lys Thr Tyr Gln
             80                    85                     90 gaa tta gga gac ata gta gtt gaa tat ggc t gt gat tac aat cca aac       760
Glu Leu Gly Asp Ile Val Val Glu Tyr Gly C ys Asp Tyr Asn Pro Asn
         95                   100                     105 gga aat tcc tat ttg tgt gtt tac ggt tgg a ca aga aat cca ctg gtt       808
Gly Asn Ser Tyr Leu Cys Val Tyr Gly Trp T hr Arg Asn Pro Leu Val
         110                  115                     120 gaa tat tac att gta gaa agc tgg ggc agc t gg cgt cca cct gga gca       856
Glu Tyr Tyr Ile Val Glu Ser Trp Gly Ser T rp Arg Pro Pro Gly Ala
         125                  130                     135 aca ccc aaa gga acc atc aca cag tgg atg g ca ggt act tat gaa ata       904
Thr Pro Lys Gly Thr Ile Thr Gln Trp Met A la Gly Thr Tyr Glu Ile
140                  145                     150                155 tat gaa act acc cgg gta aat cag cct tcc a tc gat gga act gcg aca       952
Tyr Glu Thr Thr Arg Val Asn Gln Pro Ser I le Asp Gly Thr Ala Thr
             160                  165                    170 ttc caa caa tat tgg agt gtt cgt aca tcc a ag aga aca agc gga aca      1000
Phe Gln Gln Tyr Trp Ser Val Arg Thr Ser L ys Arg Thr Ser Gly Thr
         175                  180                     185 ata tct gtc act gaa cat ttt aaa cag tgg g aa aga atg ggc atg cga      1048
Ile Ser Val Thr Glu His Phe Lys Gln Trp G lu Arg Met Gly Met Arg
         190                  195                     200 atg ggt aag atg tat gaa gtt gct ctt acc g tt gaa ggt tat cag agc      1096
Met Gly Lys Met Tyr Glu Val Ala Leu Thr V al Glu Gly Tyr Gln Ser
205                  210                     215 agt ggg tac gct aat gta tac aag aat gaa a tc aga ata ggt gca aat      1144
Ser Gly Tyr Ala Asn Val Tyr Lys Asn Glu I le Arg Ile Gly Ala Asn
220                  225                     230                235 cca act cct gcc cca tct caa agc cca att a ga aga gat gca ttt tca      1192
Pro Thr Pro Ala Pro Ser Gln Ser Pro Ile A rg Arg Asp Ala Phe Ser
             240                  245                    250 ata atc gaa gcg gaa gaa tat aac agc aca a at tcc tcc act tta caa      1240
Ile Ile Glu Ala Glu Glu Tyr Asn Ser Thr A sn Ser Ser Thr Leu Gln
         255                  260                     265 gtg att gga acg cca aat aat ggc aga gga a tt ggt tat att gaa aat      1288
Val Ile Gly Thr Pro Asn Asn Gly Arg Gly I le Gly Tyr Ile Glu Asn
         270                  275                     280
```

```
ggt aat acc gta act tac agc aat ata gat t tt ggt agt ggt gca aca    1336
Gly Asn Thr Val Thr Tyr Ser Asn Ile Asp P he Gly Ser Gly Ala Thr
        285                 290                 295 ggg ttc tct gca act gtt gca acg gag gtt a at acc tca att caa atc    1384
Gly Phe Ser Ala Thr Val Ala Thr Glu Val A sn Thr Ser Ile Gln Ile
300                 305                 310                 315 cgt tct gac agt cct acc gga act cta ctt g gt acc tta tat gta agt    1432
Arg Ser Asp Ser Pro Thr Gly Thr Leu Leu G ly Thr Leu Tyr Val Ser
                320                 325                 330 tct acc ggc agc tgg aat aca tat caa acc g ta tct aca aac atc agc    1480
Ser Thr Gly Ser Trp Asn Thr Tyr Gln Thr V al Ser Thr Asn Ile Ser
            335                 340                 345 aaa att acc ggc gtt cat gat att gta ttg g ta ttc tca ggt cca gtc    1528
Lys Ile Thr Gly Val His Asp Ile Val Leu V al Phe Ser Gly Pro Val
        350                 355                 360 aat gtg gac aac ttc ata ttt agc aga agt t ca cca gtg cct gca cct    1576
Asn Val Asp Asn Phe Ile Phe Ser Arg Ser S er Pro Val Pro Ala Pro
    365                 370                 375 ggt gat aac aca aga gac gca tat tct atc a tt cag gcc gag gat tat    1624
Gly Asp Asn Thr Arg Asp Ala Tyr Ser Ile I le Gln Ala Glu Asp Tyr
380                 385                 390                 395 gac agc agt tat ggt ccc aac ctt caa atc t tt agc tta cca ggt ggt    1672
Asp Ser Ser Tyr Gly Pro Asn Leu Gln Ile P he Ser Leu Pro Gly Gly
                400                 405                 410 ggc agc gcc att ggc tat att gaa aat ggt t at tcc act acc tat aaa    1720
Gly Ser Ala Ile Gly Tyr Ile Glu Asn Gly T yr Ser Thr Thr Tyr Lys
            415                 420                 425 aat att gat ttt ggt gac ggc gca acg tcc g ta aca gca aga gta gct    1768
Asn Ile Asp Phe Gly Asp Gly Ala Thr Ser V al Thr Ala Arg Val Ala
        430                 435                 440 acc cag aat gct act acc att cag gta aga t tg gga agt cca tcg ggt    1816
Thr Gln Asn Ala Thr Thr Ile Gln Val Arg L eu Gly Ser Pro Ser Gly
    445                 450                 455 aca tta ctt gga aca att tac gtg ggg tcc a ca gga agc ttt gat act    1864
Thr Leu Leu Gly Thr Ile Tyr Val Gly Ser T hr Gly Ser Phe Asp Thr
460                 465                 470                 475 tat agg gat gta tcc gct acc att agt aat a ct gcg ggt gta aaa gat    1912
Tyr Arg Asp Val Ser Ala Thr Ile Ser Asn T hr Ala Gly Val Lys Asp
                480                 485                 490 att gtt ctt gta ttc tca ggt cct gtt aat g tt gac tgg ttt gta ttc    1960
Ile Val Leu Val Phe Ser Gly Pro Val Asn V al Asp Trp Phe Val Phe
            495                 500                 505 tca aaa tca gga act taagggtata gaccctaatg tggagtac aa aatctggtat    2015
Ser Lys Ser Gly Thr
            510 ggcatatata aaaaaagact tggaattgta ccagtgcgac atataatggc t ttgtaaaat    2075 attctgatta aaacggaatg tttaaggata ggaaaagaaa gtattctttt c ctgtctttt    2135 ttatgtaacc ttaaaaatta cagccaatta ttcaataaaa taatttctgt a aatcagtta    2195 ttcttgaacc aatattaaaa gaatttcccc aaggtctttta atgtctggcc g gattacatt    2255 atcttctcct gtcattttaa aaaacagtta aatcaagctt tgtcgcaat a gaatgaatt    2315 attatttggg attccaaacc aaagacatat cattaagcag ttgtaaaaa             2364

<210> SEQ ID NO 24
<211> LENGTH: 512
<212> TYPE: PRT
<213> ORGANISM: Clostridium stercorarium
```

```
<400> SEQUENCE: 24

Met Lys Arg Lys Val Lys Lys Met Ala Ala Met Ala Thr Ser Ile Ile
  1               5                  10                  15

Met Ala Ile Met Ile Ile Leu His Ser Ile Pro Val Leu Ala Gly Arg
             20                  25                  30

Ile Ile Tyr Asp Asn Glu Thr Gly Thr His Gly Gly Tyr Asp Tyr Glu
             35                  40                  45

Leu Trp Lys Asp Tyr Gly Asn Thr Ile Met Glu Leu Asn Asp Gly Gly
         50                  55                  60

Thr Phe Ser Cys Gln Trp Ser Asn Ile Gly Asn Ala Leu Phe Arg Lys
 65                  70                  75                  80

Gly Arg Lys Phe Asn Ser Asp Lys Thr Tyr Gln Glu Leu Gly Asp Ile
                 85                  90                  95

Val Val Glu Tyr Gly Cys Asp Tyr Asn Pro Asn Gly Asn Ser Tyr Leu
             100                 105                 110

Cys Val Tyr Gly Trp Thr Arg Asn Pro Leu Val Glu Tyr Tyr Ile Val
             115                 120                 125

Glu Ser Trp Gly Ser Trp Arg Pro Pro Gly Ala Thr Pro Lys Gly Thr
         130                 135                 140

Ile Thr Gln Trp Met Ala Gly Thr Tyr Glu Ile Tyr Glu Thr Thr Arg
145                 150                 155                 160

Val Asn Gln Pro Ser Ile Asp Gly Thr Ala Thr Phe Gln Gln Tyr Trp
                 165                 170                 175

Ser Val Arg Thr Ser Lys Arg Thr Ser Gly Thr Ile Ser Val Thr Glu
             180                 185                 190

His Phe Lys Gln Trp Glu Arg Met Gly Met Arg Met Gly Lys Met Tyr
             195                 200                 205

Glu Val Ala Leu Thr Val Glu Gly Tyr Gln Ser Ser Gly Tyr Ala Asn
         210                 215                 220

Val Tyr Lys Asn Glu Ile Arg Ile Gly Ala Asn Pro Thr Pro Ala Pro
225                 230                 235                 240

Ser Gln Ser Pro Ile Arg Arg Asp Ala Phe Ser Ile Ile Glu Ala Glu
                 245                 250                 255

Glu Tyr Asn Ser Thr Asn Ser Ser Thr Leu Gln Val Ile Gly Thr Pro
             260                 265                 270

Asn Asn Gly Arg Gly Ile Gly Tyr Ile Glu Asn Gly Asn Thr Val Thr
             275                 280                 285

Tyr Ser Asn Ile Asp Phe Gly Ser Gly Ala Thr Gly Phe Ser Ala Thr
         290                 295                 300

Val Ala Thr Glu Val Asn Thr Ser Ile Gln Ile Arg Ser Asp Ser Pro
305                 310                 315                 320

Thr Gly Thr Leu Leu Gly Thr Leu Tyr Val Ser Ser Thr Gly Ser Trp
                 325                 330                 335

Asn Thr Tyr Gln Thr Val Ser Thr Asn Ile Ser Lys Ile Thr Gly Val
             340                 345                 350

His Asp Ile Val Leu Val Phe Ser Gly Pro Val Asn Val Asp Asn Phe
             355                 360                 365

Ile Phe Ser Arg Ser Ser Pro Val Pro Ala Pro Gly Asp Asn Thr Arg
         370                 375                 380

Asp Ala Tyr Ser Ile Ile Gln Ala Glu Asp Tyr Asp Ser Ser Tyr Gly
385                 390                 395                 400

Pro Asn Leu Gln Ile Phe Ser Leu Pro Gly Gly Gly Ser Ala Ile Gly
                 405                 410                 415
```

-continued

```
Tyr Ile Glu Asn Gly Tyr Ser Thr Thr Tyr L ys Asn Ile Asp Phe Gly
            420                 425             430

Asp Gly Ala Thr Ser Val Thr Ala Arg Val A la Thr Gln Asn Ala Thr
        435                 440             445

Thr Ile Gln Val Arg Leu Gly Ser Pro Ser G ly Thr Leu Leu Gly Thr
    450                 455             460

Ile Tyr Val Gly Ser Thr Gly Ser Phe Asp T hr Tyr Arg Asp Val Ser
465             470                 475                 480

Ala Thr Ile Ser Asn Thr Ala Gly Val Lys A sp Ile Val Leu Val Phe
            485                 490             495

Ser Gly Pro Val Asn Val Asp Trp Phe Val P he Ser Lys Ser Gly Thr
            500                 505             510
```

What is claimed is:

1. A recombinant DNA molecule comprising a vector sequence and a sequence encoding a feruloyl esterase protein, wherein said feruloyl esterase protein is characterized by an amino acid sequence having at least 75% amino acid sequence identity with amino acids 227 to 440 of SEQ ID NO:18.

2. The recombinant DNA molecule of claim 1, wherein said feruloyl esterase protein is characterized by the amino acid sequence given in amino acids 227 to 440 of SEQ ID NO:18.

3. The recombinant DNA molecule of claim 2, wherein the feruloyl esterase comprises the amino acid sequence given in SEQ ID NO:18, amino acids 5 to 530.

4. The recombinant DNA molecule of claim 3, wherein the sequence encoding the feruloyl esterase protein comprises the sequence given in SEQ ID NO:17, nucleotides 13 to 1590.

5. The recombinant DNA molecule of claim 3, wherein the feruloyl esterase comprises the sequence given in SEQ ID NO:18, amino acids 1 to 530.

6. The recombinant DNA molecule of claim 5, wherein the sequence encoding the feruloyl esterase protein comprises the sequence given in SEQ ID NO:17, nucleotides 1 to 1590.

7. A recombinant host cell comprising the recombinant DNA molecule of claim 1.

8. The recombinant host cell of claim 7, wherein said feruloyl esterase protein is characterized by the amino acid sequence given as amino acids 227 to 440 of SEQ ID NO:18.

9. The recombinant host cell of claim 8 wherein the feruloyl esterase comprises the amino acid sequence given in SEQ ID NO:18, amino acids 5 to 530.

10. The recombinant host cell of claim 9 wherein the sequence encoding the feruloyl esterase protein comprises the sequence given in SEQ ID NO:17, nucleotides 13 to 1590.

11. The recombinant host cell of claim 9 wherein the feruloyl esterase comprises the sequence given in SEQ ID NO:18, amino acids 1 to 530.

12. The recombinant host cell of claim 11, wherein the sequence encoding the feruloyl esterase protein comprises the sequence given in SEQ ID NO:17, nucleotides 1 to 1590.

13. A recombinant DNA molecule comprising a vector sequence and a sequence encoding a feruloyl esterase protein, wherein the feruloyl esterase protein consists of an amino acid sequence selected from the group consisting of amino acids 581 to 789 of SEQ ID NO:16, amino acids 346 to 789 of SEQ ID NO:16, amino acids 795 to 1077 of SEQ ID NO:12, amino acids 20 to 286 of SEQ ID NO:14, amino acids 20 to 307 of SEQ ID NO:14, and amino acids 20 to 421 of SEQ ID NO:14.

14. The recombinant DNA molecule of claim 13, wherein the feruloyl esterase consists of an amino acid sequence as given in SEQ ID NO:12, amino acids 795 to 1077.

15. The recombinant DNA molecule of claim 14, wherein the sequence encoding the feruloyl esterase protein is given in SEQ ID NO:11, nucleotides 2582–3430.

16. The recombinant DNA molecule of claim 13, wherein the feruloyl esterase consists of the amino acid sequence as given in SEQ ID NO:16, amino acids 546 to 789.

17. The recombinant DNA molecule of claim 16, wherein the sequence encoding the feruloyl esterase protein is given in SEQ ID NO:15, nucleotides 2164 to 2895.

18. The recombinant DNA molecule of claim 13, wherein the feruloyl esterase consists of an amino acid sequence as given in SEQ ID NO:14, amino acids 20 to 286.

19. The recombinant DNA molecule of claim 18, wherein the sequence encoding the feruloyl esterase protein is given in SEQ ID NO:13, nucleotides 158 to 958.

20. The recombinant DNA molecule of claim 13, wherein the feruloyl esterase consists of the amino acid sequence given in SEQ ID NO:14, amino acids 20 to 307.

21. The recombinant DNA molecule of claim 20, wherein the sequence encoding the feruloyl esterase protein is given in SEQ ID NO:13, nucleotides 158 to 1021.

22. The recombinant DNA molecule of claim 13, wherein the feruloyl esterase consists of the amino acid sequence given in SEQ ID NO:14, amino acids 20 to 421.

23. The recombinant DNA molecule of claim 22, wherein the sequence encoding the feruloyl esterase protein is given in SEQ ID NO:13, nucleotides 158 to 1363.

24. A recombinant host cell comprising the recombinant DNA molecule of claim 13.

25. A method for the recombinant production of a feruloyl esterase protein comprising the step of culturing a recombinant host cell comprising a vector sequence and a sequence encoding a feruloyl esterase protein, wherein the feruloyl esterase protein consists of an amino acid sequence selected from the group consisting of amino acids 581 to 789 of SEQ ID NO:16, amino acids 795 to 1077 of SEQ ID NO:12, amino acids 20 to 286 of SEQ ID NO:14, amino acids 20 to 307 of SEQ ID NO:14, amino acids 20 to 421 of SEQ ID NO:14, amino acids 5 to 530 of SEQ ID NO:18 and an amino acid sequence of at least 75% amino acid sequence identity with amino acids 227 to 440 of SEQ ID NO:18, under conditions of nutrition, time and temperature such that a feruloyl esterase protein is produced via expression of the sequence encoding the feruloyl esterase protein contained within the recombinant DNA molecule within said host cell.

26. The method of claim 25, wherein the feruloyl esterase protein consists of an amino acid sequence from the group consisting of amino acids 581 to 789 of SEQ ID NO:16, amino acids 795 to 1077 of SEQ ID NO:12, amino acids 845 to 1075 of SEQ ID NO:12, amino acids 20 to 286 of SEQ ID NO:14, amino acids 20 to 307 of SEQ ID NO:14, amino acids 20 to 421 of SEQ ID NO:14, amino acids 1 to 530 of SEQ ID NO:18, and amino acids 5 to 530 of SEQ ID NO:18.

* * * * *

UNITED STATES PATENT AND TRADEMARK OFFICE
CERTIFICATE OF CORRECTION

PATENT NO.    : 6,365,390 B1
DATED         : April 2, 2002
INVENTOR(S)   : Blum et al.

It is certified that error appears in the above-identified patent and that said Letters Patent is hereby corrected as shown below:

Column 7,
Line 24, delete "Tonmme" and replace with -- Tomme --.

Column 10,
Line 2, delete "C13D" and replace with -- CBD --.
Line 3, delete "XynlZ" and replace with -- XynZ --.
Line 34, delete "pl" and replace with -- pI --.

Column 12,
Line 28, delete "mind mg-I" and replace with -- min-1 mg-1 --.
Line 35, delete "CBS" and replace with -- CBG --.
Line 67, delete "aglionucleotide" and replace with -- oligonucleotide --.

Column 21,
Table 1, rows starting with $XYR1^c$, $XZR1^d$, $XZR2^d$, $XZR3^d$, $XZR4^d$, and $XZR5^d$, delete "GGAAGCTT" and replace with -- GGAAGCTT --.

Column 23,
Table 5 continued, nucleotide position 317, delete the amino acid code "M M" and replace with -- H N --.
Table 5 continued, nucleotide positions 442 and 457, delete the amino acid code "X" and replace with -- K --.
Table 5 continued, nucleotide position 689, delete the amino acid code "P" and replace with -- F --.

Column 25,
Table 5 continued, beneath the first line, delete "2400".
Table 5 continued, nucleotide positions 1127 and 1793, delete the amino acid code "X" and replace with -- K --.
Table 5 continued, nucleotide positions 1281 and 2027, delete the amino acid code "K" and replace with -- H --.
Table 5 continued, nucleotide positions 1709, delete the amino acid code "N" and replace with -- H --.

Column 27,
Table 5 continued, nucleotide position 2656, delete the amino acid code "N" and replace with -- H --.
Table 5 continued, nucleotide position 2944, delete the amino acid code "N" and replace with -- W --.
Table 5 continued, nucleotide position 3075, delete the amino acid code "M" and replace with -- N --.

UNITED STATES PATENT AND TRADEMARK OFFICE
CERTIFICATE OF CORRECTION

PATENT NO. : 6,365,390 B1
DATED : April 2, 2002
INVENTOR(S) : Blum et al.

It is certified that error appears in the above-identified patent and that said Letters Patent is hereby corrected as shown below:

Column 29,
Table 5 continued, nucleotide position 3174, delete the amino acid code "M" and replace with -- H --.

Column 32,
Table 6, amino acid position 224, delete "ILU" and replace with -- ILE --.
Table 6, amino acid position 254, delete "YYR" and replace with -- TYR --.
Table 6, amino acid position 300, delete the "300" over ILE.

Column 33,
Table 6 continued, amino acid position 353, place the pCT 1223 arrow one spot to the right, so that it is between "LYS" and "VAL".
Table 6 continued, nucleotide position 1105-1107, please replace "CGG" with -- CCG --.

Column 38,
Table 9, amino acid position 25, delete "=10" and shift amino acids 25-36 three nucleotide spaces to the left.

Column 101,
Line 67, delete "364" and replace with -- 546 --.

Signed and Sealed this

Twenty-sixth Day of November, 2002

*Attest:*

*Attesting Officer*

JAMES E. ROGAN
*Director of the United States Patent and Trademark Office*